US011912720B2

(12) United States Patent
Nalluri et al.

(10) Patent No.: US 11,912,720 B2
(45) Date of Patent: Feb. 27, 2024

(54) RIGID CHIRAL PHOTOLUMINESCENT ISOSCELES TRIANGULAR MATERIALS

(71) Applicants: Northwestern University, Evanston, IL (US); King Abdulaziz City for Science and Technology (KACST), Riyadh (SA)

(72) Inventors: Siva Krishna Mohan Nalluri, Chicago, IL (US); James Fraser Stoddart, Evanston, IL (US)

(73) Assignees: Northwestern University, Evanston, IL (US); King Abdulaziz City for Science and Technology (KACST), Riyadh (SA)

( * ) Notice: Subject to any disclaimer, the term of this patent is extended or adjusted under 35 U.S.C. 154(b) by 886 days.

(21) Appl. No.: 16/963,156

(22) PCT Filed: Jan. 21, 2019

(86) PCT No.: PCT/US2019/014415
§ 371 (c)(1),
(2) Date: Jul. 17, 2020

(87) PCT Pub. No.: WO2019/144074
PCT Pub. Date: Jul. 25, 2019

(65) Prior Publication Data
US 2021/0122767 A1 Apr. 29, 2021

Related U.S. Application Data

(60) Provisional application No. 62/619,561, filed on Jan. 19, 2018.

(51) Int. Cl.
*C07D 519/00* (2006.01)
*C09K 11/06* (2006.01)

(52) U.S. Cl.
CPC ............ *C07D 519/00* (2013.01); *C09K 11/06* (2013.01); *C09K 2211/1077* (2013.01)

(58) Field of Classification Search
None
See application file for complete search history.

(56) References Cited

U.S. PATENT DOCUMENTS

| | | |
|---|---|---|
| 5,700,298 A | 12/1997 | Shi |
| 9,546,169 B2 | 1/2017 | Stoddart |
| 10,745,418 B2 | 8/2020 | Stoddart |
| 2011/0137025 A1 | 6/2011 | Yaghi |
| 2015/0295229 A1 | 10/2015 | Rosciano et al. |
| 2016/0130271 A1 | 5/2016 | Stoddart |
| 2016/0276669 A1 | 9/2016 | Chen |
| 2019/0016738 A1 | 1/2019 | Stoddart |
| 2019/0077804 A1 | 3/2019 | Stoddart |

FOREIGN PATENT DOCUMENTS

| | | |
|---|---|---|
| WO | 2013004677 A1 | 1/2013 |
| WO | 2014067574 A1 | 5/2014 |
| WO | 2012121145 A1 | 7/2014 |

OTHER PUBLICATIONS

Safont-Sempere, M. M., et al. Chiral self-recognition and self-discrimination of strapped perylene bisimides by p-stacking dimerization. Chem. Eur. J. 16, 7380-7384 (2010).
Samanta, A. et al. Supramolecular double-helix formation by diastereoisomeric conformations of configurationally enantiomeric macrocycles. J. Am. Chem. Soc. 138, 14469-14480 (2016).
Samuel, I. D. W. et al. Organic Semiconductor Lasers. Chem. Rev. 2007, 107, 1272-1295.
Schlosser, F., et al. Excitation energy migration in covalently linked perylene bisimide macrocycles. Chem. Sci. 3, 2778-2785 (2012).
Schlosser, F., et al. Perylene bisimide macrocycles and their self-assembly on hopg surfaces. Chem. Commun. 46, 8350-8352 (2010).
Schmidt, R. et al. High-performance air-stable n-channel organic thin film transistors based on halogenated perylene bisimide semiconductors. J. Am. Chem. Soc. 131, 6215-6228 (2009).
Schneebeli, S. T., et al. "Electron sharing and anion-pi recognition in molecular triangular prisms." Angewandte Chemie International Edition vol. 52 (2013) pp. 13338-13342.
Sheldrick, G. M. "A short history of SHELX." Acta Crystallographica Section A: Foundations of Crystallography 64.1 (2008): 112-122.
Sheldrick, G., Shelxt—Integrated Space-Group and Crystal-Structure Determination. Acta. Cryst. A 2015, 71, 3-8.
Shimizu, M. et al. Organic Fluorophores Exhibiting Highly Efficient Photoluminescence in the Solid State. Chem. Asian J. 2010, 5, 1516-1531.
Shukla, D., et al. "Thin-film morphology control in naphthalene-diimide-based semiconductors: high mobility n-type semiconductor for organic thin-film transistors." Chemistry of Materials 20.24 (2008): 7486-7491.
Song et al., Polymer-graphene nanocomposites as ultrafast-charge and -discharge cathodes for rechargeable lithium batteries. Nano Lett. May 9, 2012;12(5):2205-11.
Thomas, S. W. et al. Chemical Sensors Based on Amplifying Fluorescent Conjugated Polymers. Chem. Rev. 2007, 107, 1339-1386.
Thorn, A., et al. (2012). Enhanced rigid-bond restraints. Acta Crystallographica Section A: Foundations of Crystallography, 68(4), 448-451.
Turner, M. J. et al. CrystalExplorer17. University of Western Australia: 2017. v.
Wakamiya, A., et al. 3-boryl-2,2'-bithiophene as a versatile core skeleton for full-color highly emissive organic solids. Angew. Chem., Int. Ed. 46, 4273-4276 (2007).

(Continued)

*Primary Examiner* — Zinna Northington Davis
(74) *Attorney, Agent, or Firm* — Quarles & Brady LLP

(57) ABSTRACT

Provided herein are rigid macrocycles comprising a poly (peri-naphthalene) diimide (PPNDI) submit and a second diimide subunit having both high photoluminescent and electron accumulation activities. Also provided herein are methods of preparation of the rigid macrocycles and methods of using the same.

20 Claims, 40 Drawing Sheets

(56) References Cited

OTHER PUBLICATIONS

Weil, T. et al. The Rylene Colorant Family-Tailored Nanoemitters for Photonics Research and Applications. Angew. Chem., Int. Ed. 2010, 49, 9068-9093.
Wu, Y. et al. Electron delocalization in a rigid cofacial naphthalene-1,8:4,5-bis(dicarboximide) dimer. Angew. Chem., Int. Ed. 53, 9476-9481 (2014).
Wu, Y. et al. Ultrafast photoinduced symmetry-breaking charge separation and electron sharing in perylenediimide molecular triangles. J. Am. Chem. Soc. 137, 13236-13239 (2015).
Wu, Y., et al. "Charge and spin transport in an organic molecular square." Angewandte Chemie International Edition 54.41 (2015): 11971-11977.
Wu, Y., et al. Spin frustration in the triradical trianion of a naphthalenediimide molecular triangle. J. Am. Chem. Soc. 139, 2948-2951 (2017).
Würthner, F. Bay-substituted perylene bisimides: Twisted fluorophores for supramolecular chemistry. Pure Appl. Chem. 78, 2341-2349 (2006).
Würthner, F. et al. Perylene bisimide dye assemblies as archetype functional supramolecular materials. Chem. Rev. 116, 962-1052 (2016).
Wurthner, F. Perylene bisimide dyes as versatile building blocks for functional supramolecular architectures. Chem. Commun., 1564-1579 (2004).
Yu, L. et al. New simple primary amine-thiourea organocatalysts and their application in asymmetric conjugate addition. Tetrahedron Lett. 55, 3697-3700 (2014).
Yuan, W. Z. et al. Changing the behavior of chromophores from aggregation-caused quenching to aggregation-induced emission: Development of highly efficient light emitters in the solid state. Adv. Mater. 22, 2159-2163 (2010).
Zaumseil, J. et al. Electron and Ambipolar Transport in Organic Field-Effect Transistors. Chem. Rev. 2007, 107, 1296-1323.
Zhan, X. et al. A high-mobility electron-transport polymer with broad absorption and its use in field-effect transistors and all-polymer solar cells. J. Am. Chem. Soc. 129, 7246-7247 (2007).
Zhan, X., et al. "Rylene and related diimides for organic electronics." Advanced Materials 23.2 (2011): 268-284.
Zhang, X. et al. A potential perylene diimide dimer-based acceptor material for highly efficient solution-processed non-fullerene organic solar cells with 4.03% efficiency. Adv. Mater. 25, 5791-5797 (2013).
Zhao, C.-H., et al. Highly emissive organic solids containing 2,5-diboryl-1,4-phenylene unit. J. Am. Chem. Soc. 128, 15934-15935 (2006).
Zhao, H.-M. et al. Understanding Ground- and Excited-State Properties of Perylene Tetracarboxylic Acid Bisimide Crystals by Means of Quantum Chemical Computations. J. Am. Chem. Soc. 2009, 131, 15660-15668.
Zhao, Y. et al. Density functionals with broad applicability in chemistry. Acc. Chem. Res. 41, 157-167 (2008).
Zhao, Y. et al. The m06 suite of density functionals for main group thermochemistry, thermochemical kinetics, noncovalent interactions, excited states, and transition elements: Two new functionals and systematic testing of four m06-class functionals and 12 other functionals. Theor. Chem. Acc. 120, 215-241 (2008).
Zhou, E. et al. All-polymer solar cells from perylene diimide based copolymers: Material design and phase separation control. Angew. Chem., Int. Ed. 50, 2799-2803 (2011).
An, B.-K., et al. Enhanced emission and its switching in fluorescent organic nanoparticles. J. Am. Chem. Soc. 124, 14410-14415 (2002).
Anthony, J. E., et al. N-type organic semiconductors in organic electronics. Adv. Mater. 22, 3876-3892 (2010).
Au-Yeung, H. Y., et al. "Templated amplification of a naphthalenediimide-based receptor from a donor-acceptor dynamic combinatorial library in water." Chemical communications 4 (2009): 419-421.
Avlasevich, Y. et al. "An efficient synthesis of quaterrylenedicarboximide NIR dyes." The Journal of organic chemistry 72.26 (2007): 10243-10246.

Beddard, G. et al. Concentration quenching in chlorophyll. Nature 1976, 260, 366-367.
Brown, K. E. et al. Direct Observation of Ultrafast Excimer Formation in Covalent Perylenediimide Dimers Using Near-Infrared Transient Absorption Spectroscopy. J. Phys. Chem. Lett. 2014, 5, 2588-2593.
Che, Y. et al. Interfacial engineering of organic nanofibril heterojunctions into highly photoconductive materials. J. Am. Chem. Soc. 133, 1087-1091 (2011).
Che, Y., et al. Highly polarized and self-waveguided emission from single-crystalline organic nanobelts. Chem. Mater. 21, 2930-2934 (2009).
Chen, D., et al. "A Rigid Naphthalenediimide Triangle for Organic Rechargeable Lithium-Ion Batteries." Advanced Materials 27.18 (2015): 2907-2912.
Chen, J., et al. "PPN (poly-peri-naphthalene) film as a narrow-bandgap organic thermoelectric material." Journal of Materials Chemistry A 5.20 (2017): 9891-9896.
Chen, Z. J. et al. Colorimetric and ratiometric fluorescent chemosensor for fluoride ion based on perylene diimide derivatives. Dyes Pigm. 94, 410-415 (2012).
Cook, R. E. et al. Excimer Formation and Symmetry-Breaking Charge Transfer in Cofacial Perylene Dimers. J. Phys. Chem. A 2017, 121, 1607-1615.
Dodabalapur, A. et al. Organic Solid-State Lasers: Past and Future. Science 1997, 277, 1787-1788.
Dolomanov, O. V., et al. "OLEX2: a complete structure solution, refinement and analysis program." Journal of applied crystallography 42.2 (2009): 339-341.
Duan, L. et al. Strategies to Design Bipolar Small Molecules for OLEDs: Donor-Acceptor Structure and Non-Donor-Acceptor Structure. Adv. Mater. 2011, 23, 1137-1144.
Friend, R. et al. Electroluminescence in Conjugated Polymers. Nature 1999, 397, 121-128.
Gawronski, J., et al. "Novel Chiral Pyromellitdiimide (1, 2, 4, 5-Benzenetetracarboxydiimide) Dimers and Trimers: Exploring Their Structure, Electronic Transitions, and Exciton Coupling." Chemistry—A European Journal 8.11 (2002): 2484-2494.
Gawronski, J., et al. Chirality of aromatic bis-imides from their circular dichroism spectra. Chirality 12, 263-268 (2000).
Goerigk, L. et al. A thorough benchmark of density functional methods for general main group thermochemistry, kinetics, and noncovalent interactions. Phys. Chem. Chem. Phys. 13, 6670-6688 (2011).
Görl, D., et al. Molecular assemblies of perylene bisimide dyes in water. Angew. Chem., Int. Ed. 51, 6328-6348 (2012).
Grimme, S. et al. A consistent and accurate ab initio parametrization of density functional dispersion correction (dft-d) for the 94 elements h-pu. J. Chem. Phys. 132, 154104 (2010).
Grimsdale, A. C. et al. Synthesis of Light-Emitting Conjugated Polymers for Applications in Electroluminescent Devices. Chem. Rev. 2009, 109, 897-1091.
Höger, S. "Shape-persistent macrocycles: from molecules to materials." Chemistry—A European Journal 10.6 (2004): 1320-1329.
Hou, X. et al. Tunable solid-state fluorescent materials for supramolecular encryption. Nat. Commun. 6 (2015).
Iida, A. et al. Intense solid-state blue emission with a small stokes' shift: [small pi]-stacking protection of the diphenylanthracene skeleton. Chem. Commun., 3002-3004 (2009).
International Searching Authority, International Search Report and Written Opinion for application PCT/US2019/014415, dated Apr. 4, 2019.
Jimenez, A. J. et al. Structure-property relationships for 1,7-diphenoxy-perylene bisimides in solution and in the solid state. Chem. Sci. 5, 608-619 (2014).
Jones, B. A. et al. High-mobility air-stable n-type semiconductors with processing versatility: Dicyanoperylene-3,4:9,10-bis(dicarboximides). Angew. Chem., Int. Ed. 43, 6363-6366 (2004).
Kaiser, T. E., et al. Supramolecular construction of fluorescent j-aggregates based on hydrogen-bonded perylene dyes. Angew. Chem., Int. Ed. 46, 5541-5544 (2007).

(56) References Cited

OTHER PUBLICATIONS

Kazmaier, P. M. et al. A Theoretical Study of Crystallochromy. Quantum Interference Effects in the Spectra of Perylene Pigments. J. Am. Chem. Soc. 1994, 116, 9684-9691.
Krieg, E., et al. A recyclable supramolecular membrane for size-selective separation of nanoparticles. Nat Nano 6, 141-146 (2011).
Kumar, J. et al. Circularly Polarized Luminescence in Chiral Molecules and Supramolecular Assemblies. J. Phys. Chem. Lett. 2015, 6, 3445-3452.
Larrow, J. et al. (R, R)-N, N'-Bis (3, 5-Di-Tert-Butylsalicylidene)-1, 2-Cyclohexanediamino Manganese (Iii) Chloride, A Highly Enantioselective Epoxidation Catalyst:(Manganese, Chloro 2, 2'-1, 2-Cyclohexanediylbis (Nitrilomethylidyne)-Bis 4, 6-Bis (1, 1-Dimethylethyl) Phenalato (2-)-N, N', O, O'-, Sp-5-1 3-(1 R-Trans-). Org. Synth. 1998, 75, 1-11.
Lee, Y.- T., et al. Solid-state highly fluorescent diphenylaminospirobifluorenylfumaronitrile red emitters for non-doped organic light-emitting diodes. Chem. Commun., 217-219 (2008).
Li, C. et al. Perylene imides for organic photovoltaics: Yesterday, today, and tomorrow. Adv. Mater. 24, 613-636 (2012).
Liu, Z., et al. "Assembly of supramolecular nanotubes from molecular triangles and 1, 2-dihalohydrocarbons." Journal of the American Chemical Society 136.47 (2014): 16651-16660.
Liu, Z., et al. "Supramolecular Gelation of Rigid Triangular Macrocycles through Rings of Multiple C—H—O Interactions Acting Cooperatively." The Journal of organic chemistry 81.6 (2016): 2581-2588.
Liu, Z., et al. Surveying macrocyclic chemistry: From flexible crown ethers to rigid cyclophanes. Chem. Soc. Rev. 46, 2459-2478 (2017).
Longhi, G. et al. Circularly Polarized Luminescence: A Review of Experimental and Theoretical Aspects. Chirality 2016, 28, 696-707.
Luo, J. et al. Aggregation-induced emission of 1-methyl-1,2,3,4,5-pentaphenylsilole. Chem. Commun., 1740-1741 (2001).
Mei, J., et al. Aggregation-induced emission: Together we shine, united we soar! Chem. Rev. 115, 11718-11940 (2015).
Mizuno, A. et al. 3d spin-liquid state in an organic hyperkagome lattice of mott dimers. Phys. Rev. Lett. 119, 057201 (2017).
Mizuno, A., et al. "Discovery of the K 4 Structure Formed by a Triangular p Radical Anion." Journal of the American Chemical Society 137.24 (2015): 7612-7615.
Nalluri, S. K. M. et al. Chiral redox-active isosceles triangles. J. Am. Chem. Soc. 138, 5968-5977 (2016).
Ning, Z. et al. Aggregation-induced emission (aie)-active starburst triarylamine fluorophores as potential non-doped red emitters for organic light-emitting diodes and cl2 gas chemodosimeter. Adv. Funct. Mater. 17, 3799-3807 (2007).
Pubchem-CID-102079549, Create Date: Dec. 24, 2015.
Qin, T. et al. Polytriphenylene dendrimers: A unique design for blue-light-emitting materials. Angew. Chem., Int. Ed. 47, 8292-8296 (2008).
Ramanan, C., et al. Competition between singlet fission and charge separation in solution-processed blend films of 6, 13-bis(triisopropylsilylethynyl)pentacene with sterically-encumbered perylene-3,4:9, 10-bis(dicarboximide)s. J. Am. Chem. Soc. 134, 386-397 (2012).
Rüger, R., et al. Tight-binding approximations to time-dependent density functional theory—a fast approach for the calculation of electronically excited states. J. Chem. Phys. 144, 184103 (2016).
Safont-Sempere, M. M. et al. Impact of molecular flexibility on binding strength and self-sorting of chiral p-surfaces. J. Am. Chem. Soc. 133, 9580-9591 (2011).

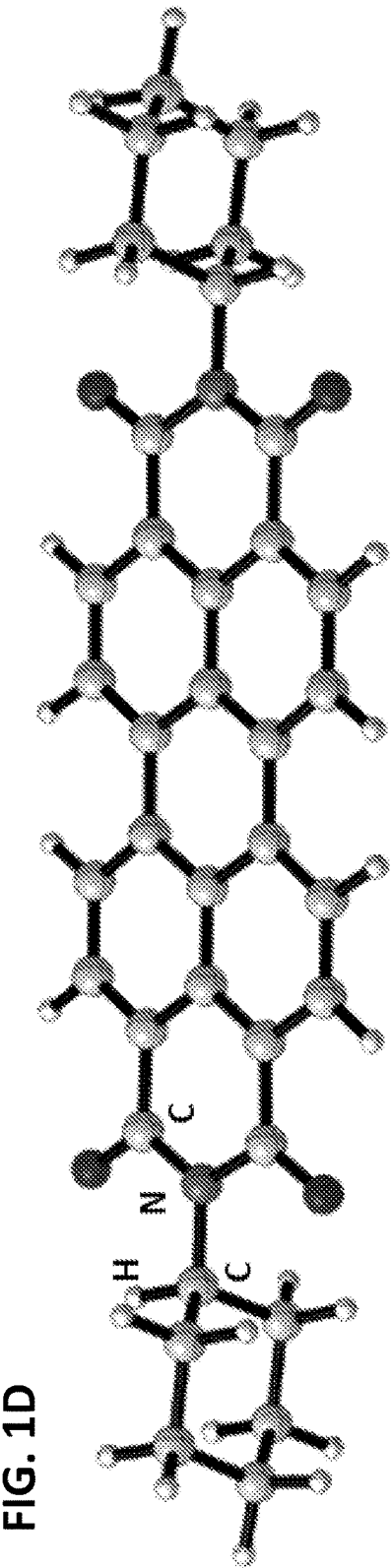
FIG. 1D
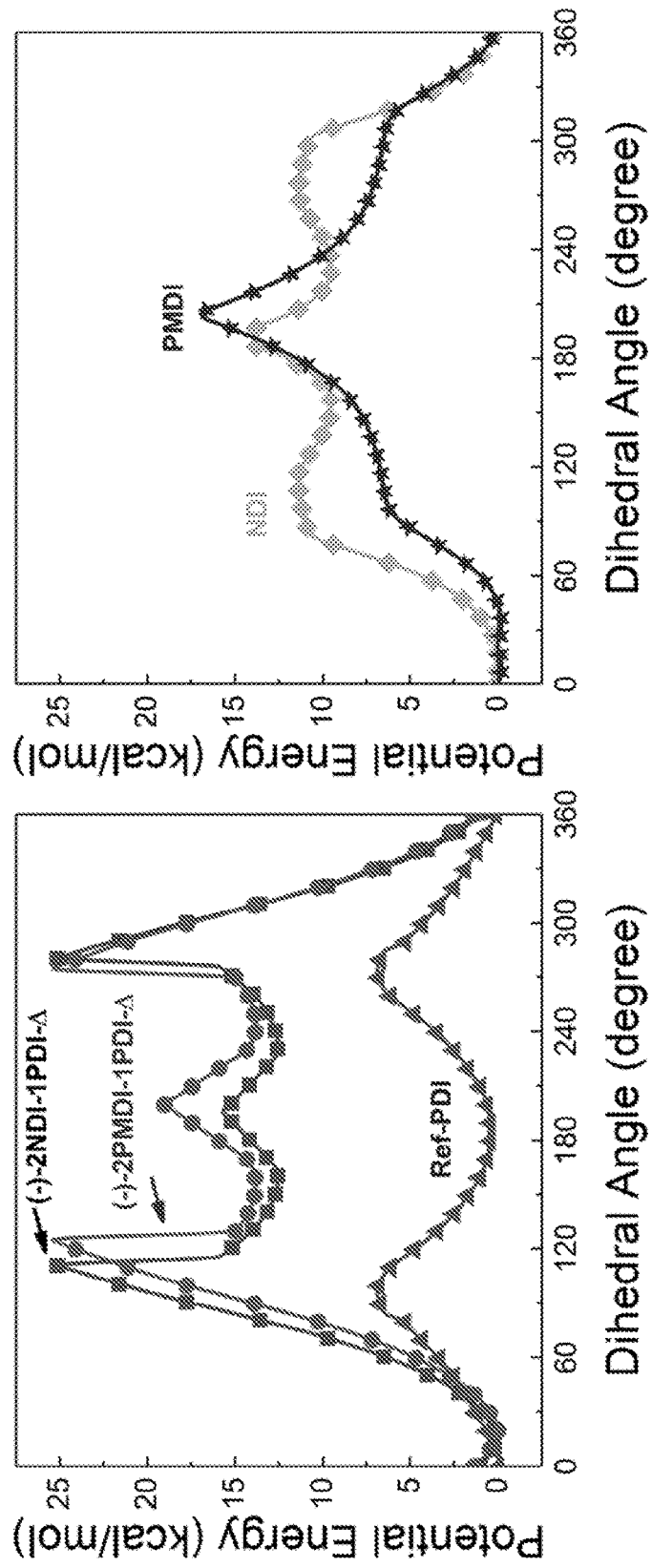
FIG. 1E
FIG. 1F

3.4 Å

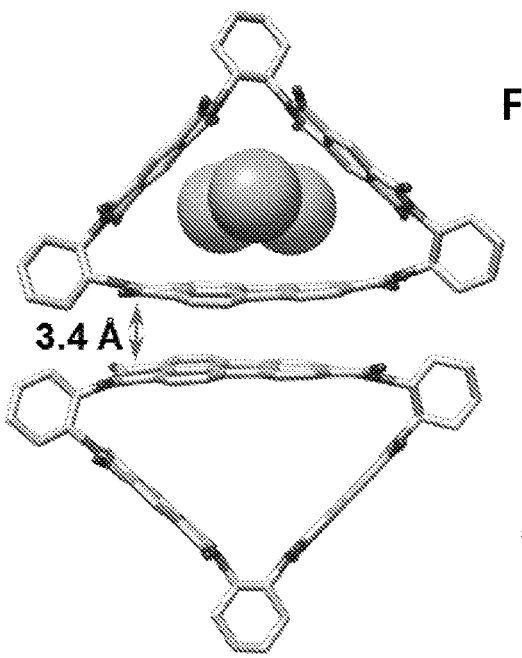
FIG. 2O
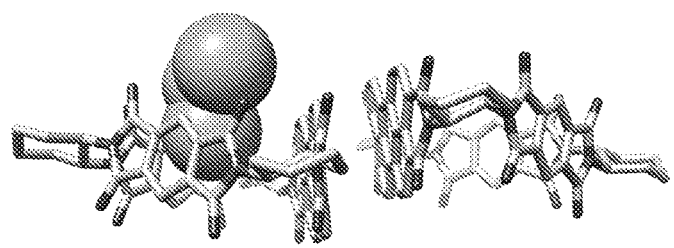
FIG. 2P
FIG. 2Q
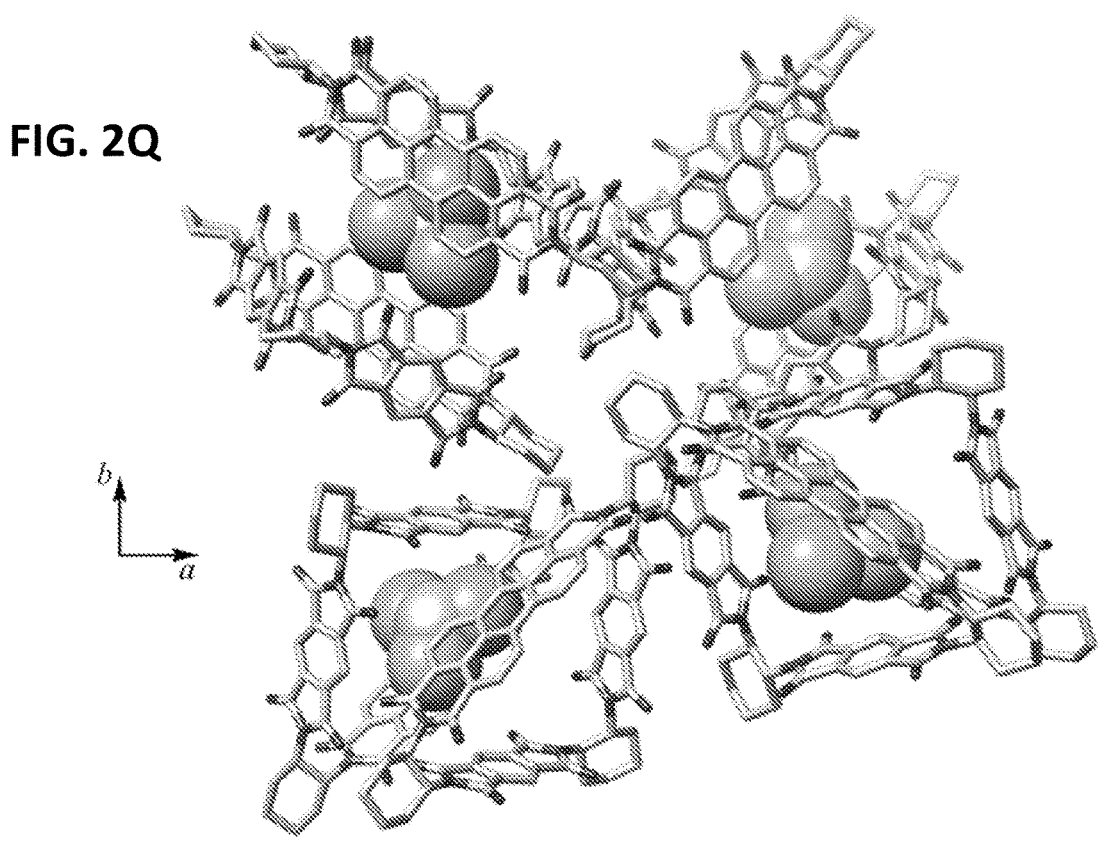

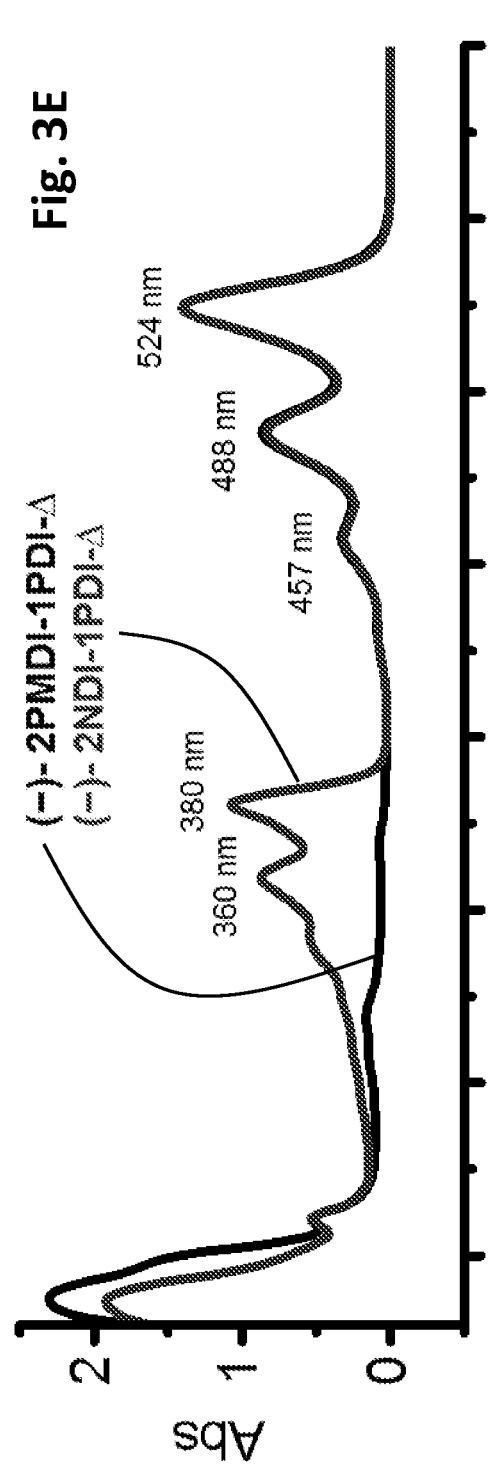
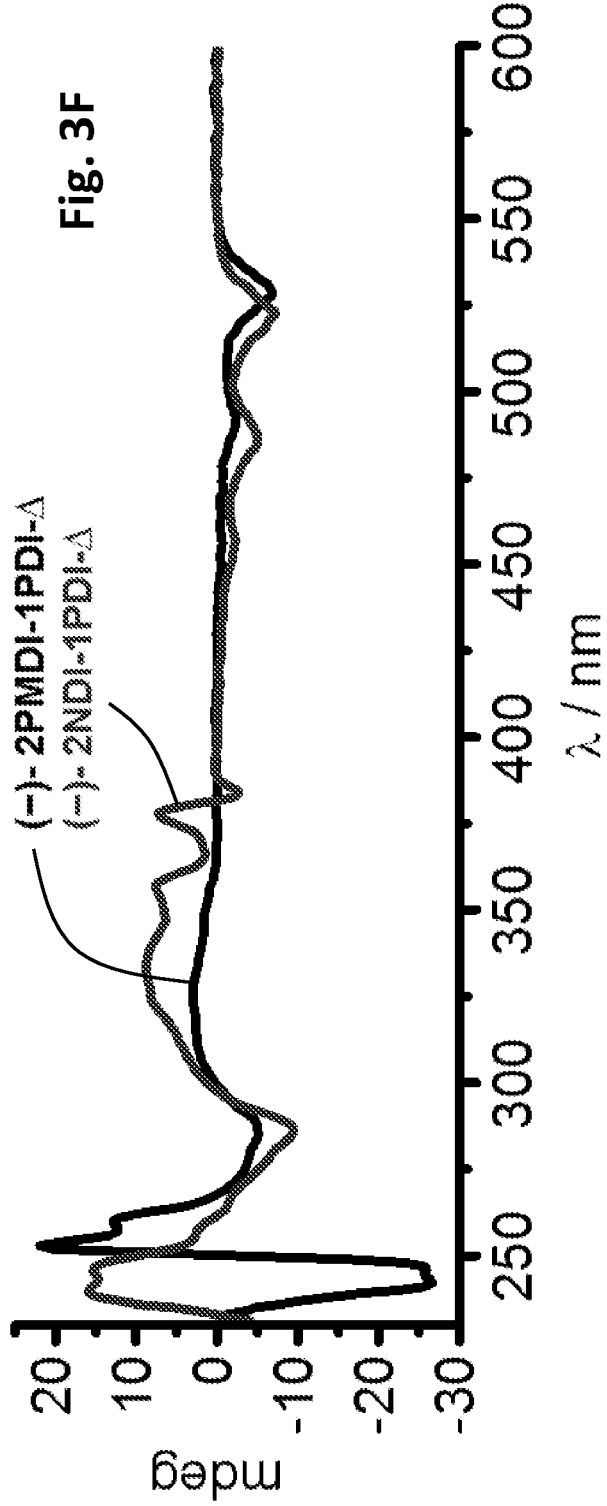

HOMO-3 / $\Delta E = -29.61$

HOMO-2 / $\Delta E = -29.56$

HOMO-1 / $\Delta E = -29.46$

HOMO / $\Delta E = 0.0$

LUMO / $\Delta E = 57.32$

HOMO−3 / ΔE = −28.07

HOMO−2 / ΔE = −22.33

HOMO−1 / ΔE = −21.81

HOMO / ΔE = 0.0

LUMO / ΔE = 57.51

PDI @ 2PMDI-1PDI-Δ
Δ$E$ (strain) = 11.77

PDI @ 2NDI-1PDI-Δ
Δ$E$ (strain) = 11.76

RIGID CHIRAL PHOTOLUMINESCENT ISOSCELES TRIANGULAR MATERIALS

The present application represents the U.S. national stage entry of International Application PCT/US2019/014415, filed Jan. 21, 2019, which claims the benefit of priority of Untied States Provisional Patent Application No. 62/619,561, filed Jan. 19, 2018, wherein both are incorporated herein by reference in their entirety.

BACKGROUND

The design and development of rigid covalent chiroptical organic materials, with multiple, readily available redox states, which exhibit high photoluminescence are of both scientific and technological interest, particularly in the fields of both organic electronics and photonics. Perylene diimide (PDI) fluorophores have been investigated increasingly in the recent past owing to their high fluorescence quantum yields in solution. However, the planar PDI derivatives suffer from emission quenching in the solid state, hampering their potential use in optoelectronic applications.

BRIEF SUMMARY OF THE INVENTION

Disclosed herein are rigid macrocycle comprising (a) three diimide subunits, the three diimide subunits consisting of (i) a poly(peri-naphthalene) diimide (PPNDI) subunit and (ii) two naphthalene diimide (NDI) subunits or two pyromellitic diimide (PMDI) subunits, and (b) three chiral linking subunits linking the three diimide subunits. In some embodiments, the PPNDI subunit comprises a PPNDI of formula

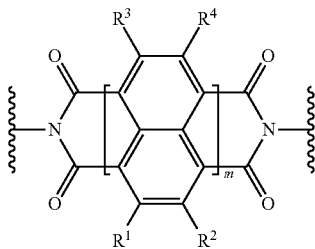

wherein each of $R^1$, $R^2$, $R^3$, and $R^4$ of the PPNDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, and a sulfate moiety and m is greater than or equal to 2 and less than or equal to 10. In some embodiments, the NDI subunit comprises a NDI of formula

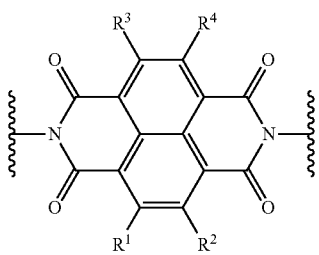

wherein each of $R^1$, $R^2$, $R^3$, and $R^4$ of the NDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety. In some embodiments, the PMDI subunit comprises a PMDI of formula

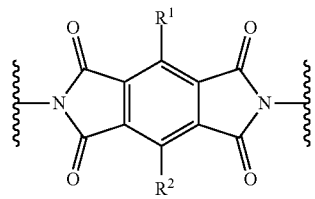

wherein each of $R^1$ and $R^2$ of the PMDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety. In some embodiments, the three chiral linking subunits are (i) a (RR)-trans-1,2-cycloalkyl subunit, (ii) a (SS)-trans-1,2-cycloalkyl subunit, or a derivative of either (i) or (ii).

Suitably, the macrocycle may comprise the PPNDI of formula

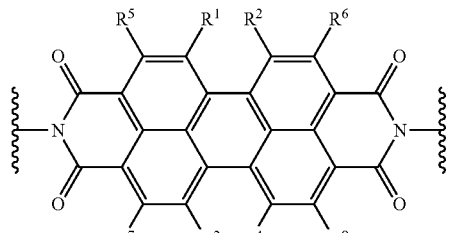

wherein each of $R^1$, $R^2$, $R^3$, $R^4$, $R^5$, $R^6$, $R^7$, and $R^8$ of the PDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, and a sulfate moiety; the macrocycle comprises the PMDI of formula

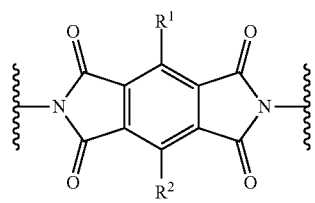

wherein each of $R^1$ and $R^2$ of the PMDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety; and wherein the three chiral linking subunits are (i) a (RR)-trans-1,2-cycloalkyl subunit, (ii) a (SS)-trans-1,2-cycloalkyl subunit, or a derivative of either (i) or (ii). In certain embodiments, the macrocycle is a compound of Formula (6)

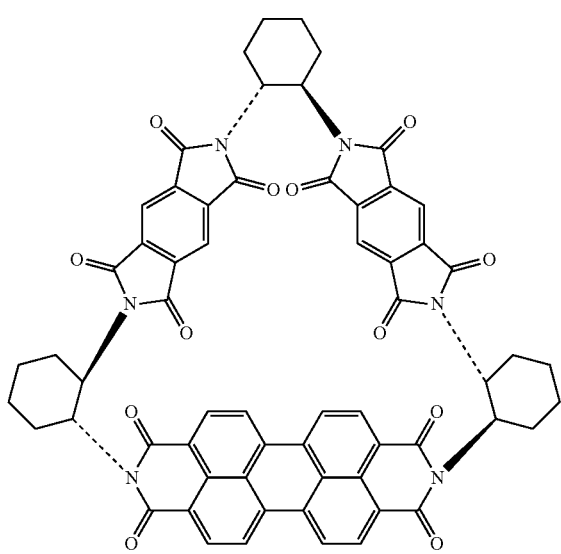

or a compound of Formula (7)

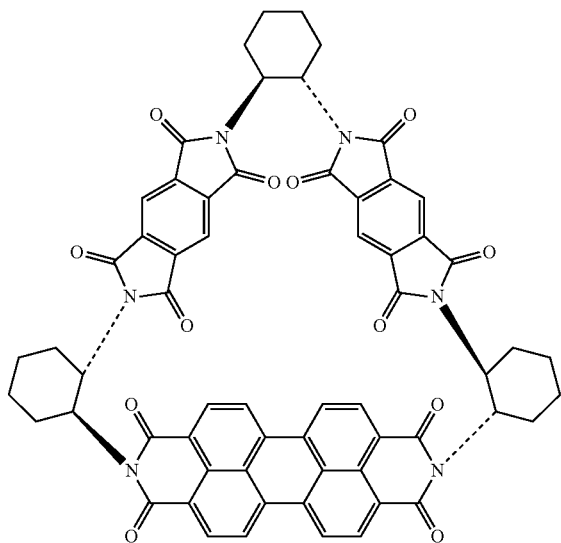

Suitably, the macrocycle comprises the PPNDI of formula

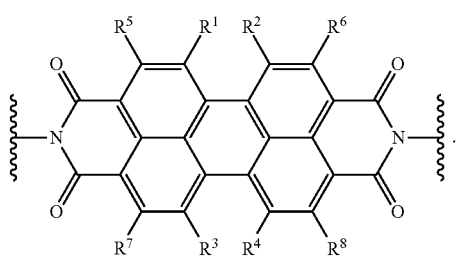

wherein each of $R^1$, $R^2$, $R^3$, $R^4$, $R^5$, $R^6$, $R^7$, and $R^8$ of the PDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, and a sulfate moiety; the macrocycle comprises the NDI of formula

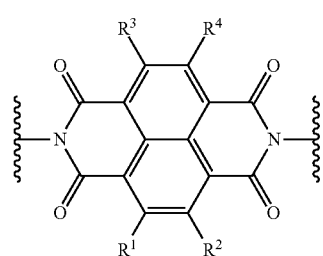

wherein each of $R^1$, $R^2$, $R^3$, and $R^4$ of the NDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety; and the three chiral linking subunits are (i) a (RR)-trans-1,2-cycloalkyl subunit, (ii) a (SS)-trans-1,2-cycloalkyl subunit, or a derivative of either (i) or (ii). In some embodiments, the macrocycle is a compound of Formula (4)

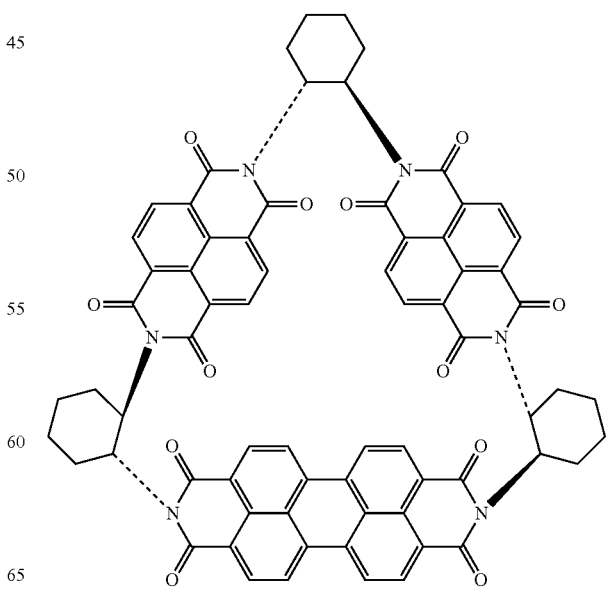

or a compound of Formula (5)

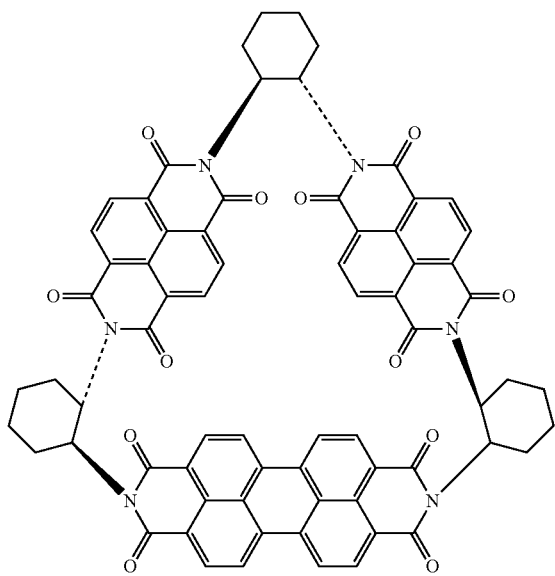

Another aspect of the invention comprises a crystalline composition comprising a plurality of any of the rigid macrocycles described herein. In some embodiments, the plurality of rigid macrocycles is arranged in a plurality of dimers by π-π stacking PPNDI subunits. Suitably, the PPNDI subunits of the dimer are separated by 3.3 Å to 3.5 Å.

Another aspect of the invention is a photolumine scent material comprising any of the rigid macrocycles described herein. The material may comprise a crystalline composition comprising a plurality of the rigid macrocycles. In some embodiments, the plurality of rigid macrocycles is arranged in a plurality of dimers by π-π stacking PPNDI subunits. Suitably, the PDI subunits of the dimer are separated by about 3.3 Å to about 3.5 Å. In some embodiments, the material has a quantum yield is greater than 0.5.

Another aspect of the invention is a method of preparing a rigid macrocycle, the method comprising cyclocondensing a first reagent comprising a compound of formula

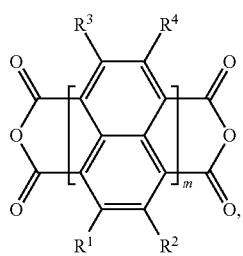

wherein each of $R^1$, $R^2$, $R^3$, and $R^4$ is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, and a sulfate moiety and m is greater than or equal to 2 and less than or equal to 10, and a second reagent comprising (i) two NDI subunits or two PMDI subunits and (ii) three chiral linking subunits. In some embodiments, each of the two NDI subunits comprises a NDI of formula

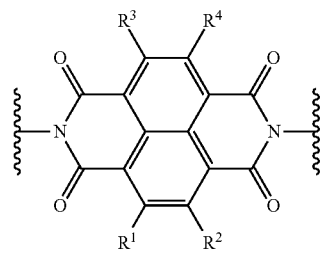

wherein each of $R^1$, $R^2$, $R^3$, and $R^4$ of the NDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety. In some embodiments, the two PMDI subunits comprise a PMDI of formula

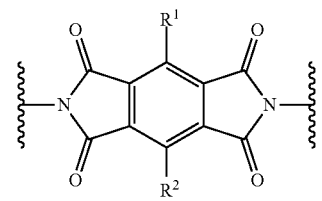

wherein each of $R^1$ and $R^2$ of the PMDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety. In some embodiments, the three chiral linking subunits are (i) a (RR)-trans-1,2-cycloalkyl subunit, (ii) a (SS)-trans-1,2-cycloalkyl subunit, or a derivative of either (i) or (ii). Suitably, the second reagent may be a compound of Formula (10)

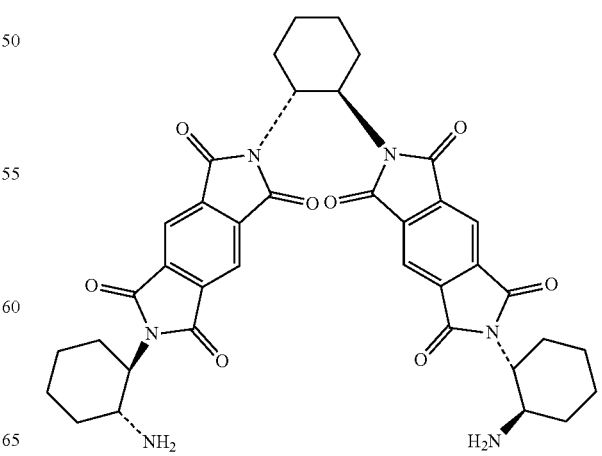

or a compound of Formula (11)

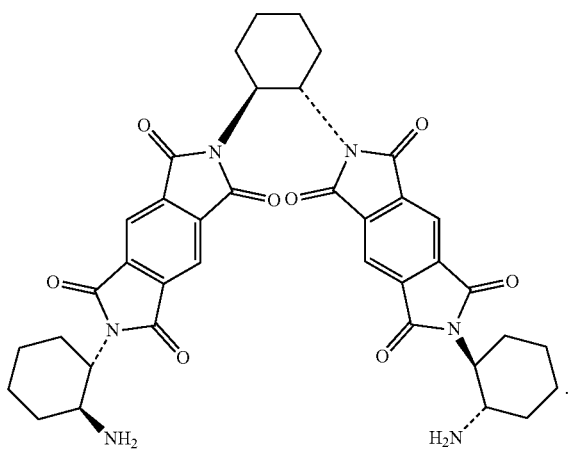

Suitably, the second reagent is a compound of Formula (8)

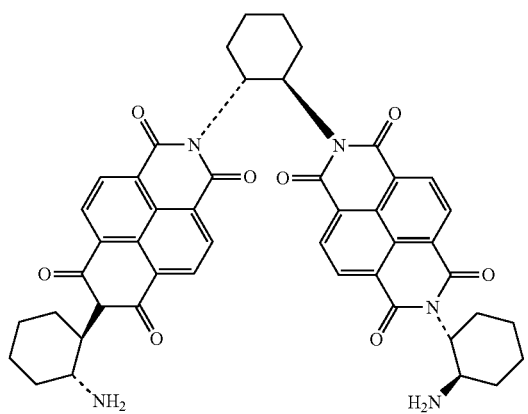

or a compound of Formula (9)

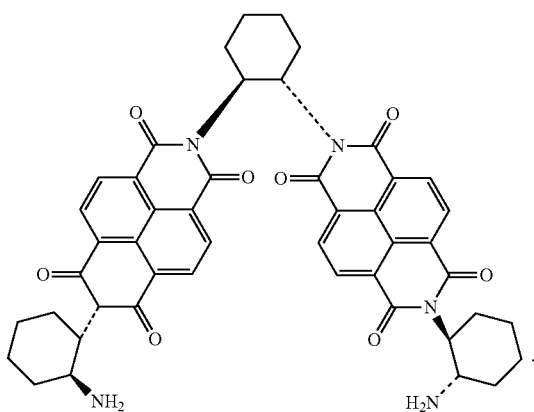

Another aspect of the invention is a method for stimulating light emission, the method comprising: providing any of the photoluminescent materials described herein and exciting the macrocycle with electromagnetic radiation in the near-ultraviolet or visible range. Suitably, wherein the material is excited by electromagnetic radiation having a wavelength of 200 nm to 700 nm and/or emits electromagnetic radiation having a wavelength of 350 nm to 800 nm. In some embodiments, the material emits electromagnetic radiation having $\lambda_{max}$ wavelength of about 500 nm to about 715 nm. In some embodiments, the material has a quantum yield is greater than 0.5.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 1D provides a graphical representation of Ref-PDI, calculated on the level of M06-2X density functional with 6-311G(d,p) basis sets, showing the dihedral rotation of ∠H—C—N—C.

FIG. 1E shows the potential energy surface as a function of the dihedral angle (∠H—C—N—C) for PDI subunits present in Ref-PDI (triangle), (−)-2PMDI-1PDI-Δ (circle) and (−)-2NDI-1PDI-Δ (square).

FIG. 1F shows the potential energy surface as a function of the dihedral angle (∠H—C—N—C) for NDI subunit in (−)-2NDI-1PDI-Δ (diamond) and PMDI subunit in (−)-2PMDI-1PDI-Δ (star).

FIGS. 2O-2Q show single-crystal X-ray structures from a top (FIG. 2O) and side-on (FIG. 2P) views of π-π stacking dimers of (−)-2PMDI-1PDI-Δ where $CHCl_3$ molecule, depicted in space-filling representation, is bound to one of the cavities by means of [C—H . . . O] interactions (FIGS. 2O and 2P) and a view along c-axis of the unit cell of (−)-2PMDI-PDI-Δ (FIG. 2Q).

FIGS. 3A-3C show normalized UV/Vis absorption (black solid line), excitation (red dashed line) and fluorescence emission (red solid line) spectra of Ref-PDI (a) (FIG. 3A), (−)-2PMDI-1PDI-Δ (FIG. 3B) and (−)-2NDI-1PDI-Δ (FIG. 3D) recorded in $CH_2Cl_2$ at 298 K. FIG. 3D shows fluorescence decay curves of Ref-PDI (lower trace at longer times), (−)-2PMDI-1PDI-Δ (middle trace at longer times), (−)-2NDI-1PDI-Δ (upper trace at longer times). The fluorescence spectra of all three compounds were obtained with the excitation at 493 nm.

FIGS. 3E and 3F show a UV-Vis absorption (FIG. 3E) and a CD spectra (FIG. 3F) of the rigid isosceles triangles (−)-2PMDI-1PDI-Δ and (−)-2NDI-1PDI-Δ recorded in $CH_2Cl_2$ at 298 K.

FIG. 4A shows diffuse reflectance UV/Vis spectra of Ref-PDI (b), (−)-2PMDI-1PDI-Δ (c) and (−)-2NDI-1PDI-Δ (d) recorded in the solid state at 298 K. FIGS. 4B-4D show normalized photoluminescence and excitation spectra of Ref-PDI (FIG. 4B), (−)-2PMDI-1PDI-Δ (FIG. 4C) and (−)-2NDI-1PDI-Δ (FIG. 4D) recorded in the solid state at 298 K. FIGS. 4E-4G show photoluminescence photographs of Ref-PDI (FIG. 4E), (−)-2PMDI-1PDI-Δ (FIG. 4F) and (−)-2NDI-1PDI-Δ (FIG. 4G) in powder form (left) as well as a drop-casting film coated on a glass substrate (right) under daylight (top) and upon 365 nm UV light irradiation (bottom). The photoluminescence spectra of all three compounds were obtained with the excitation at 360 nm.

FIGS. 6A-6E show graphical representations from HOMO-3 (FIG. 6A), HOMO-2 (FIG. 6B), HOMO-1 (FIG. 6C), HOMO (FIG. 6D), and LUMO (FIG. 6E) of (−)-2PMDI-1PDI-Δ from DFT calculations at the M06-2X level of theory using 6-311G(d,p) basis sets. FIGS. 6F-6J show graphical representations from HOMO-3 (FIG. 6F), HOMO-2 (FIG. 6G), HOMO-1 (FIG. 6H), HOMO (FIG. 6I), and LUMO (FIG. 6J) of (−)-2NDI-1PDI-Δ from DFT calculations at the M06-2X level of theory using 6-311G(d,p) basis sets. FIGS. 6K and 6L show graphical representations showing the curved PDI plane in (−)-2PMDI-1PDI-Δ (FIG. 6K) and (−)-2NDI-1PDI-Δ (FIG. 6L) in comparison with the fully relaxed PDI component. The molecular orbital energies are referenced to the molecular orbital energy of HOMO. All the energy units are shown in kcal $mol^{-1}$.

Figure 7A:
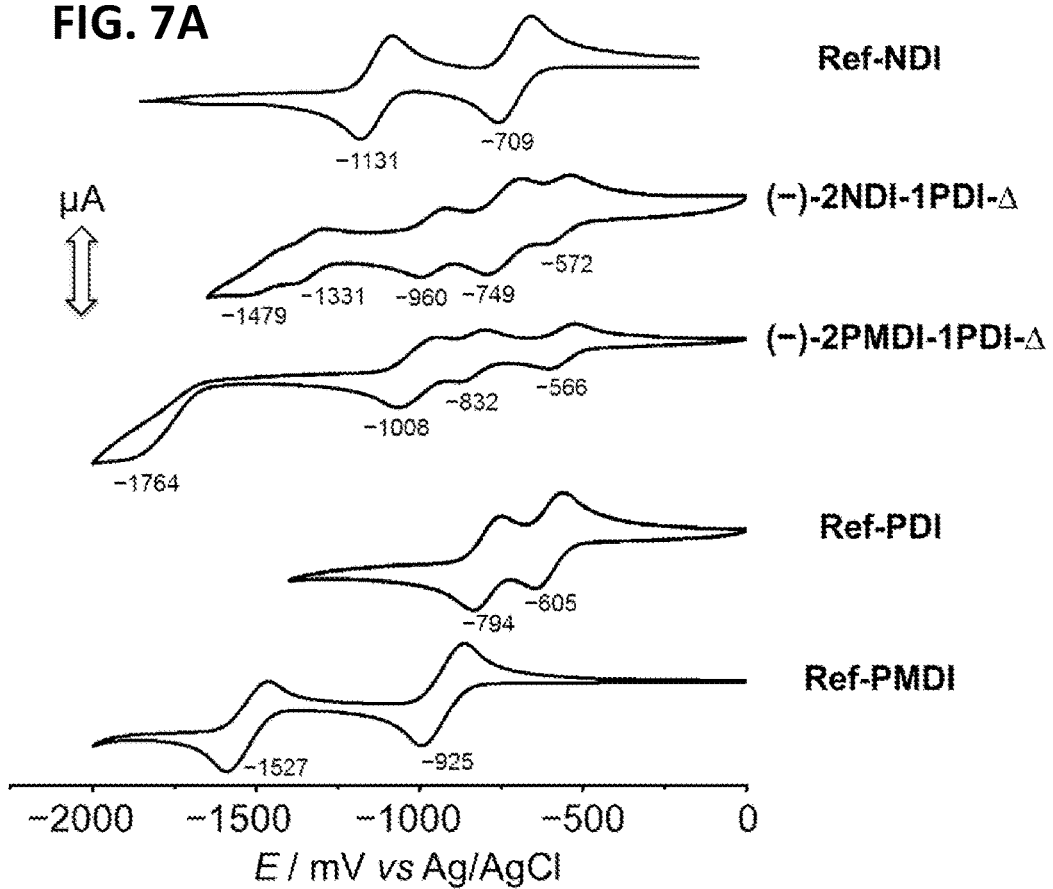
FIG. 7A shows cyclic voltammetry of isosceles triangles and reference compounds. Cyclic Voltammograms of (0.2 mM in CH$_2$Cl$_2$, 100 mM TBAPF$_6$, 50 mVs$^{-1}$, 298 K) of Ref-NDI, (−)-2NDI-1PDI-Δ, (−)-2PMDI-1PDI-Δ, Ref-PDI and Ref-PMDI. Half-wave peak potentials (E$_{1/2}$) are shown in mV.
Figure 7B:
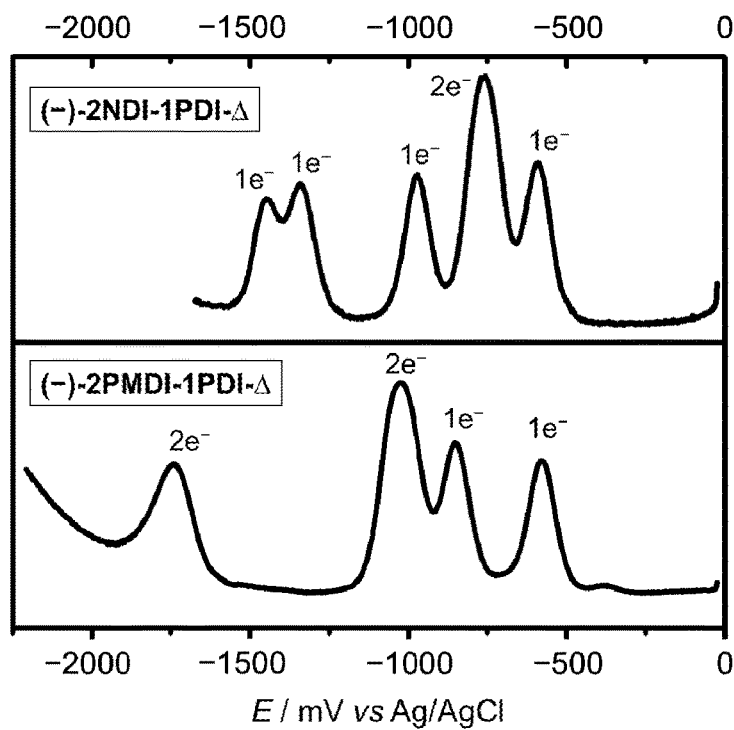

FIG. 7B shows differential pulse voltammetry (DPV) of the rigid isosceles triangles (−)-2PMDI-1PDI-Δ and (−)-2NDI-1PDI-Δ in CH$_2$Cl$_2$ (100 mM TBAPF$_6$, 50 mVs$^{-1}$, 298 K).

Figure 7C:
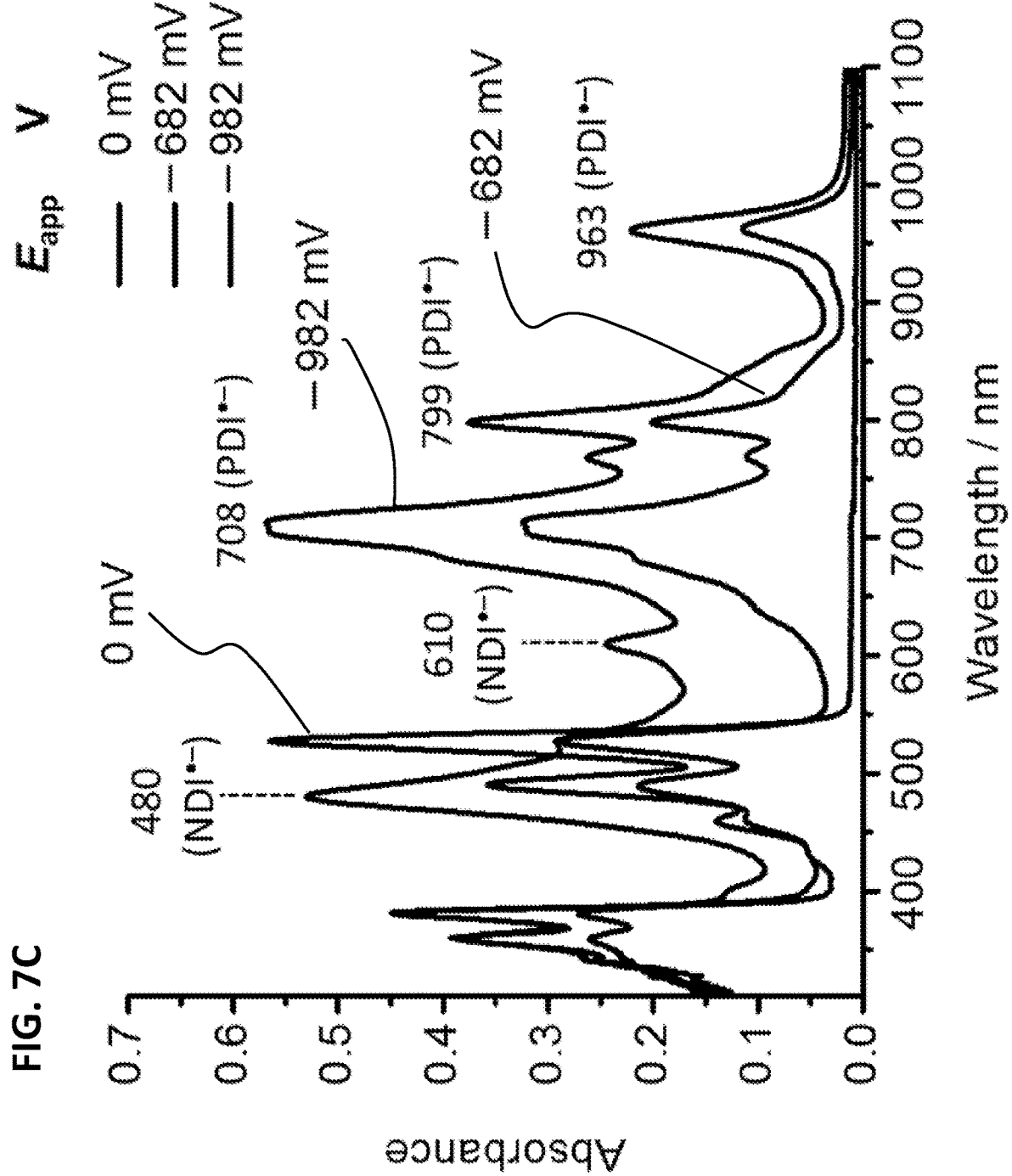

FIG. 7C shows the UV/Vis/NIR spectroelectrochemistry of (−)-2NDI-1PDI-Δ (10 μM in CH$_2$Cl$_2$, 100 mM TBAPF$_6$, 298 K) and the reduced states arising from the electrochemical reduction at different applied potentials (E$_{app}$).

Figure 7D:
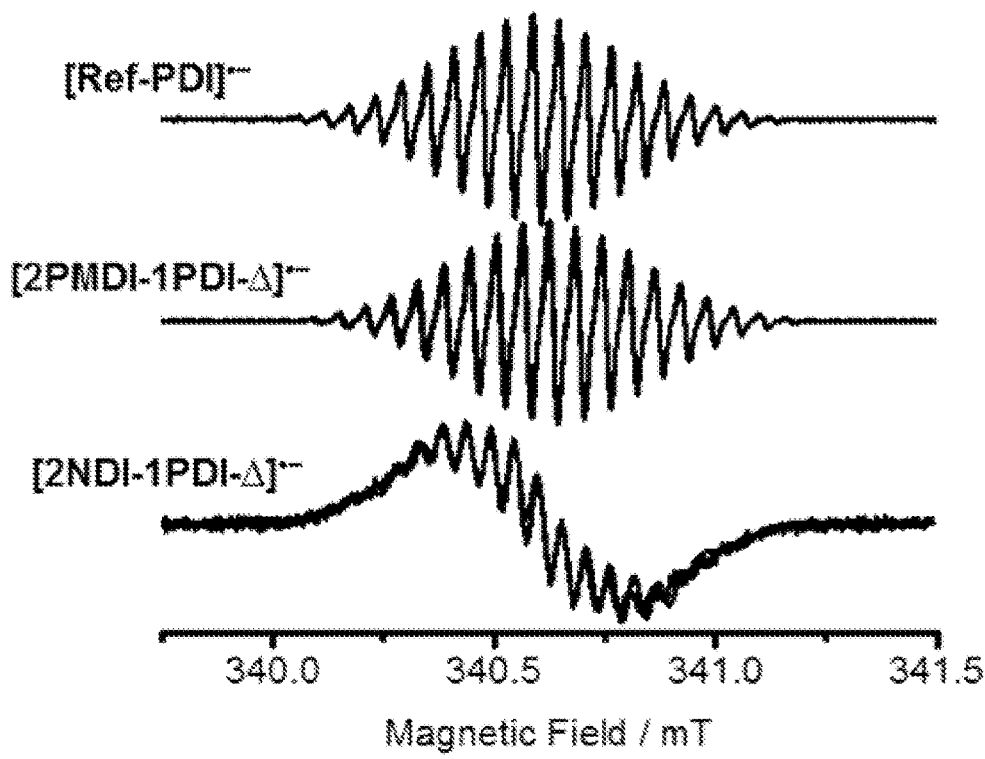
Figure 7E:
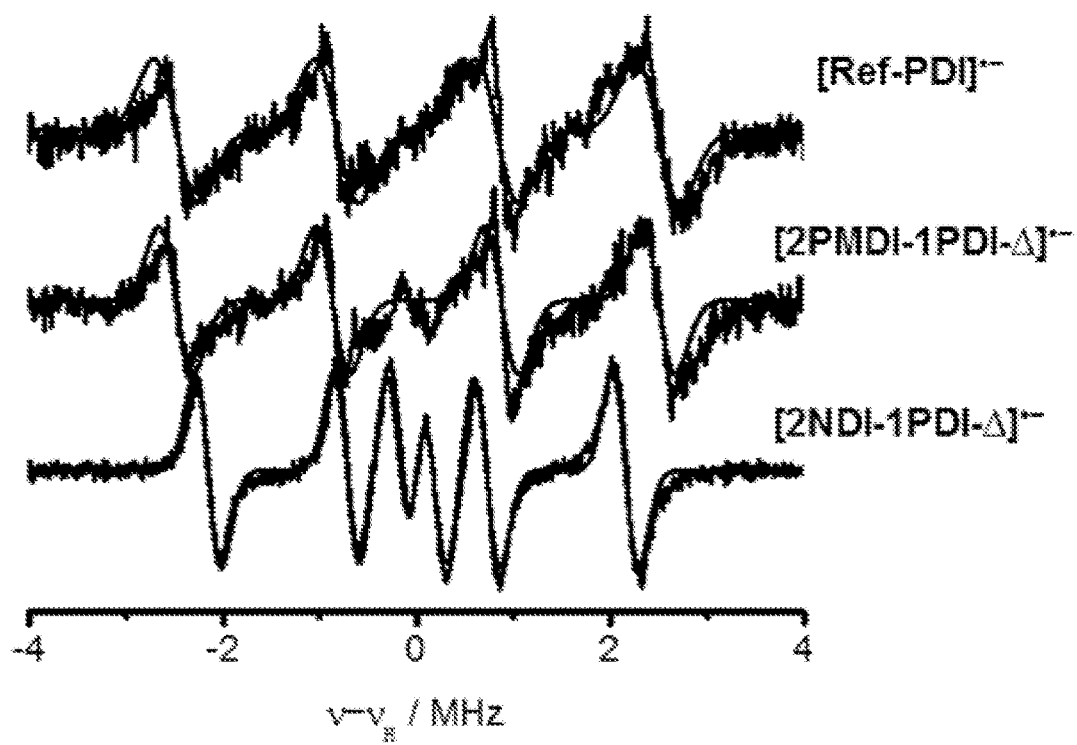

FIGS. 7D and 7E show a CW-EPR (FIG. 7D) and $^1$H ENDOR (FIG. 7E) spectra (0.25 mM in CH$_2$Cl$_2$, 298 K) of [Ref-PDI]$^{·-}$, [(−)-2PMDI-1PDI-Δ]$^{·-}$ and [(−)-2NDI-1PDI-Δ]$^{·-}$, formed by the monoreduction of their corresponding neutral states by adding 1 mol equivalent of cobaltocene. Overlay between the experimental spectra and their simulated spectra.

DETAILED DESCRIPTION OF THE INVENTION

Herein we report on the unique design and synthesis of rigid chiral triangular macrocycles, which may also be referred to chiral isosceles triangles, in which one large poly(peri-naphthalene) (PPN) fluorophore and two smaller pyromellitic diimide (PMDI) or naphthalene diimide (NDI) units are arranged in a rigid cyclic triangular geometry. Single-crystal X-ray diffraction analysis shows that both isosceles triangles form discrete, nearly cofacial PPN-PPN π-dimers in the solid state. The triangles exhibit fluorescence quantum yields of almost unity in solution, and the dimers in the solid state exhibit at least an order of magnitude higher excimer fluorescence yield in comparison with the almost completely quenched fluorescence of a reference PPN. The triangle containing both NDI and PPN subunits shows superior intramolecular energy transfer from the lowest excited singlet state of the NDI to that of the PPN subunit. Cyclic voltammetry suggests that both isosceles triangles exhibit multiple, easily accessible and reversible redox states. As a result, these materials are suitable for the fabrication of molecular optoelectronic and photonic devices.

In the examples that follow, we demonstrate the synthesis of two isosceles triangles—namely, (−)-2PMDI-1PDI-Δ and (−)-2NDI-1PDI-Δ where one large and two small planar π-conjugated aromatic diimides are introduced into rigid chiral cyclic configurations, incorporating three (RR)-trans-1,2-cyclohexanediamine rings. The two PDI-based isosceles triangles have rigid geometries with lower symmetries (C$_2$ point groups), relative to those (D$_3$ point groups) of the equilateral triangles [(−)-3NDI-Δ and (−)-3PMDI-Δ], as evidenced by the expected differences in their $^1$H and $^{13}$C NMR spectra. Their solid-state (super)structures show that geometrically protected PDI fluorophores of the isosceles triangles can only undergo intermolecular PDI-PDI π-π stacking to form dimers because of the absence of any additional long-range non-covalent interactions. This unusual formation and packing arrangement, associated with the molecular rigidity, of the isolated PDI-PDI π-dimers of the isosceles triangles have a significant influence on their photoluminescence properties in the solid state. The fluorescence quantum yield measured in CH$_2$Cl$_2$ relative to that of Ref-PDI (Φ$_f$~1.0) is almost unity (Φ$_f$~1.0) for (−)-2PMDI-1PDI-Δ, while that for (−)-2NDI-1PDI-Δ is only slightly lower (Φ$_f$~0.88). Similarly, all three compounds also exhibited excellent fluorescence quantum yields (Φ$_f$~90-100%) in other organic solvents, such as MeCN and PhMe, except the partially quenched fluorescence of (−)-2NDI-1PDI-Δ (Φ$_{f, PhMe}$=63%) in PhMe which can be attributed to aggregation-caused quenching.

The solid-state photoluminescence quantum yields observed for the excimer states of (−)-2PMDI-1PDI-Δ and (−)-2NDI-1PDI-Δ are about 10 to 40-fold larger compared with that of Ref-PDI. The fluorescence emission spectra also suggest that efficient intramolecular energy transfer occurs between the adjacent NDI and PDI subunits of (−)-2NDI-1PDI-Δ. Such variations in the photophysical properties observed between the monomeric reference compound and the two isosceles triangles form a basis for the rational design of highly efficient fluorescent organic materials for applications in optoelectronic and photonic devices. Also, both (−)-2PMDI-1PDI-Δ and (−)-2NDI-1PDI-Δ are chiral molecules with strong fluorescence emissions, and hence they would be expected to exhibit circularly polarized luminescence (CPL).

Moreover, the electrochemical properties investigated by CV indicate that Ref-PDI can only produce two redox states, while (−)-2PMDI-PDI-Δ and (−)-2NDI-PDI-Δ produce multiple easily accessible redox states, suggesting their potential use as electron accumulation or transport materials. The EPR and ENDOR spectra show that the unpaired electron in (−)-2PMDI-1PDI-Δ is localized on the PDI subunit, while it is partially shared between the NDI and PDI subunits in (−)-2NDI-1PDI-Δ.

It is also possible to prepare higher-order macrocyclic oligomers by introducing various other PPN redox-active functional aromatic diimides, such as anthracene diimides (ADIs), coronene diimides (CDIs), terrylene diimides (TDIs) and quaterrylene diimides (QDIs). A surprising feature of the synthetic strategy presented herein is to make use of smaller aromatic diimides, such as PMDIs and NDIs, as solubilizers so as to incorporate larger insoluble aromatic PPN diimides, without the need for any bulky substituents. Such designed architectures may exhibit multi-functional structural, optical, electronic and magnetic properties associated with their degree of chirality, rigidity, accessible cavities, through-space electron sharing and several readily accessible redox states. This design approach allows for the synthesis of new active materials for organic optoelectronics, energy storage, and energy harvesting devices.

The molecular design and development of organic materials displaying efficient solid-state photoluminescence (PL) is a fundamental prerequisite for the fabrication of high-performance optoelectronic and photonic devices, such as organic light-emitting diodes[1-4] (OLEDs), organic light-emitting field-effect transistors[5,6] (OLEFETs), solid-state lasers,[7,8] fluorescent sensors,[9-11] and security inks.[12,13] Organic fluorophores, exhibiting intense fluorescence in dilute solution, often suffer from aggregation-caused quenching[14] in the solid state because of strong intermolecular interactions involving many molecules, resulting in poor solid-state PL quantum yields. Although it is nearly impossible to predict the fluorescence quantum yield of a particular fluorophore, several strategies[15-25] have been proposed in the literature in order to enhance fluorescence efficiency, in particular, in the solid state. These strategies include (i) the introduction of bulky substituents into the parent fluorophore to prevent the detrimental intermolecular interactions between the neighboring fluorophores,[15-18] (ii) the restriction of intramolecular rotations of the fluorophore side groups to minimize radiationless deactivation, (iii) the enforcement of a conformational change from a twisted conformation in solution to a planar one in the solid state,[19] (iv) the formation of J-type fluorophore aggregates,[20] and (v) the enhancement of intramolecular charge transfer (ICT) character within donor-π-acceptor systems.[21,22] Also, the development of chiral emissive organic molecules exhibiting circularly polarized luminescence (CPL) has attracted increasing attention in the recent past. Despite these significant advances, the development of novel molecular designs for rigid covalent chiral organic materials with multiple, readily available reversible redox states, exhibiting photoluminescence with high quantum yields both in solution and solid state, remains a formidable challenge.

Rigid Macrocycles

As used herein, a "rigid macrocycle" is a cyclic macromolecule or a macromolecular cyclic portion of a molecule that is constrained against large-amplitude conformational rearrangement around the cyclic portion of the molecule. The rigid macrocycle may be composed of one or more subunits arranged in a cyclic manner. In some embodiments, the rigid macrocycle is composed of two alternating subunits arranged in a cyclic manner. Suitably the rigid macrocycle comprises two alternating subunits arranged in a cyclic manner where the first alternating subunit is a redox-active subunit and the second alternating subunit is a linking subunit. The rigid macrocycles disclosed herein may have three redox-active subunits and three linking subunits.

The rigid macrocycles disclosed herein may comprise a first redox-active subunit and a second redox-active subunit, wherein the first redox-active unit and the second redox-active unit are different subunits. The macrocycles may further comprise a third redox-active subunit. In some embodiments, the second redox-active subunit and the third redox-active subunit are the same subunits. In particular embodiments, the macrocycle comprises a first, a second, and a third redox-active subunit where the second and third are the same subunit but the first is different from either the second or third subunit. Macrocycles of this type may have $C_2$ symmetry.

The first and/or second redox-active subunit may be a π-conjugated aromatic diimide. In certain embodiments, the first and/or second redox-active subunit is a pyromellitic diimide-based (PMDI) subunit, a naphthalene diimide-based (NDI) subunit, or a poly(peri-naphthalene) diimide-based (PPNDI) subunit. Suitably, the rigid macrocycle may comprise one PPNDI subunit and two NDI subunits or one PPNDI subunit and two PMDI subunits.

The PPNDI subunit may be derived from a poly(peri-naphthalene)tetracarboxylic acid dianhydride (PPNDA) of formula

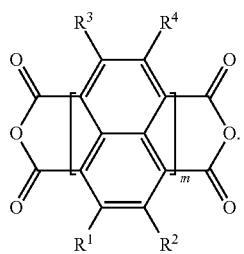

Each of $R^1$, $R^2$, $R^3$, and $R^4$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group and m is greater than or equal to 2 and less than or equal to 10. In particular embodiments, each of $R^1$, $R^2$, $R^3$, and $R^4$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_1$-$C_4$ hydroxyl moiety, a $C_1$-$C_4$ alkoxy moiety, a $C_1$-$C_6$ phenoxy moiety, a $C_1$-$C_4$ carbonyl moiety, a $C_1$-$C_4$ cyano moiety, or a $C_1$-$C_4$ sulfate moiety.

In certain embodiments, $R^1$ and $R^2$ and/or $R^3$ and $R^4$ of adjacent peri-naphthalenes may together form a bivalent saturated or unsaturated aliphatic radical. For example, $R^1$ and $R^2$ together and/or $R^3$ and $R^4$ together may comprise —CH$_2$CH$_2$— or —CHCH—.

Suitably m may be equal to 2, 3, 4, 5, 6, 7, 8, 9, or 10. When m is 2, the PPNDA may be a PDA or coronene tetracarboxylic acid dianhydride (CDA). When m is 3, the PPNDA may be a terrylene tetracarboxylic acid dianhydride (TDA). When m is 4, the PPNDA may be a quarterrylene tetracarboxylic acid dianhydride (QDA).

Suitably, PPNDI subunits incorporated into a rigid macrocycle may comprise a poly(peri-naphthalene) diimide diradical of formula

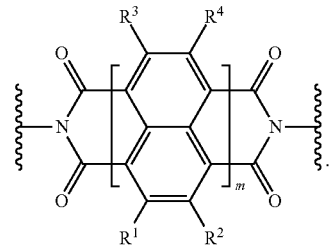

Each of $R^1$, $R^2$, $R^3$, and $R^4$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group m is greater than or equal to 2 and less than or equal to 10. In particular embodiments, each of $R^1$, $R^2$, $R^3$, $R^4$, $R^5$, $R^6$, $R^7$, and $R^8$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_1$-$C_4$ hydroxyl moiety, a $C_1$-$C_4$ alkoxy moiety, a $C_1$-$C_6$ phenoxy moiety, a $C_1$-$C_4$ carbonyl moiety, a $C_1$-$C_4$ cyano moiety, or a $C_1$-$C_4$ sulfate moiety. Suitably m may be equal to 2, 3, 4, 5, 6, 7, 8, 9, or 10. When m is 2, the PPNDI may be a PDI or CDI. When m is 3, the PPNDI may be a TDI. When m is 4, the PPNDI may be a QDI.

Suitably, the rigid macrocycle may comprise one PDI subunit and two NDI subunits or one PDI subunit and two PMDI subunits. The PDI subunit may be derived from a perylenetetracarboxylic acid dianhydride (PDA) of Formula (1).

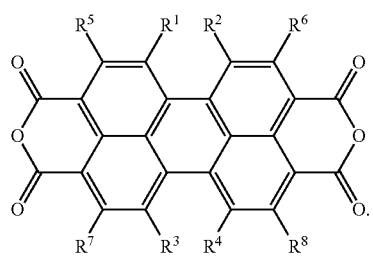

Each of $R^1$, $R^2$, $R^3$, $R^4$, $R^5$, $R^6$, $R^7$, and $R^8$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. In particular embodiments, each of $R^1$, $R^2$, $R^3$, $R^4$, $R^5$, $R^6$, $R^7$, and $R^8$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_1$-$C_4$ hydroxyl moiety, a $C_1$-$C_4$ alkoxy moiety, a $C_1$-$C_6$ phenoxy moiety, a $C_1$-$C_4$ carbonyl moiety, a $C_1$-$C_4$ cyano moiety, or a $C_1$-$C_4$ sulfate moiety.

In some embodiments, the PDI subunit is derived from a PDA of Formula (1a):

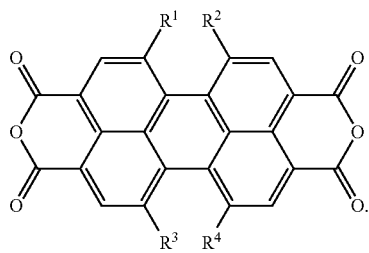

Each of $R^1$, $R^2$, $R^3$, and $R^4$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. In particular embodiments, each of $R^1$, $R^2$, $R^3$, and $R^4$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl moiety, a $C_1$-$C_4$ cyano moiety, or a $C_1$-$C_4$ sulfate moiety.

Suitably, PDI subunits incorporated into a rigid macrocycle may comprise a perylene diimide diradical of formula

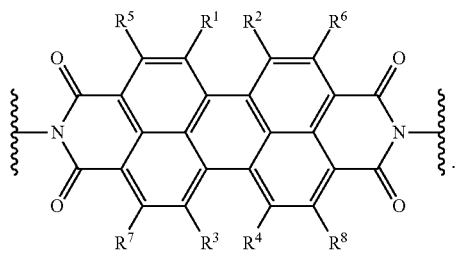

Each of $R^1$, $R^2$, $R^3$, $R^4$, $R^5$, $R^6$, $R^7$, and $R^8$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. In particular embodiments, each of $R^1$, $R^2$, $R^3$, $R^4$, $R^5$, $R^6$, $R^7$, and $R^8$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_1$-$C_4$ hydroxyl moiety, a $C_1$-$C_4$ alkoxy moiety, a $C_1$-$C_6$ phenoxy moiety, a $C_1$-$C_4$ carbonyl moiety, a $C_1$-$C_4$ cyano moiety, or a $C_1$-$C_4$ sulfate moiety.

In some embodiments, PDI subunits incorporated into a rigid macrocycle may comprise a perylene diimide diradical of formula

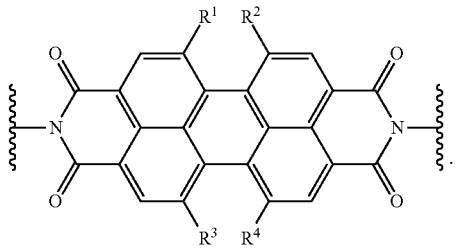

Each of $R^1$, $R^2$, $R^3$, and $R^4$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. In particular embodiments, each of $R^1$, $R^2$, $R^3$, and $R^4$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl moiety, a $C_1$-$C_4$ cyano moiety, or a $C_1$-$C_4$ sulfate moiety.

In the Examples that follow, macrocycles prepared from the compound of Formula (1) or (1a) where each of the substituents $R^1$-$R^8$ or $R^1$-$R^4$, respectively, are selected from hydrogen and the use thereof for fluorescence and photoluminescence is demonstrated. A person of skill in the art is capable of preparing derivatives of the macrocycles disclosed in the Examples by substituting those particular PDI subunits with any of the other PDI subunits disclosed herein.

The NDI subunit may be derived from a naphthalenetetracarboxylic dianhydride (NDA) of Formula (2):

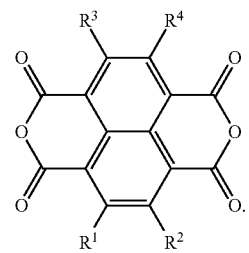

Each of $R^1$, $R^2$, $R^3$, and $R^4$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. In particular embodiments, each of $R^1$, $R^2$, $R^3$, and $R^4$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl moiety, a $C_1$-$C_4$ cyano moiety, or a $C_1$-$C_4$ sulfate moiety.

Suitably, the NDI subunits incorporated into a rigid macrocycle may comprise a diradical of formula

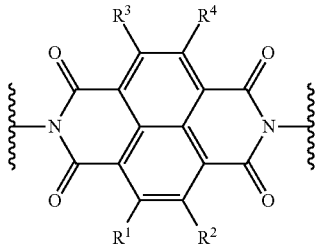

Each of $R^1$, $R^2$, $R^3$, and $R^4$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other functional group. In particular embodiments, each of $R^1$, $R^2$, $R^3$, and $R^4$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl moiety, a $C_1$-$C_4$ cyano moiety, or a $C_1$-$C_4$ sulfate moiety.

In the Examples that follow, macrocycles prepared from the compound of Formula (2) where each of $R^1$, $R^2$, $R^3$, and $R^4$ are hydrogen and the use thereof for fluorescence and photoluminescence is demonstrated. A person of skill in the art is capable of preparing derivatives of the macrocycles disclosed in the Examples by substituting those particular NDI subunits with any of the other NDI subunits disclosed herein.

The PMDI subunit may be derived from a pyromellitic dianhydride (PMDA) of Formula (3):

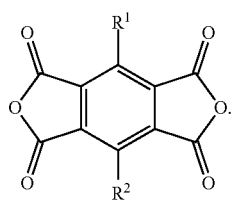

Each of $R^1$ and $R^2$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other suitable functional group. In particular embodiments, each of $R^1$, $R^2$, $R^3$, and $R^4$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl, a $C_1$-$C_4$ cyano moiety, or a $C_1$-$C_4$ sulfate moiety.

Suitably, the PMDI subunits incorporated into a rigid macrocycle may comprise a diradical of formula

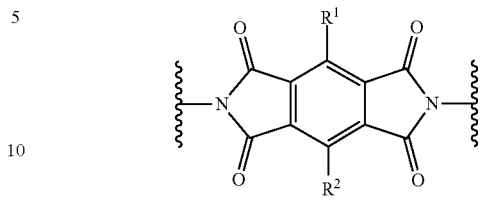

Each of $R^1$ and $R^2$ may be, independently, hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other suitable functional group. In particular embodiments, each of $R^1$, $R^2$, $R^3$, and $R^4$ may be, independently, hydrogen, fluorine, chlorine, bromine, iodine, a $C_1$-$C_4$ alkyl moiety, a $C_1$-$C_4$ alkenyl moiety, a $C_1$-$C_4$ alkynyl moiety, a $C_0$-$C_4$ hydroxyl moiety, a $C_1$-$C_4$ alkoxy moiety, a $C_1$-$C_4$ phenoxy moiety, a $C_1$-$C_4$ carbonyl, a $C_1$-$C_4$ cyano moiety, or a $C_1$-$C_4$ sulfate moiety.

In the Examples that follow, macrocycles prepared from the compound of Formula (3) where each of $R^1$ and $R^2$ is hydrogen and the use thereof for fluorescence and photoluminescence is demonstrated. A person of skill in the art is capable of preparing derivatives of the macrocycles disclosed in the Examples by substituting those particular PMDI subunits with any of the other PMDI subunits disclosed herein.

The macrocycles further comprise a linking subunit that links one or more combinations of the first redox-active subunit and the second redox-active subunit, the second redox-active subunit, and the third redox-active subunit, or the third redox-active subunit and the first redox-active subunit. A macrocycle may have three identical linking subunits in some embodiments, but may also have two different linking subunits or three different linking subunits in other embodiments. The linking subunit may be a cycloalkyl subunit, but need not be. In some embodiments, the linking subunit is chiral.

In particular embodiments, the linking subunits are chiral cycloalkyl subunits. The cycloalkyl subunits may have two chiral centers at adjacent carbon positions. In particular embodiments, the linking subunit is an (RR)-1,2-trans-cycloalkyl subunit or an (SS)-1,2-trans-cycloalkyl subunit. In particular embodiments, the cycloalkyl subunit is a $C_4$-$C_8$ cycloalkyl subunit. The cycloalkyl subunit may be a substituted or unsubstituted cycloalkyl subunit.

Substituents may include hydrocarbon moieties, halogen moieties, oxygen-containing moieties, nitrogen-containing moieties, sulfur containing moieties, or combinations thereof. In certain embodiments, substituents may be $C_{1-6}$ alkyl moieties, $C_{1-6}$ alkenyl moieties, $C_{1-6}$ alkynyl moieties, phenyl moieties, halo moieties, $C_{0-6}$ hydroxyl moieties, $C_{1-6}$ ether moieties, $C_{1-6}$ carbonyl moieties, $C_{1-6}$ aldehyde moieties, $C_{1-6}$ carboxyl moieties, $C_{1-6}$ ester moieties, or combinations thereof.

In the Examples that follow, the macrocycles are prepared from (RR)-1,2-trans-cyclohexyl subunits, but other linking subunits may also be used. A person of skill in the art is capable of preparing derivatives of the macrocycles disclosed in the Examples by substituting those particular from (RR)-1,2-trans-cyclohexyl subunits with any of the other linking subunits disclosed herein.

In some embodiments, the macrocycle comprises a compound of Formula (4)

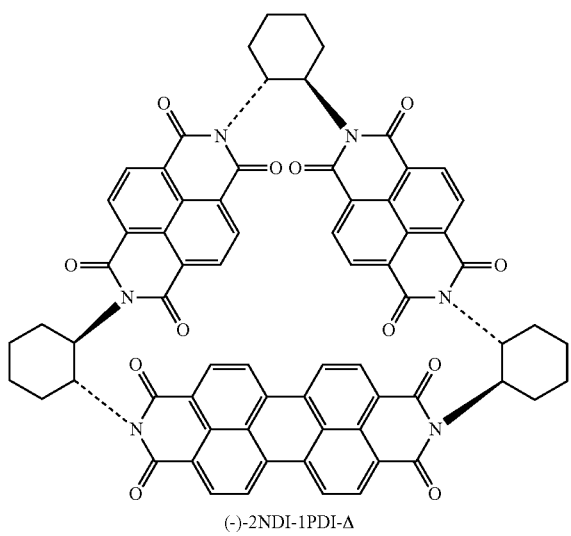

(-)-2NDI-1PDI-Δ or a compound of Formula (5)

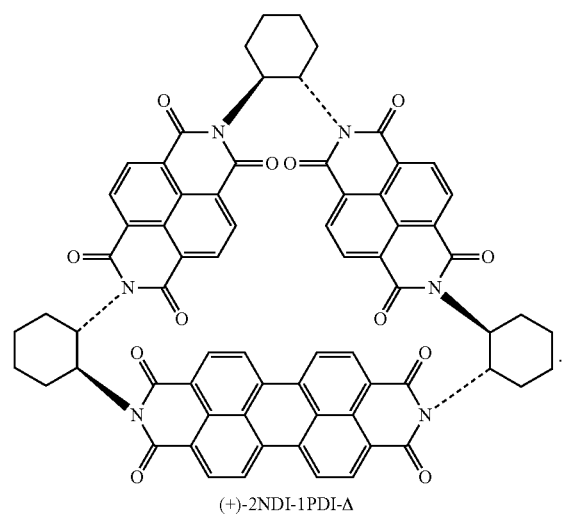

(+)-2NDI-1PDI-Δ

Compounds of Formulas (4) or (5) may be prepared by the stepwise cyclocondensation of two NDA and one PDA compounds resulting in a rigid macrocycle comprising two NDI subunits and one PDI subunit. The compound of Formulas (4) and (5) differs in the choice of the linking subunit. One uses (RR)-1,2-trans-cyclohexyl subunits and the other uses an (SS)-1,2-trans-cyclohexyl subunits. Derivatives of the compounds of Formulas (4) or (5) may be prepared by replacing a PDI subunit with any of the PDI redox-active subunits disclosed above, the NDI redox-active subunit with any of the NDI redox-active subunits disclosed above, replacing a linking subunit with any of the linking subunits disclosed above, or any combination thereof. Derivatives of the compounds of Formulas (4) or (5) may be a substituted derivative, where the substituent may be an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other suitable functional group. The compound of Formula (4) may be referred to as (-)-2NDI-1PDI-Δ and the compound of Formula (5) may be referred to as (+)-2NDI-1PDI-Δ.

In some embodiments, the macrocycle comprises a compound of Formula (6)

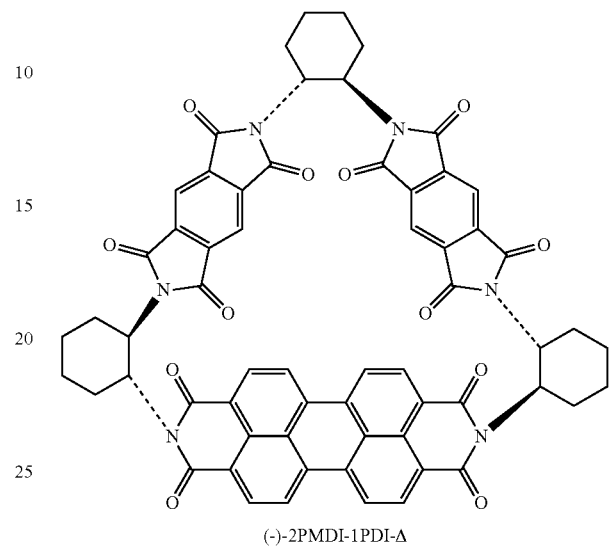

(-)-2PMDI-1PDI-Δ or a compound of Formula (7)

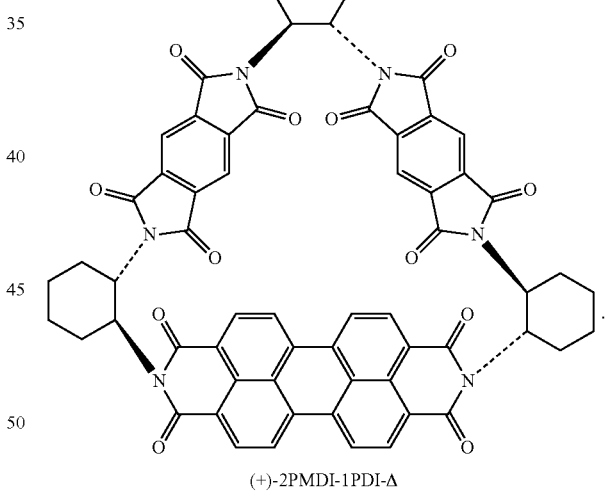

(+)-2PMDI-1PDI-Δ

Compounds of Formulas (6) or (7) may be prepared by the stepwise cyclocondensation of two PMDA and one PDA compounds resulting in a rigid macrocycle comprising two PMDI subunits and one PDI subunit. The compound of Formulas (4) and (5) differs in the choice of the linking subunit. One uses (RR)-1,2-trans-cyclohexyl subunits and the other uses an (SS)-1,2-trans-cyclohexyl subunits. Derivatives of the compounds of Formulas (4) or (5) may be prepared by replacing a PDI subunit with any of the PDI redox-active subunits disclosed above, the PMDI redox-active subunit with any of the PMDI redox-active subunits disclosed above, replacing a linking subunit with any of the linking subunits disclosed above, or any combination thereof. Derivatives of the compounds of Formulas (4) or (5) may be a substituted derivative, where the substituent may be an alkyl moiety, an alkenyl moiety, an alkynyl moiety, a hydroxyl moiety, an alkoxy moiety, a phenoxy moiety, a carbonyl moiety, a cyanide moiety, a sulfate moiety, or other suitable functional group. The compound of Formula (6) may be referred to as (−)-2PMDI-1PDI-Δ and the compound of Formula (7) may be referred to as (+)-2PMDI-1PDI-Δ.

Photoluminescent Materials

The rigid macrocycles described herein may be used to prepare photoluminescent materials. Suitably the photoluminescent material comprises any of the rigid macrocycles described herein. In some embodiments, the materials comprise a crystalline composition comprising a plurality of the rigid macrocycles. As explained further in the examples, the plurality of rigid macrocycles may be arranged such that dimers are formed by π-π stacking interactions between PDI subunits of adjacent macrocycles in the dimer. Dimer formation allows the PDI subunits to be positioned with a separation of about 3.3 Å to about 3.5 Å for excimer formation and reduction in aggregation-caused quenching. As a result, the photoluminescent materials comprising the rigid macrocycles are high-efficient photoluminescent organic materials.

A photoluminescent material is a material capable of emitting photons after the absorption of photons. Photoluminescence is one form of stimulated light emission initiated by photoexcitation. Photoluminescence processes can be classified by various parameters such as the energy of the exciting photon with respect to the emission. The materials may be excited with electromagnetic radiation having a wavelength in the near-ultraviolet or visible range. Suitably, the material may be excited with electromagnetic radiation having a wavelength of about 200 nm to about 700 nm, including any range therebetween. The materials may also emit electromagnetic radiation having a wavelength in the visible or near-infrared range. Suitably, the material may emit electromagnetic radiation having a wavelength of about 350 nm to about 800 nm, about 500 nm to about 800 nm, or about 500 nm to about 750 nm. In some embodiments, the material emits electromagnetic radiation having a $\lambda_{max}$ wavelength of about 500 nm to about 715 nm, where $\lambda_{max}$ is the wavelength of most intense emission. Suitably, the material may have a $\lambda_{max}$ wavelength of about 500 nm to about 570 nm, about 565 nm to about 640 nm, about 615 nm to about 685 nm, or about 635 to about 715 nm.

The photoluminescent materials described herein have high quantum yields. A molecule's efficiency to photoluminesce is described by its quantum yield and is defined as the ratio of the number of photons absorbed to the number of photons emitted by a sample. In some embodiments, the quantum yield may be determined in reference to a standard. An exemplary standard for comparison to the photoluminescence materials described herein is N,N'-dicyclohexylperylene-3,4:9,10-tetracarboxylic acid diimide. In other embodiments, the quantum yield may be the absolute quantum yield. The absolute method directly obtains the quantum yield by detecting all sample fluorescence through the use of an integrating sphere. Suitably the quantum yield is at least 0.50 and in some cases greater than 0.60, 0.65, 0.70, 0.75, 0.80, 0.85, 0.90, 0.95, 0.96, 0.97, 0.98, or 0.99.

Perylene diimide (PDI) derivatives have been investigated as model organic fluorophores and n-type semiconductors because of their high fluorescence quantum yields in addition to their excellent chemical, thermal and photochemical stabilities.[26-28] The unique redox-active characteristics associated with the high electron mobilities of PDIs renders them attractive candidates[29,30] for applications in a wide variety of fields, such as OLEDs,[31] OFETs[32,33] and organic photovoltaics[34-36] (OPVs). Selective substitution at the core positions of the PDI fluorophores has been well-established[37-39] as a means of improving their properties. The fluorescence of PDIs is quenched in the solid state on account of their planarity which favors the aggregation by dint of consecutive π-π interactions between the neighboring fluorophores. Recently, Würthner and co-workers have shown that the introduction of bulky substituents onto the PDI fluorophore is an effective strategy to favor the formation of discrete π-π dimers[40,41] which prohibits further PDI aggregation and achieves somewhat rigid and planar PDI fluorophores[42,43] in the solid state, giving rise to variable structural and optical properties, depending on the nature of the substituent. In particular, substitution of 2,6-diphenylphenoxy substituents at the 1,7-bay positions of the PDI fluorophore led to isolated monomeric PDI units in the crystalline state, resulting in a 37% fluorescence quantum yield from the PDI lowest excited singlet state, which is the highest solid-state fluorescence quantum yield for PDI derivatives reported to date.[43] It is noteworthy that the conformational flexibility offered by the core-substituents on the PDI fluorophores in most cases, however, leads to inevitable intramolecular rotations or twists, which presumably reduce their solid-state fluorescence quantum yields as a result of enhanced nonradiative decay.[44,45]

A rigid equilateral triangle (−)-3NDI-Δ, comprising three equivalent naphthalene diimide (NDI) units, gives rise to six individually accessible one-electron redox states. Extensive characterization of the symmetric (−)-3NDI-Δ by single-crystal X-ray diffraction revealed[50,53] its distinct packing arrangement in the solid state, depending on the nature of its encapsulated guest[49] and solvent[50] molecules, as well as its chirality[53] and electronic state.[55,58,59] The assembly of (−)-3NDI-Δ resulted in the formation of one-dimensional (i) helical superstructures driven by anion-π induced face-to-face π-π stacking of two of the NDI units of (−)-3NDI-Δ in the presence of an encapsulated linear $I_3^−$ anion in $CHCl_3$, as well as (ii) finite and infinite supramolecular nanotubes in the presence of encapsulated dihaloethane and -ethene (DXE) driven by the columnar stacking of (−)-3NDI-Δ with cooperative weak [C—H . . . O] interactions along the direction of [X . . . X]-bonded solvent chains. On the other hand, the monoradical anion 3NDI.$^+$ assembled into a $K_4$ structure[58] driven by the intermolecular face-to-face π-π stacking interactions between the NDI radical anions in the solid state, while the triradical trianion $3NDI^{3(−)}$ strongly associated with three cobaltocenium ($CoCp_2^+$) cations into infinite one-dimensional channels[55] by dint of electrostatic and hydrogen bonding interactions.

Rigid isosceles triangles[54] [(−)-2PMDI-1NDI-Δ and (−)-2NDI-1PMDI-Δ] are obtained by replacing one of the redox-active units with another in the case of the equilateral triangles [(−)-3PMDI-Δ[60] and (−)-3NDI-Δ] without disrupting the triangular geometry. Unlike the equilateral triangles, these isosceles triangles lack the ability to form extended 1D tubular (super)structures but give rise to 2D layer-like (super)structures in the solid state.

Based on the knowledge gained from the intramolecular cyclical through-space electron sharing properties and the distinct solid-state packing arrangements associated with all of the PMDI- and NDI-based trimers, we decided to include the PDI derivatives in these cyclic systems in order to achieve efficient optoelectronic and photonic properties in the realm of small-molecule organic materials. Considering the synthetic challenges associated with the poor solubility of core- or bay-unsubstituted PDI fluorophores, we recently reported[51] the one-pot synthesis of a molecular triangle composed of three bulky 1,6,7,12-tetra(phenoxy)-substituted PDIs. Unlike the previously reported rigid molecular triangles to date, this PDI-based equilateral triangle containing as many as 12 flexible phenoxy substituents could neither be crystallized nor encapsulate suitable guest molecules. Surprisingly, we found that the fluorescence emission of this PDI triangle is quenched, even in dilute $CH_2Cl_2$ with a fluorescence quantum yield ($\Phi_f$) of about 0.2%, as a result of highly efficient nonradiative decay by means of an ultrafast photoinduced intramolecular symmetry-breaking charge separation process. In contrast with the six distinct one-electron redox waves observed for the PMDI- or NDI-based equilateral triangles, cyclic voltammetry reveals only two distinct reversible reduction waves, involving a total of six electrons for this PDI triangle. Therefore, we anticipated that the design and synthesis of rigid core- or bay-unsubstituted PDI-based isosceles, rather than equilateral, triangles would be of particular value in an attempt to improve the structural, optical, electronic and magnetic properties of the diimide-based triangles. These unique rigid chiral cyclic systems may serve as model platforms for the investigation of (i) the through-space electron communication as well as of (ii) the solid-state packing arrangements with respect to the competitive intermolecular π-π stacking interactions between the non-identical redox-active units, with different dimensions, present in confined environments.

Herein, we report the design, synthesis and the full characterization of two chiral rigid N-substituted PDI-based isosceles triangles—namely, (−)-2PMDI-1PDI-Δ and (−)-2NDI-1PDI-Δ—in both solution and solid states, and compare the results with those of the related monomeric reference compounds, Ref-PMDI,[61] Ref-NDI,[62] and Ref-PDI.[63] The properties of the isosceles triangles are characterized by a combination of spectroscopies [steady-state and transient absorption, fluorescence, circular dichroism (CD), electron paramagnetic resonance (EPR), electron-nuclear double resonance (ENDOR)], variable temperature powder X-ray diffraction (VT-PXRD), single-crystal X-ray diffraction (XRD), thin film XRD, cyclic voltammetry (CV) and computational modeling techniques. XRD Analysis shows that the rigid triangular geometry of the macrocycles suppresses the conventional global π-π stacking into discrete nearly cofacial PDI-PDI π-dimers. The optical properties of the compounds have been investigated by steady-state absorption, transient absorption, and fluorescence spectroscopies both in solution and solid state. Although the fluorescence quantum yields of the isosceles triangles are almost unity in solution, they exhibit very weak excimer emission in the solid state when compared to the almost completely quenched photoluminescence of the monomeric Ref-PDI. The electronic properties investigated by CV suggest that the isosceles triangles exhibit multiple reversible redox states implicating a total of up to six electrons. The magnetic properties studied by EPR and ENDOR spectroscopies, supported by density functional theory calculations, indicate that the behavior of the unpaired electron on the singly reduced PDI subunit is indeed dependent on the nature of the adjacent PMDI/NDI subunits present within the isosceles triangles.

Syntheses of PDI-Based Isosceles Triangles

The redox-active macrocycles may be prepared by stepwise cyclocondensation of a first reagent and a second reagent. The first reagent comprises a PPNDA subunit and the second reagent comprises two redox-active subunits and three linking subunits.

The PPNDA subunit may be any of the PPNDA subunits described herein. Suitably the first reaction is a PPNDA of formula

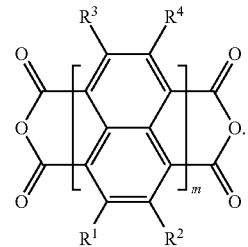

Reacting the PPNDA with an amino-substituted linking subunit results in a PPNDI subunit comprising a diradical of formula

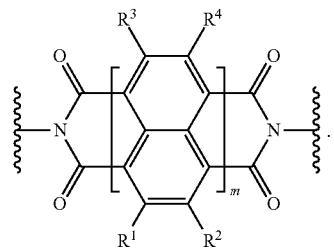

Suitably the first reagent is a PDA of Formula (1):

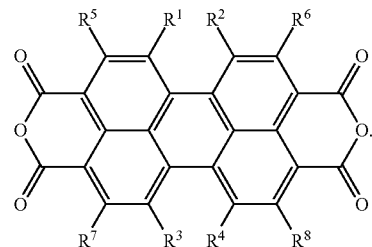

In some embodiments, the first reagent is prepared by reacting a PDA of Formula (1a):

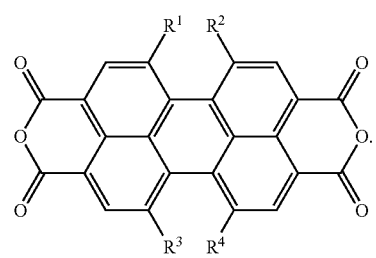

In some embodiments, the second reagent comprises two NDI subunits. The NDI subunits may be any of the NDI subunits described herein. Suitably the second reagent is prepared by reacting an NDA of Formula (2):

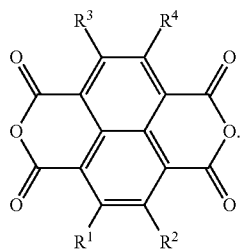

Reacting the NDA of Formula (2) with amino-substituted linking subunits results in an NDI subunit comprising a diradical of formula

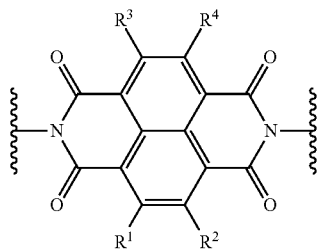

In particular embodiments, the second reagent comprises a compound of Formula (8)

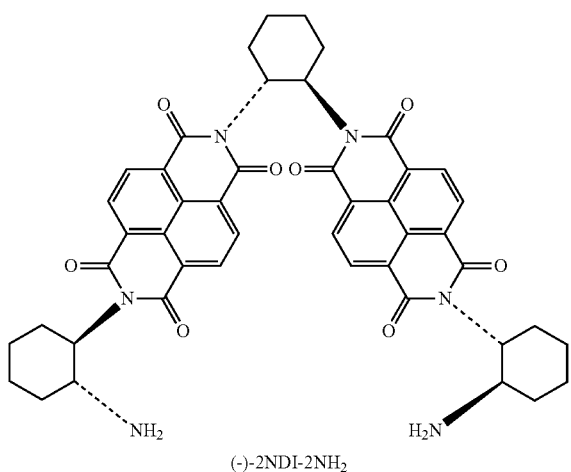

(−)-2NDI-2NH$_2$ or a compound of Formula (9)

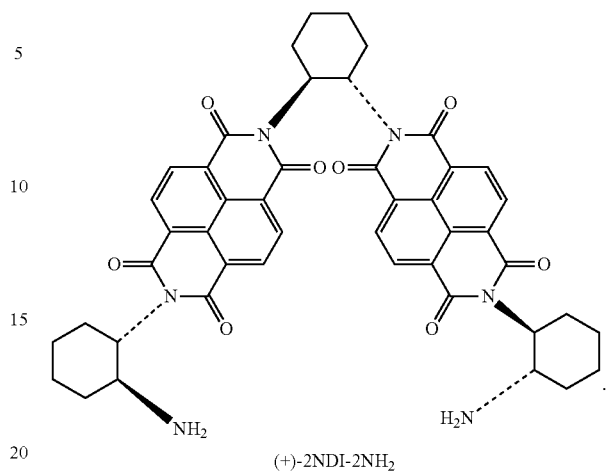

(+)-2NDI-2NH$_2$

Derivatives of either of Formulas (8) or (9) may also be used to prepare the macrocycle. The derivatives may comprise two of any of the NDI subunits of Formula (2) described above. In some cases, the NDI subunits are the same. In other cases, the NDI subunits may be different. Compounds of Formulas (8) or (9), as well as derivatives of either Formulas (8) or (9), may be cyclocondensed with any of the PPNDA compounds described herein.

In some embodiments, the second reagent comprises two PMDI subunits. The PMDI subunits may be any of the PMDI subunits described herein. Suitably the second reagent is prepared by reacting a PMDA of Formula (3):

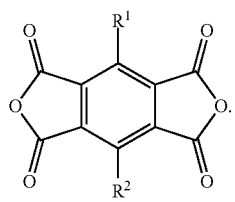

Reacting the PMDA of Formula (3) with amino-substituted linking subunits results in a PMDI subunit comprising a diradical of formula

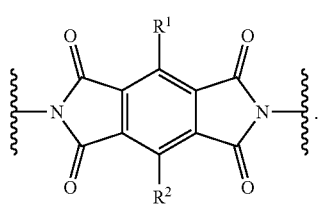

In particular embodiments, the second reagent comprises a compound of Formula (10)

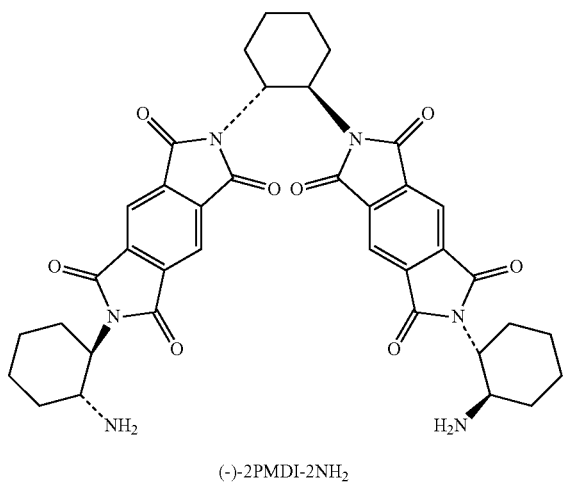

(−)-2PMDI-2NH$_2$ or a compound of Formula (11)

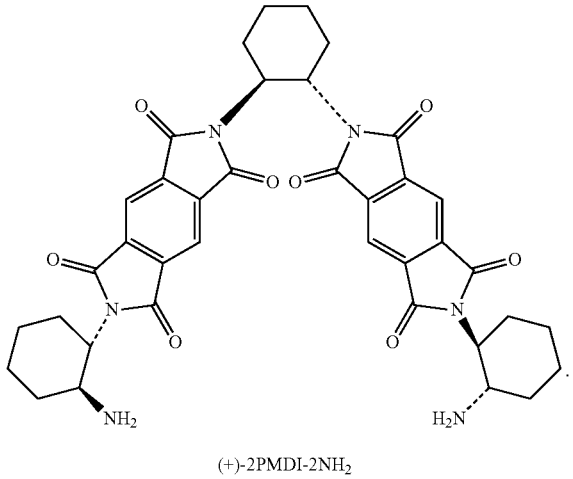

(+)-2PMDI-2NH$_2$

Derivatives of either of Formulas (10) or (11) may also be used to prepare the macrocycle. The derivatives may comprise two of any of the PMDI subunits of Formula (3) described above. In some cases, the PMDI subunits are the same. In other cases, the PMDI subunits may be different. Compounds of Formulas (10) or (11), as well as derivatives of either Formulas (10) or (11), may be cyclocondensed with any of the PPNDI subunits described herein.

Figure 1A:
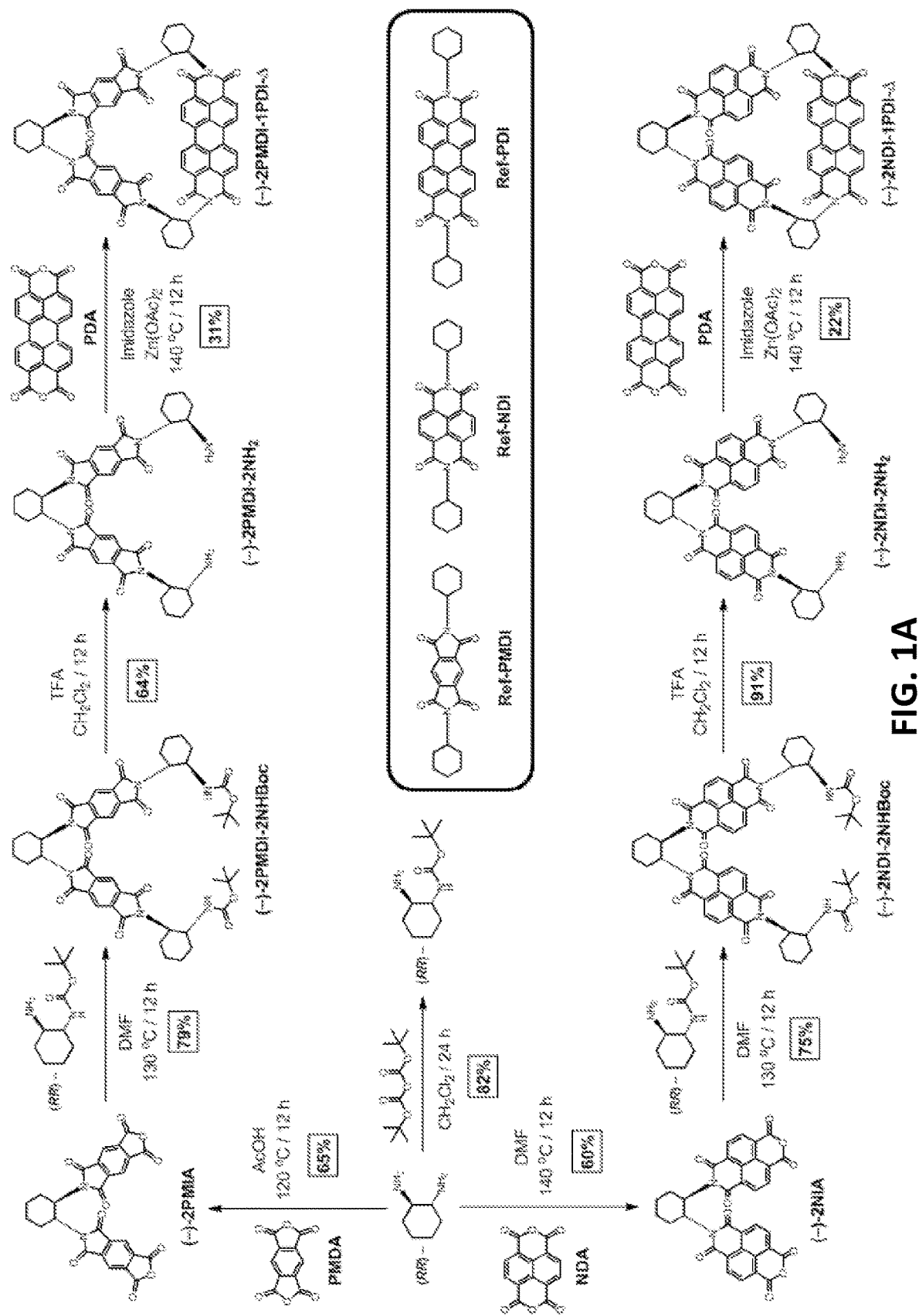
FIG. 1A illustrates the synthesis of chiral rigid PDI-based isosceles triangles by stepwise preparation of the isosceles triangles [(−)-2PMDI-1PDI-Δ and (−)-2NDI-1PDI-Δ] from (RR)-trans-1,2-cyclohexanediamine, pyromellitic dianhydride (PMDA), naphthalenetetracarboxylic dianhydride (NDA) and perylenetetracarboxylic dianhydride (PDA). The inset shows the structural formulas of the monomeric reference compounds (Ref-PMDI, Ref-NDI, and Ref-PDI). The aromatic PMDI, NDI and PDI subunits within the molecular triangles are shown in magenta, blue and green, respectively.

As demonstrated in the Examples, two rigid PDI-based isosceles triangles were synthesized (FIG. 1A and Scheme 1) by stepwise condensations between commercially available (RR)-trans-1,2-cyclohexanediamine and three different dianhydride derivatives—namely, pyromellitic dianhydride (PMDA), naphthalenetetracarboxylic dianhydride (NDA) and perylenetetracarboxylic dianhydride (PDA). Starting with the condensation between (RR)-trans-1,2-cyclohexanediamine and an excess of either PMDA in acetic acid at 120° C. or NDA in DMF at 140° C. gave the corresponding monoimide-monoanhydride dimers—namely, (−)-2PMIA[54] and (−)-2NIA[56]—as previously reported by us. The subsequent condensation of the dimers with an excess of mono-N-Boc-(RR)-trans-1,2-cyclohexanediamine in DMF at 130° C. afforded their carbamate derivatives, (−)-2PMDI-2NH-Boc and (−)-2NDI-2NHBoc, in good yields. The removal of the Boc groups using trifluoroacetic acid (TFA) gave the corresponding diamines, (−)-2PMDI-2NH$_2$ and (−)-2NDI-2NH$_2$. The cyclocondensation of the diamines, (−)-2PMDI-2NH$_2$ and (−)-2NDI-2NH$_2$, with 1 mol equivalent of PDA in the presence of zinc acetate in molten imidazole at 140° C. afforded (FIG. 1A) the desired highly rigid isosceles triangles (−)-2PMDI-1PDI-Δ and (−)-2NDI-1PDI-Δ in 31 and 22% yields, respectively.

SCHEME 1.
Synthesis of PDI-based isosceles triangles
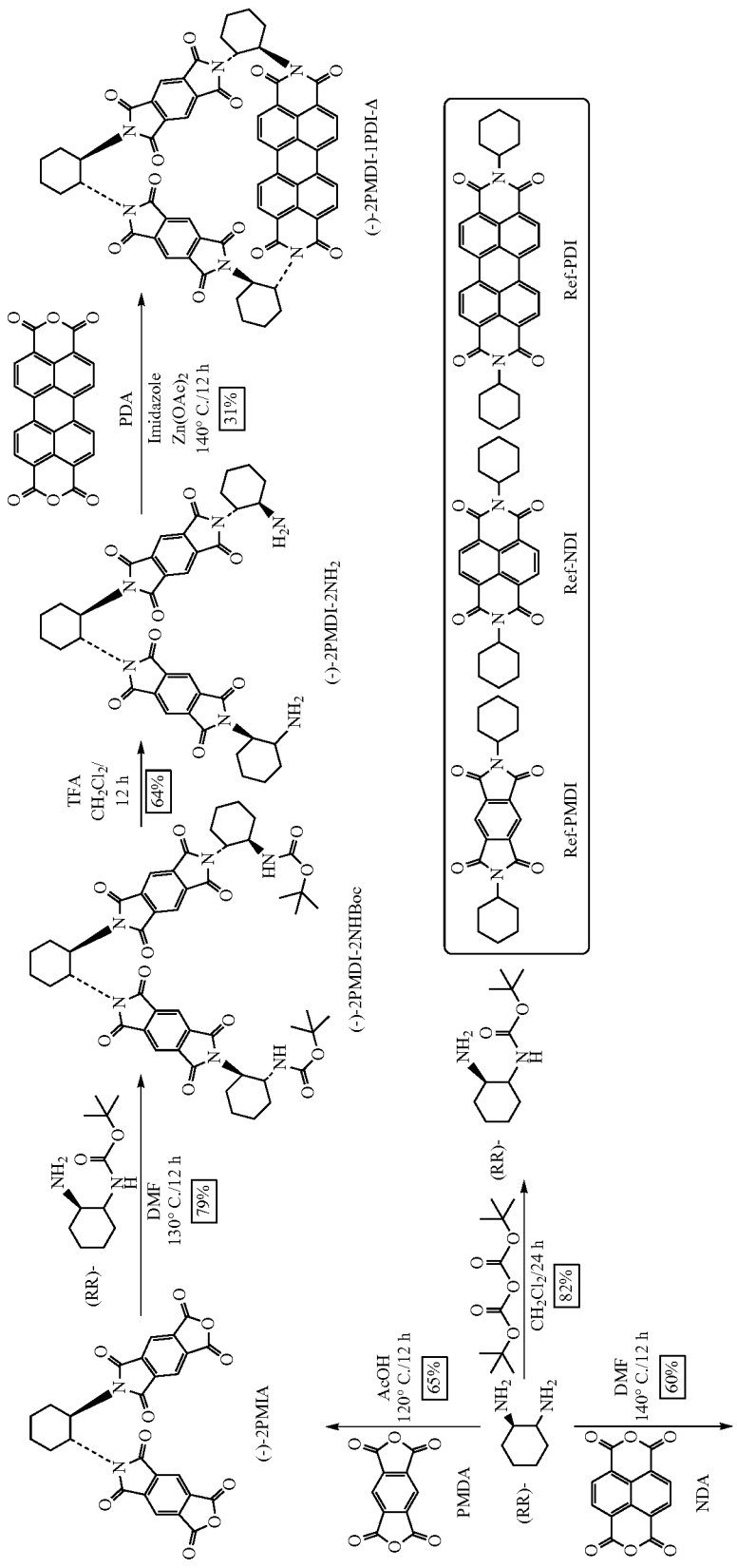

-continued
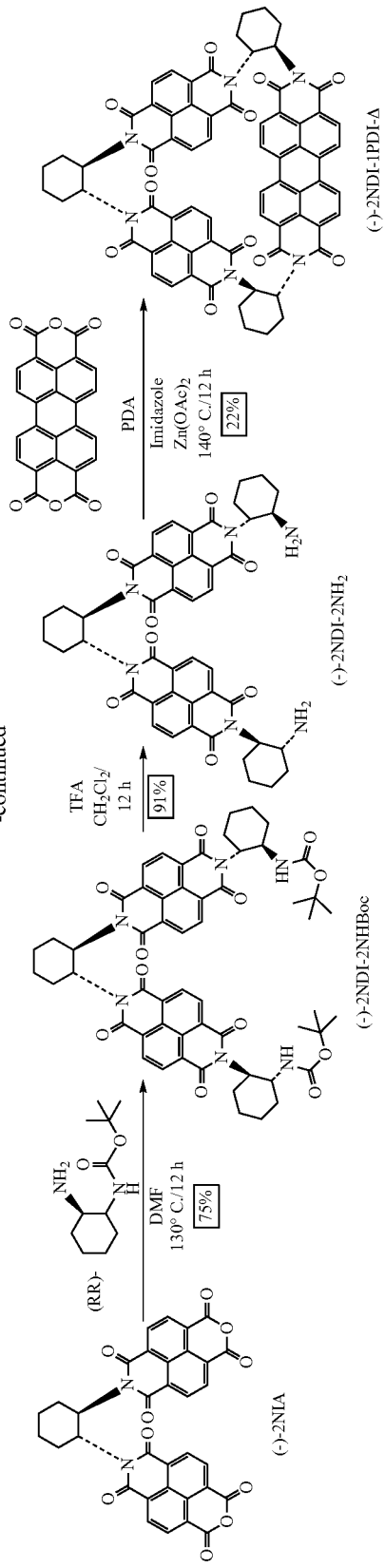

Figure 1B:
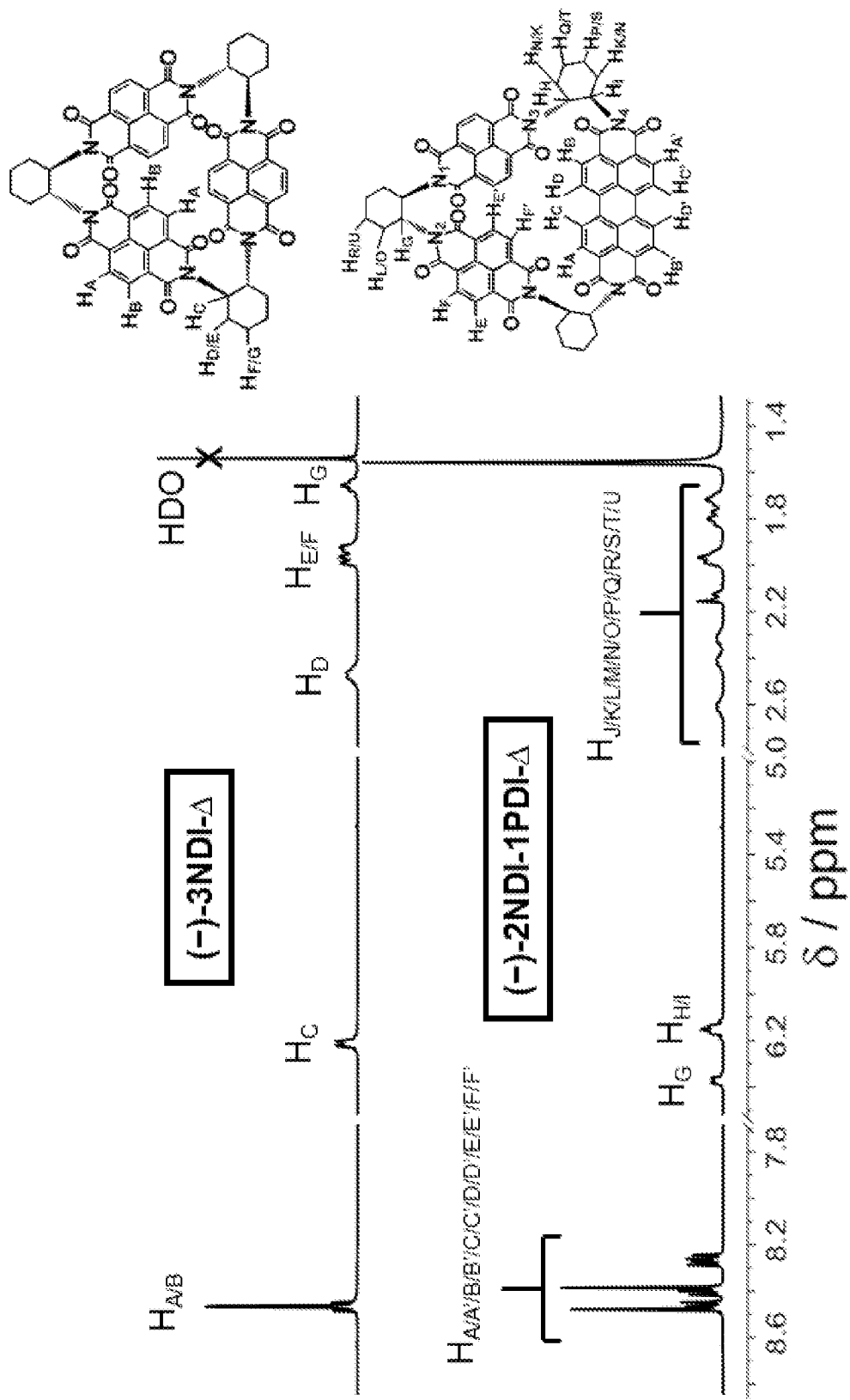
FIG. 1B compares the annotated $^1$H NMR spectra (500 MHz, CDCl$_3$, 298 K) of (−)-3NDI-Δ, (−)-2NDI-1PDI-Δ, (−)-2PMDI-1PDI-Δ and (−)-3PMDI-Δ triangular macrocycles.
Figure 1B:
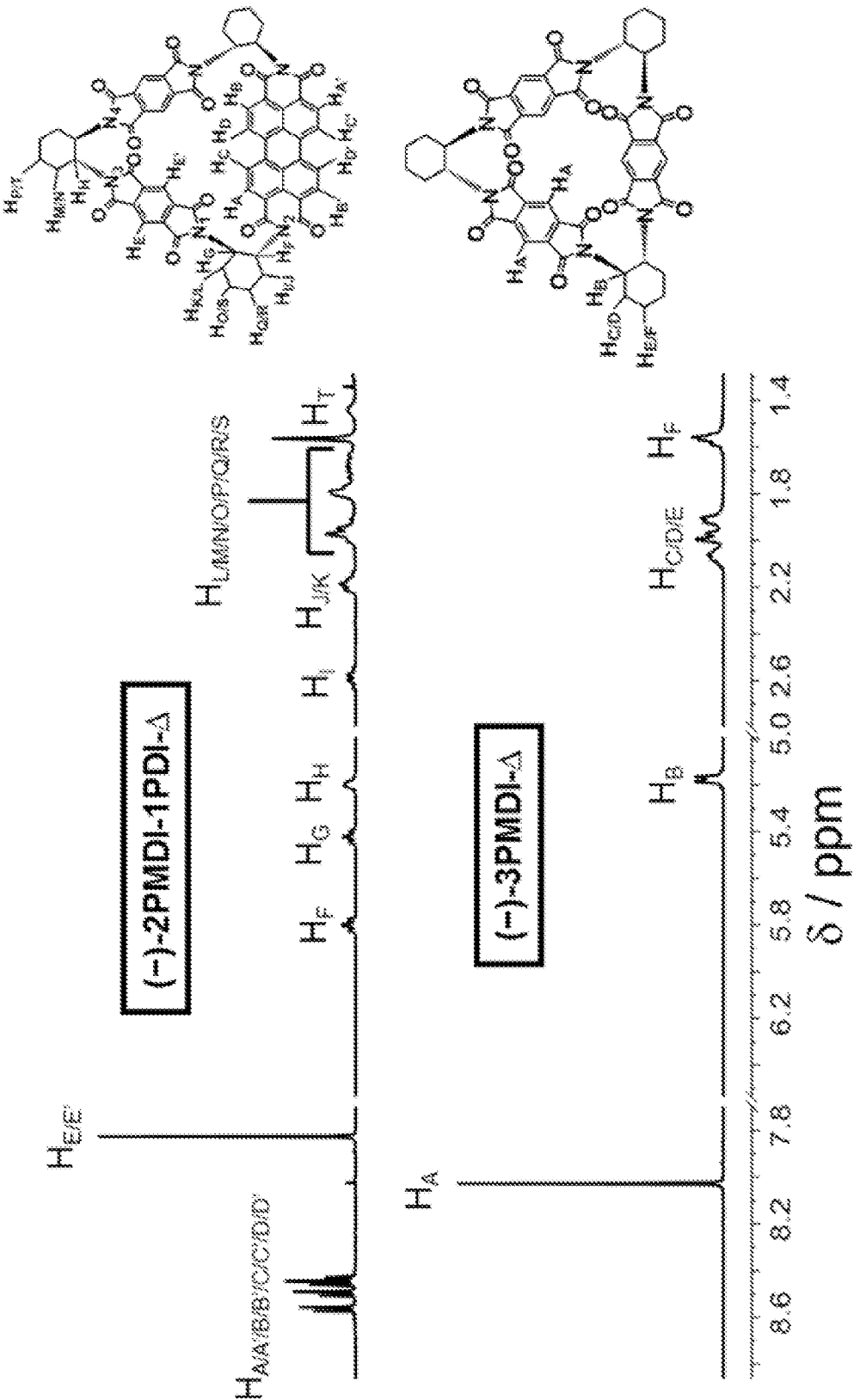
Figure 1C:
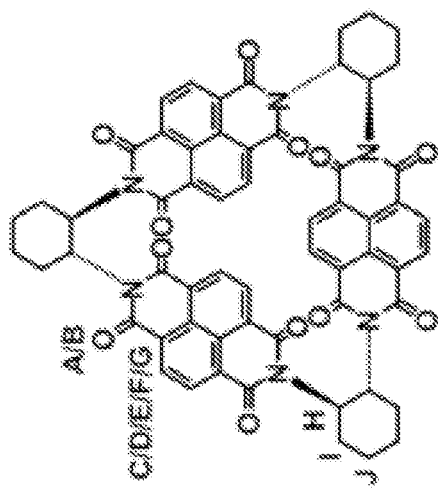
FIG. 1C compares the annotated $^{13}$C NMR spectra (125 MHz, CDCl$_3$, 298 K) of (−)-3NDI-Δ, (−)-2NDI-1PDI-Δ, (−)-2PMDI-1PDI-Δ and (−)-3PMDI-Δ triangular macrocycles.
Figure 1C:
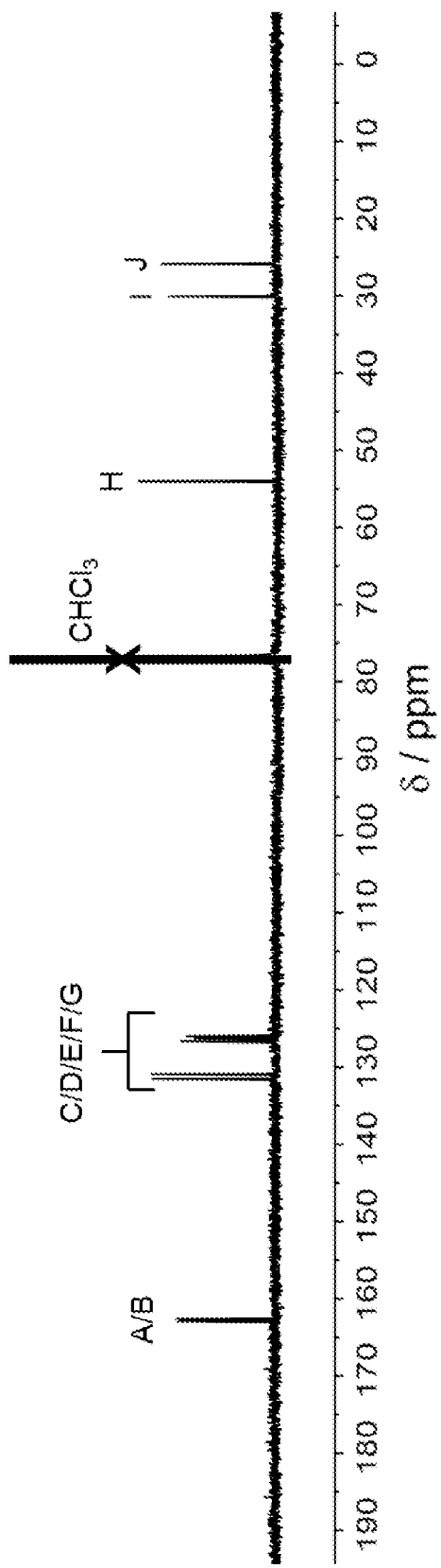
Figure 1C:
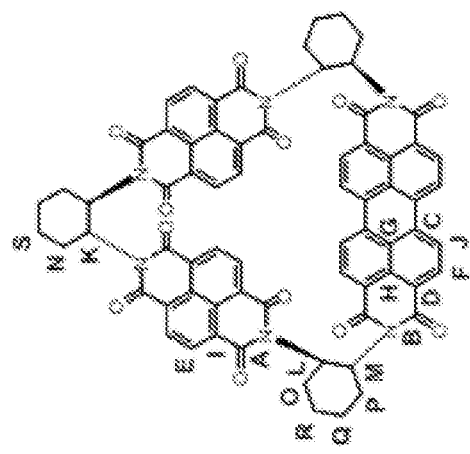
Figure 1C:
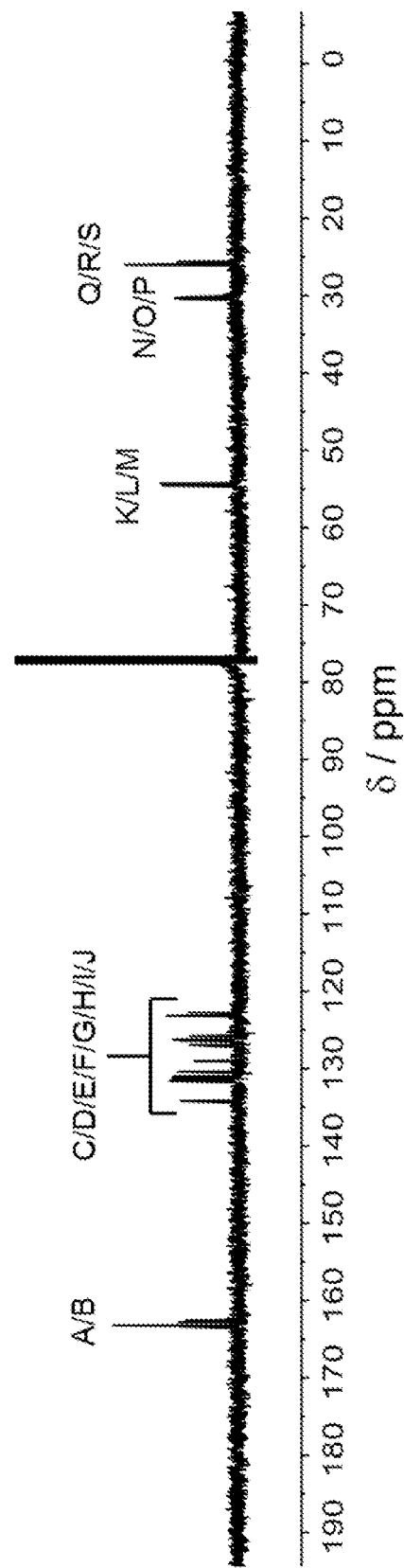
Figure 1C:
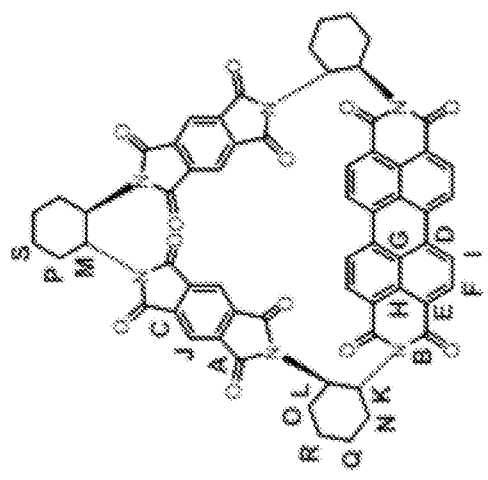
Figure 1C:
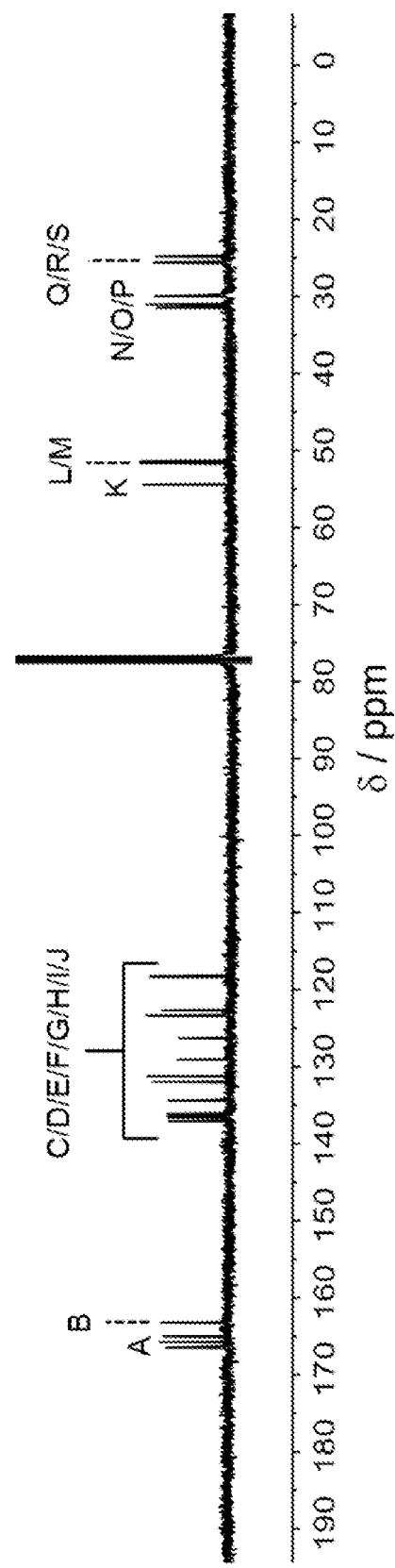
Figure 1C:
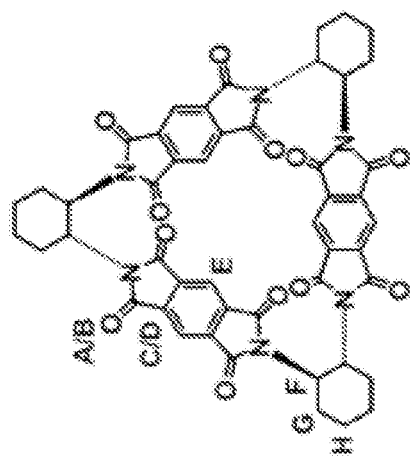
Figure 1C:
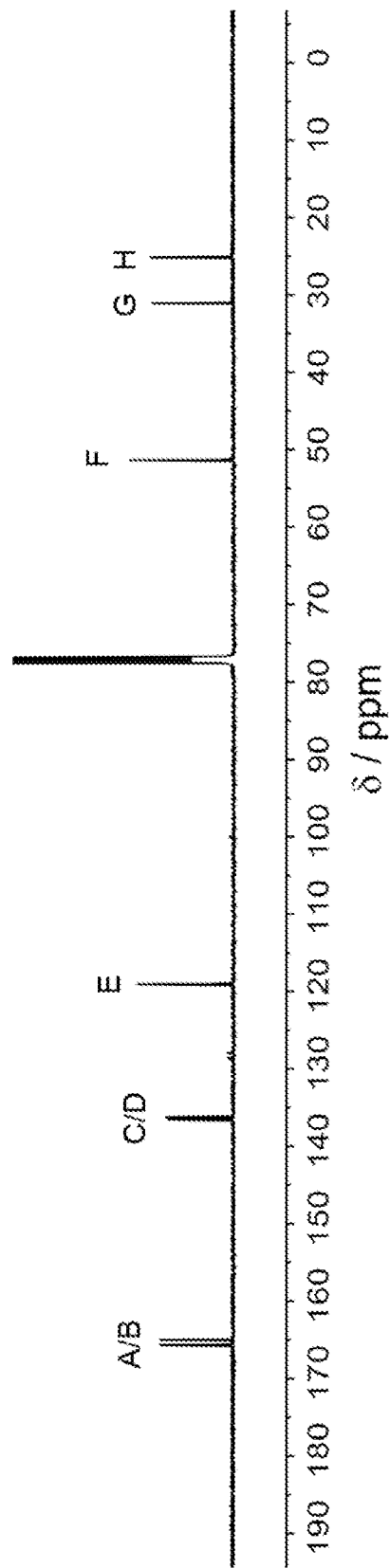

Electrospray ionization high-resolution mass spectrometry (ESI-HRMS) confirmed the existence of both (−)-2PMDI-1PDI-Δ and (−)-2NDI-1PDI-Δ by detecting the species [M+H]⁺ in the gas phase at m/z=1063.2917 and 1163.3213, respectively. Both the $^1$H and $^{13}$C NMR spectra (FIGS. 1B and 1C) of the isosceles triangles (−)-2PMDI-PDI-Δ and (−)-2NDI-1PDI-Δ confirm their chiral rigid cyclic structures with a lower symmetry ($C_2$ point group) when compared to the higher symmetry ($D_3$ point group) of the equilateral triangles [(−)-3NDI-Δ and (−)-3PMDI-Δ]. The assignments of all of the resonances corresponding to aromatic, methine and methylene protons of the triangles were confirmed by two-dimensional $^1$H-$^1$H and $^1$H-$^{13}$C correlation spectroscopies. In particular, the $^1$H NMR spectrum of (−)-2PMDI-1PDI-Δ shows (FIG. 1B) three sets of signals for the eight PDI protons, a sharp singlet for the four PMDI protons and three sets of signals for the six methine protons, while that of (−)-2NDI-1PDI-Δ shows (FIG. 1B) three sets of signals for the eight PDI protons, two sets of signals for the eight NDI protons and two sets of signals for the six methine protons.

Furthermore, we anticipated that the rigidity of these isosceles triangles could be evaluated by dynamic $^1$H NMR experiments by probing the rates of rotation of the aromatic subunits around their C—N . . . N—C bond axes. Based on our previous observations,[53,54] we believe it to be unlikely that we could access the high free energy of activation necessary for the rotation of the bulky NDI and PDI subunits around their C—N . . . N—C bond axes within the triangles on the $^1$H NMR time scale. On the other hand, the accidental overlapping of the resonances for the heterotopic PMDI protons of (−)-2PMDI-1PDI-Δ leading to a sharp singlet (FIG. 1B) even at room temperature also restricted our attempts to probe the rates of rotation of the PMDI subunits with the increase of temperature.

Quantum Mechanical (QM) Calculations

In order to investigate the conformational rigidity of aromatic subunits within the isosceles triangles, we carried out quantum mechanical calculations (FIGS. 1D-1F) to map the potential energy surface as a function of the rotational barriers of the dihedral angle ∠(H—C—N—C) for all the aromatic PDI, NDI and PMDI subunits present in all the compounds (FIGS. 1E and 1F). In the case of Ref-PDI, the activation barrier for the free rotation of PDI is only 6.85 kcal mol⁻¹. This barrier increases dramatically to 25.4 and 25.1 kcal mol⁻¹ for (−)-2PMDI-1PDI-Δ and (−)-2NDI-1PDI-Δ, respectively. This suggests that the rigid cyclization dramatically restricts the free intramolecular rotation of the PDI components.

Figure 1G:
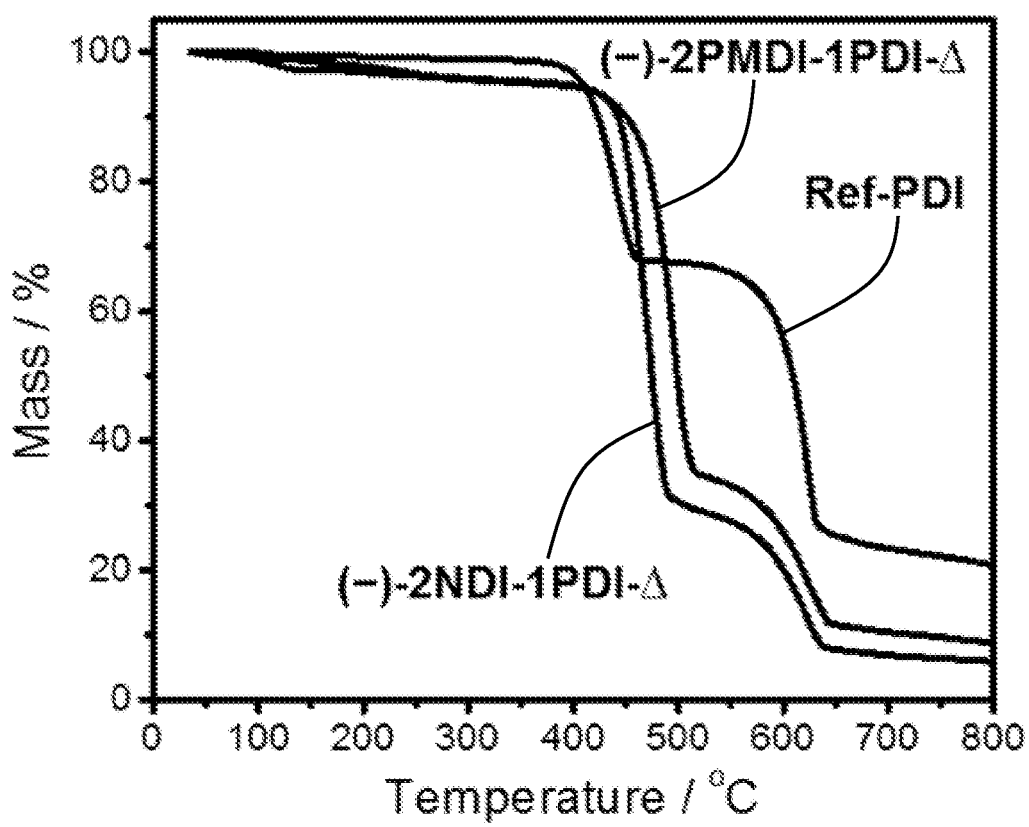
FIG. 1G shows thermogravimetric analyses (TGA) of the rigid isosceles triangles (−)-2PMDI-1PDI-Δ and (−)-2NDI-1PDI-Δ and the monomeric reference compound Ref-PDI under a nitrogen atmosphere.
Figure 1H:
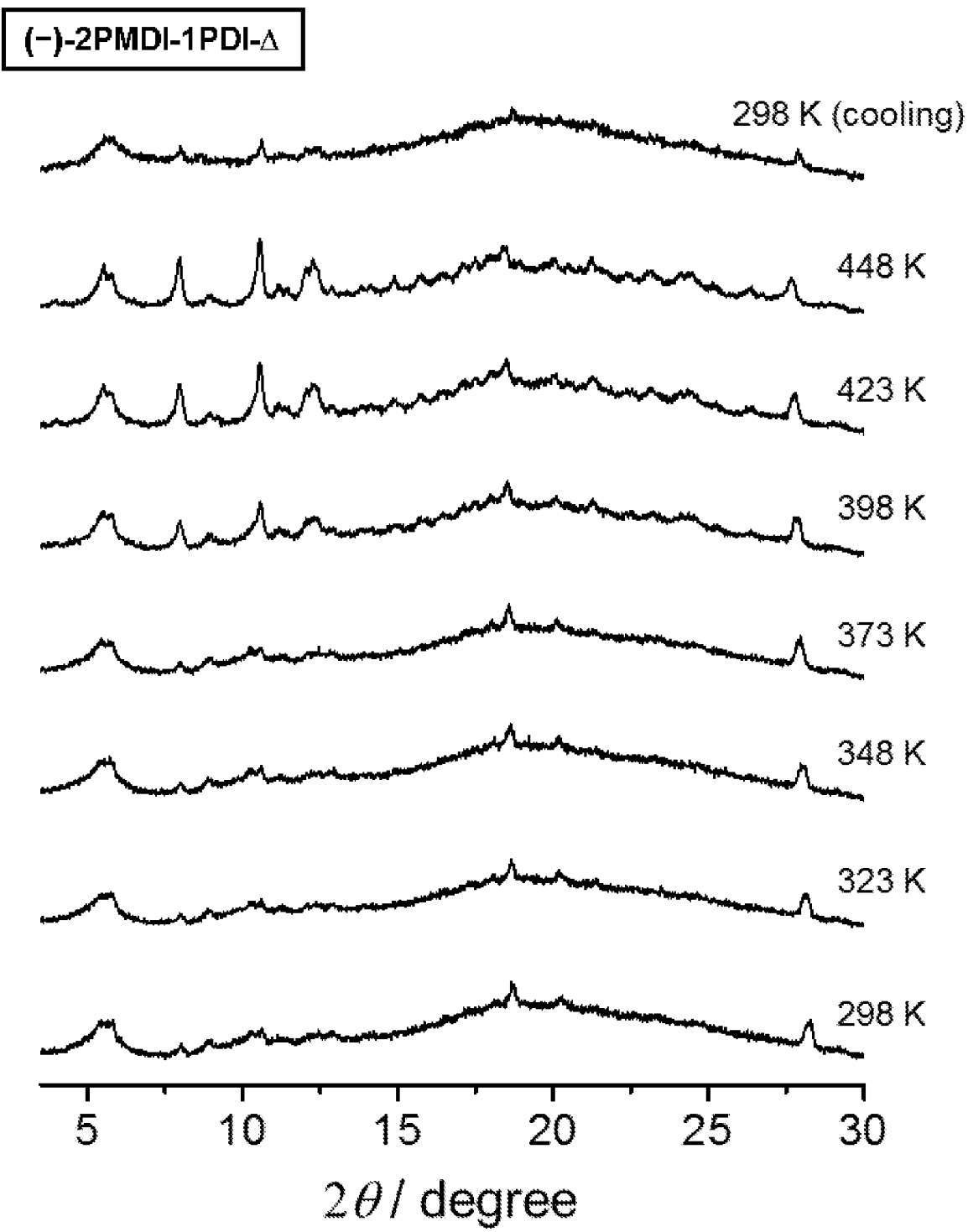
FIG. 1H shows the variable-temperature PXRD patterns of the as-synthesized powder sample of (−)-2PMDI-1PDI-Δ. The patterns indeed suggest that (−)-2PMDI-1PDI-Δ is semi-crystalline as evidenced by the relatively broad peaks at 298 K which gradually sharpen upon increasing the temperature above 373 K (b.p. of H$_2$O), while it retained the same degree of crystallinity upon subsequent cooling to room temperature.
Figure 1I:
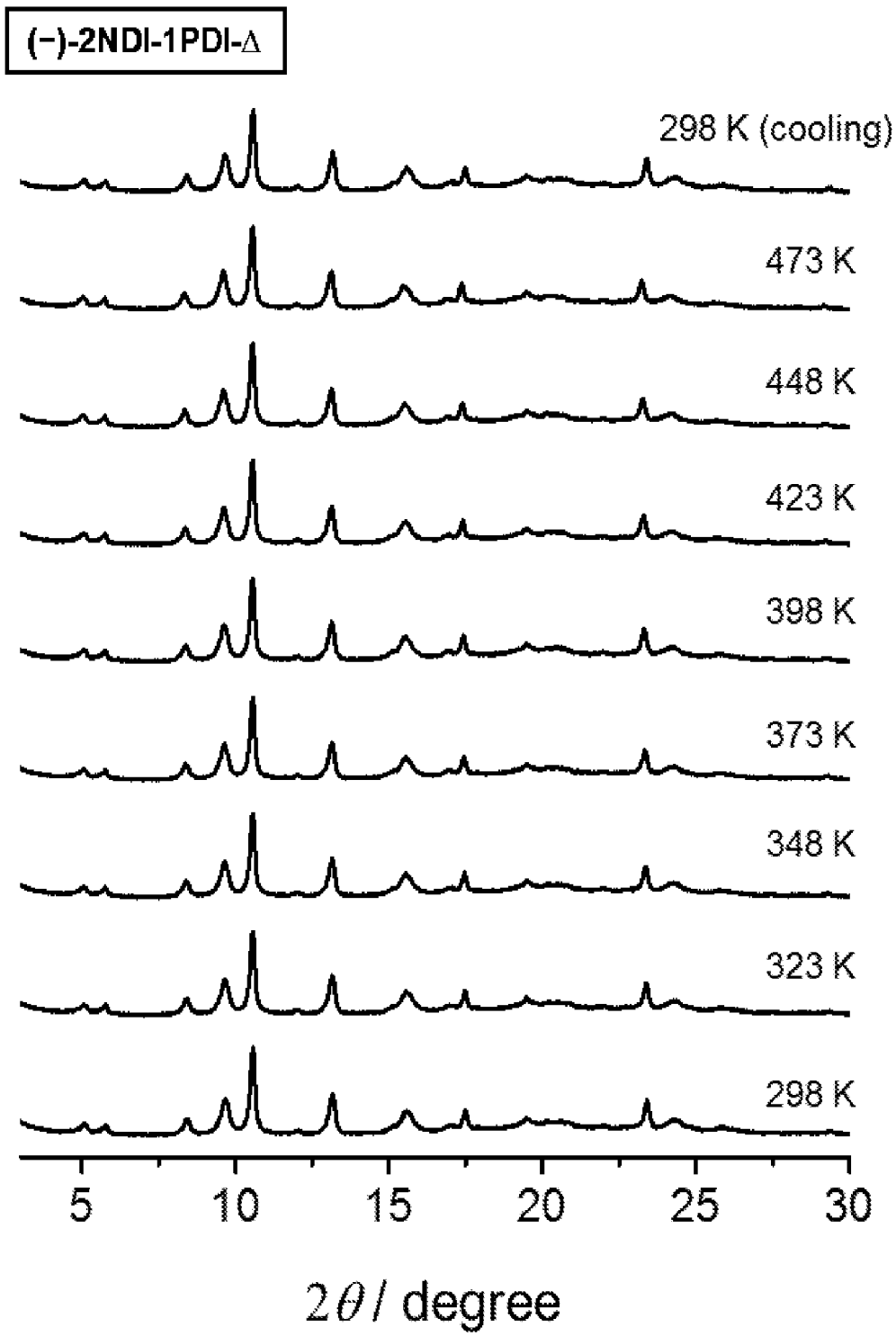
FIG. 1I shows the variable-temperature PXRD patterns of the as-synthesized powder sample of (−)-2NDI-1PDI-Δ. The patterns indeed suggest that the crystalline structure is thermally stable up to 473 K which retains the same degree of crystallinity after subsequent cooling to room temperature.

After investigating the rigidity of the isosceles triangles, we conducted thermogravimetric analyses under a nitrogen atmosphere in order to determine their thermal stability. Although an initial mass loss of up to 4% below 250° C. was observed (FIG. 1G) for (−)-2PMDI-1PDI-Δ and (−)-2NDI-1PDI-Δ when compared to that of Ref-PDI, the triangles exhibited high thermal stability up to 410° C. where they began to decompose. Moreover, variable-temperature powder X-ray diffraction (VT-PXRD) studies were performed on the as-synthesized powder samples of the isosceles triangles to obtain insights into their thermal stability, crystallinity and phase purity. The PXRD patterns of (−)-2PMDI-1PDI-Δ at room temperature indicate (FIG. 1H) that it is semi-crystalline, while the sharpening of peaks with the rise in temperature up to 443 K suggests its increased crystallinity. The original degree of crystallinity is, however, obtained upon subsequent cooling to room temperature. On the other hand, PXRD patterns of (−)-2NDI-1PDI-Δ at room temperature reveal (FIG. 1I) its crystalline structure which is, not only thermally stable up to 473 K, but also retains the same crystalline structure upon subsequent cooling to room temperature. In addition to their superior structural and conformational rigidity, the remarkable thermal stability of (−)-2PMDI-1PDI-Δ and (−)-2NDI-1PDI-Δ is promising for practical applications in organic electronic devices.

Single-Crystal X-Ray Diffraction (XRD) Analyses

Single-crystal X-ray diffraction analyses were carried out in order to gain insights into structural details and packing arrangements of these rigid isosceles triangular macrocycles. Single crystals of (−)-2PMDI-1PDI-Δ were obtained by slow vapor diffusion of n-hexane into a 3 mM solution in 1,2-dichloroethane (DCE) over the course of 3 days, while single crystals of (−)-2NDI-1PDI-Δ were obtained by slow evaporation of a 6 mM solution in CHCl₃ during 7 days. The crystal structures of both (−)-2PMDI-1PDI-Δ and (−)-2NDI-1PDI-Δ reveal (FIGS. 2A and 2B) the tensioned rigid geometries of the isosceles triangular hollow prisms which are characterized by similar vertex angles (FIGS. 2C and 2E) of ~88°—a value which is much greater than 60° of the equilateral triangle (−)-3NDI-Δ[49,50,53]—as a result of the stretching of the long and curved PDI subunits. On account of the fact that the PMDI units (9.6 Å) are slightly shorter than the NDI units (10.0 Å), the height (8.8 Å) of (−)-2PMDI-1PDI-Δ is shorter than the height (9.5 Å) of (−)-2NDI-1PDI-Δ. The angle (102°) between the PDI and the triangular planes in (−)-2PMDI-1PDI-Δ is (FIGS. 2D and 2F) larger than that (86°) in (−)-2NDI-1PDI-Δ as a result of the less bulky PMDI units in comparison with NDI units. In addition, the PDI plane (14.1 Å) of (−)-2PMDI-1PDI-Δ is more bent than the PDI plane (14.1 Å) of (−)-2NDI-PDI-Δ. These observations indicate that the triangular structure of (−)-2PMDI-1PDI-Δ is relatively more strained than that of (−)-2NDI-1PDI-Δ. In both crystal superstructures, every two (−)-2PMDI-1PDI-Δ and every two (−)-2NDI-1PDI-Δ form (FIGS. 2C-2F) nearly face-to-face π-π dimers by means of π-π stacking interactions (3.4 Å) between nearly parallel PDI units, respectively. Although both PDI units in the π-π dimer of (−)-2PMDI-1PDI-Δ are almost parallel, there are some offsets between the lengths (1.3 Å) and the widths (0.6 Å) of two overlaying PDI units. In contrast, in the π-π dimer of (−)-2NDI-1PDI-Δ, the offsets between the lengths (2.0 Å) and the widths (4.0 Å) of two PDI units are much greater, an observation which indicates that the π-π stacking interactions between PDI units of (−)-2PMDI-1PDI-Δ are more efficient than those in (−)-2NDI-1PDI-Δ. This result can be ascribed to the fact that the more bent PDI units of (−)-2PMDI-1PDI-Δ results in them exposing larger π-surfaces of PDI units for π-π stacking while at the same time weakens the steric barriers from the cyclohexano groups and thus favors the overlap of the larger areas provided by the two PDI units between adjacent (−)-2PMDI-1PDI-Δ. In the extended superstructures, every four π-π dimers of (−)-2PMDI-1PDI-Δ and (−)-2NDI-1PDI-Δ, in different orientations, pack in the presence of solvent molecules into a crystal unit cell, respectively. Most interestingly, no significant non-covalent bonding interactions were found; namely, π-π stacking and [C—H . . . O] interactions between PMDI/PMDI, PMDI/PDI, NDI/NDI, or NDI/PDI pairs which are very commonly observed previously in the cases of (−)-3NDI-Δ,[49,50,53] (−)-1PMDI-2NDI-Δ, and (−)-2PMDI-1NDI-Δ triangles[54]. In addition, the X-ray structures reveal that the nanoporous cavities of both isosceles triangles are indeed encapsulated by the solvent molecules as evidenced by (−)-2PMDI-1PDI-Δ forming (FIGS. 2I and 2J) a 2:1 host-guest complex with n-hexane as a result of multiple [C—H ... π] interactions, while CHCl$_3$ molecules are bound (FIGS. 2K and 2L) to the cavities of (−)-2NDI-1PDI-Δ stabilized by multiple [Cl ... π] interactions (~3.4 Å) with the π-surfaces of NDI and PDI subunits.

On the other hand, Hirshfeld surface analyses[64] performed on the structures of the two isosceles triangles confirmed (FIGS. 2M and 2N) that the reciprocal [π ... π] interactions, which contribute about 12.2 and 12.1% to the Hirshfeld surfaces of (−)-2PMDI-1PDI-Δ and (−)-2NDI-1PDI-Δ, respectively, are the most significant interactions between the PDI units in the case of both π-π dimers. In order to assess the robustness of such discrete nearly cofacial π ... π dimer packing motifs, several attempts have been made to crystallize these triangles from a range of different solvents. Although single crystals suitable for XRD analysis could not be obtained in most cases, (−)-2PMDI-1PDI-Δ did crystallize from the slow vapor diffusion of n-hexane into a 3 mM solution of (−)-2PMDI-1PDI-Δ in CHCl$_3$ over the course of several days. Single-crystal XRD analysis reveals (FIGS. 2O-2Q) that (−)-2PMDI-1PDI-Δ also forms discrete nearly cofacial PDI-PDI π-dimers which exhibit identical packing arrangements and the unit cell parameters to those observed for the DCE/n-hexane system. Also, in order to understand the role of solvents on the formation of such discrete PDI-PDI π-dimers in the solid state, solvent-free single crystals of (−)-2PMDI-1PDI-Δ, suitable for XRD analysis, were obtained by air drying the single crystals grown by slow vapor diffusion of n-hexane in CHCl$_3$ solution. It was observed (FIGS. 2R and 2S) that the discrete PDI-PDI π-dimers remained intact, with no change in the unit cell parameters before and after the evaporation of CHCl$_3$ from the single crystals. Based on all of these observations, it can be concluded that the geometries of the triangular hollow prisms of (−)-2PMDI-1PDI-Δ and (−)-2NDI-1PDI-Δ facilitate specifically the formation only of the discrete nearly cofacial π-π dimers involving two PDI units by preventing the PDI π-π dimers from further long-range π-π stacking and aggregation, which otherwise occurs[63] very easily in most of the PDI derivatives. We anticipated that the presence of the geometrically protected rigid discrete PDI π-π dimers of the triangles may be reflected in their solid-state photoluminescence properties.

UV/Vis Absorption, CD and Fluorescence Studies in Solution

Figure 3A:
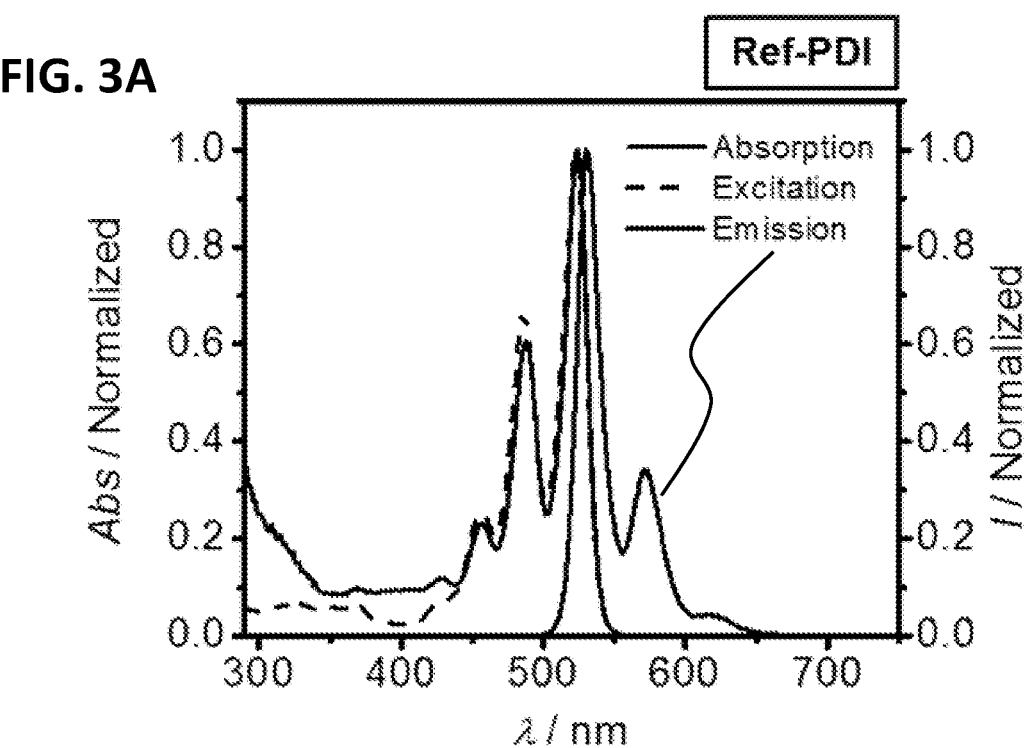
FIGS. 3A-3D show photophysical studies of reference compound and isosceles triangles in solution.
Figure 3B:
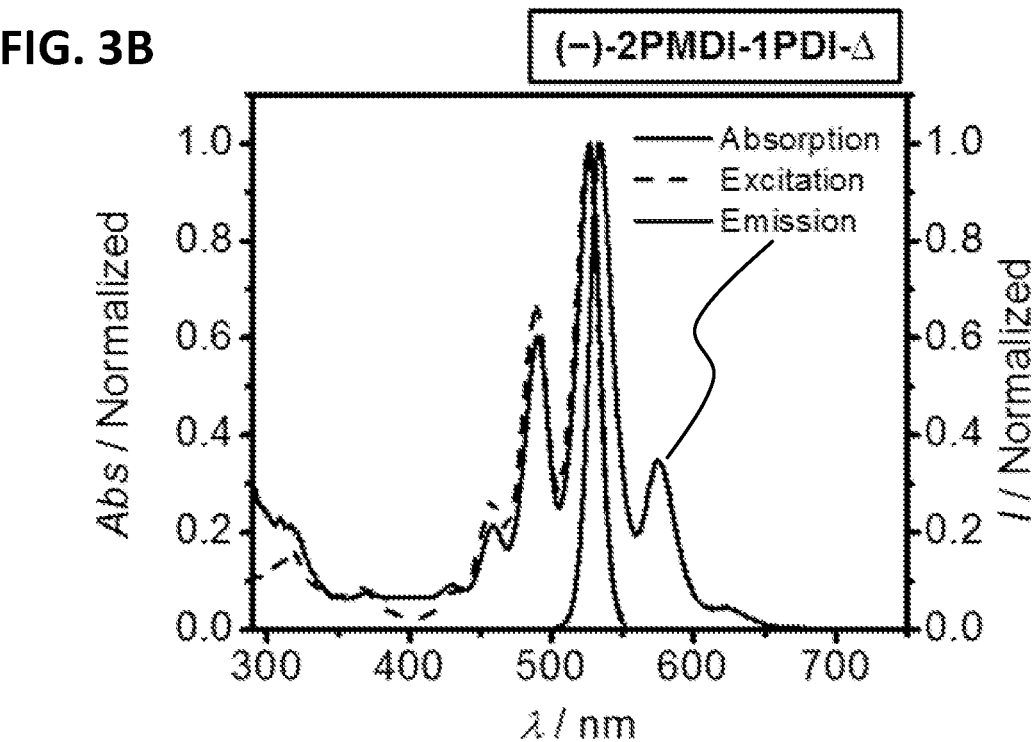
Figure 3C:
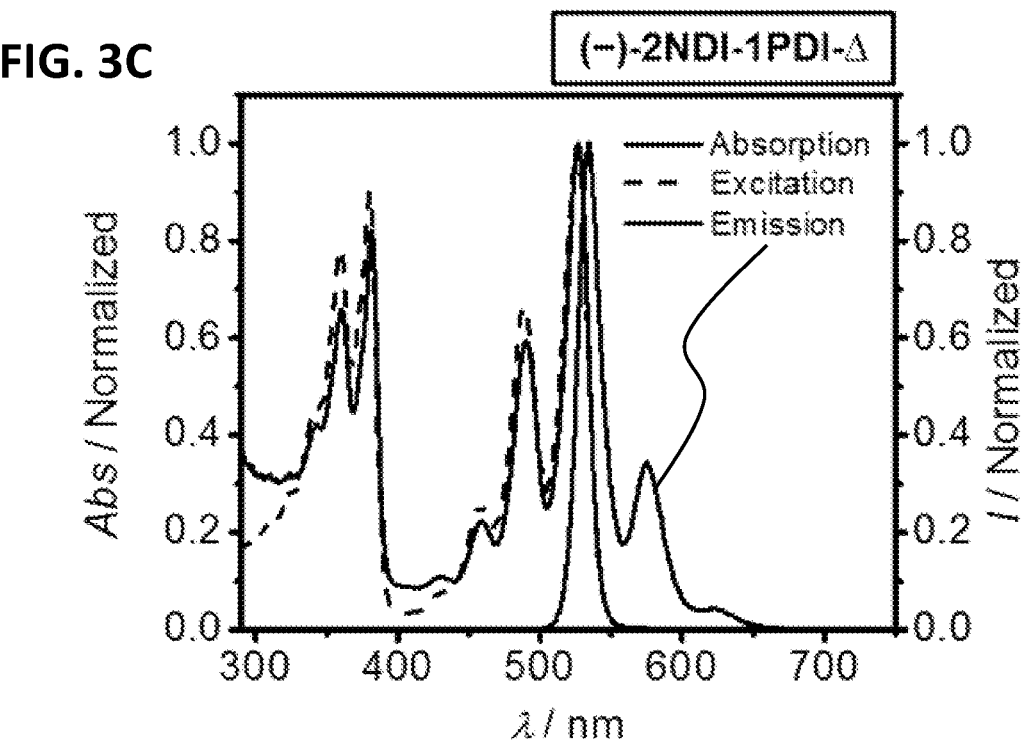

Motivated by the variation in the structural properties and the unusual packing arrangements of the rigid isosceles triangles in the solid state as evidenced by single-crystal XRD, we first set out to investigate (i) the optical properties of all three compounds by steady-state UV/Vis absorption and fluorescence spectroscopies in solution (Table 1), and (ii) the chiroptical behavior of the isosceles triangles by CD spectroscopy in solution. The absorption spectra (FIGS. 3A-3C) of all three compounds recorded in CH$_2$Cl$_2$ displayed three well-defined vibronic bands with maxima between 456-459 nm, 487-490 nm, 524-527 nm, corresponding to the characteristic $S_1 \leftarrow S_0$ electronic transition of the PDI derivatives. This observation suggests that the imide substituents of PDI subunits present in all three compounds have a negligible impact on their electronic transitions. Additionally, the absorption spectra (FIG. 3C) of (−)-2NDI-1PDI-Δ displayed two vibronic progressions, centered on 360 and 380 nm, corresponding to the characteristic $S_1 \leftarrow S_0$ electronic transition of the NDI subunits. The molar extinction coefficients of both the isosceles triangles are smaller (Table 1) than that of Ref-PDI. Consequently, the CD spectra (FIGS. 3E and 3F) of both chiral isosceles triangles displayed prominent negative exciton Cotton effects in 225-250 nm, 350-400 nm and 450-550 nm regions, corresponding to the electronic transitions of PMDI, NDI and PDI subunits, respectively, where the sign of the peaks is consistent with the absolute (RRRRRR)-configuration of the triangles. The fluorescence spectra (FIGS. 3A-3C) of all three compounds displayed similar monomeric emission bands with mirror-image vibronic patterns to their absorption spectra. The fluorescence quantum yield measured in CH$_2$Cl$_2$ relative to that of Ref-PDI ($\Phi_f$~1.0)[43] is almost unity ($\Phi_f$~1.0) for (−)-2PMDI-1PDI-Δ, while that for (−)-2NDI-1PDI-Δ is only slightly lower ($\Phi_f$~0.88). Similarly, all three compounds also exhibited excellent fluorescence quantum yields ($\Phi_f$~90-100%) in other organic solvents, such as MeCN and PhMe, except the partially quenched fluorescence of (−)-2NDI-1PDI-Δ ($\Phi_{f, PhMe}$=63%) in PhMe which can be attributed to aggregation-caused quenching.

Figure 3D:
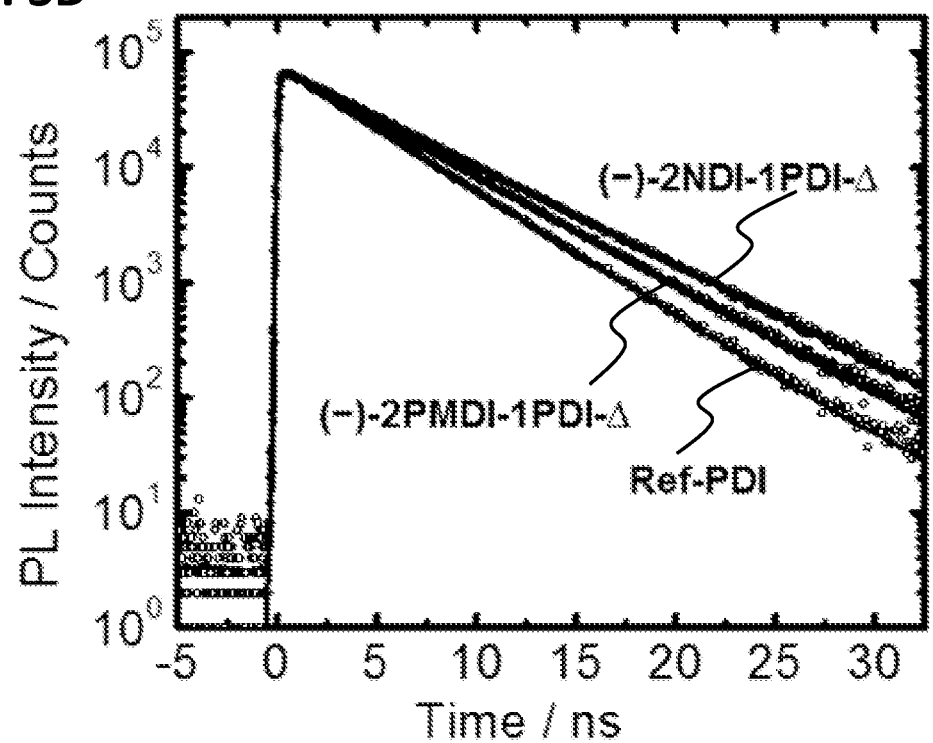
Figure 3G:
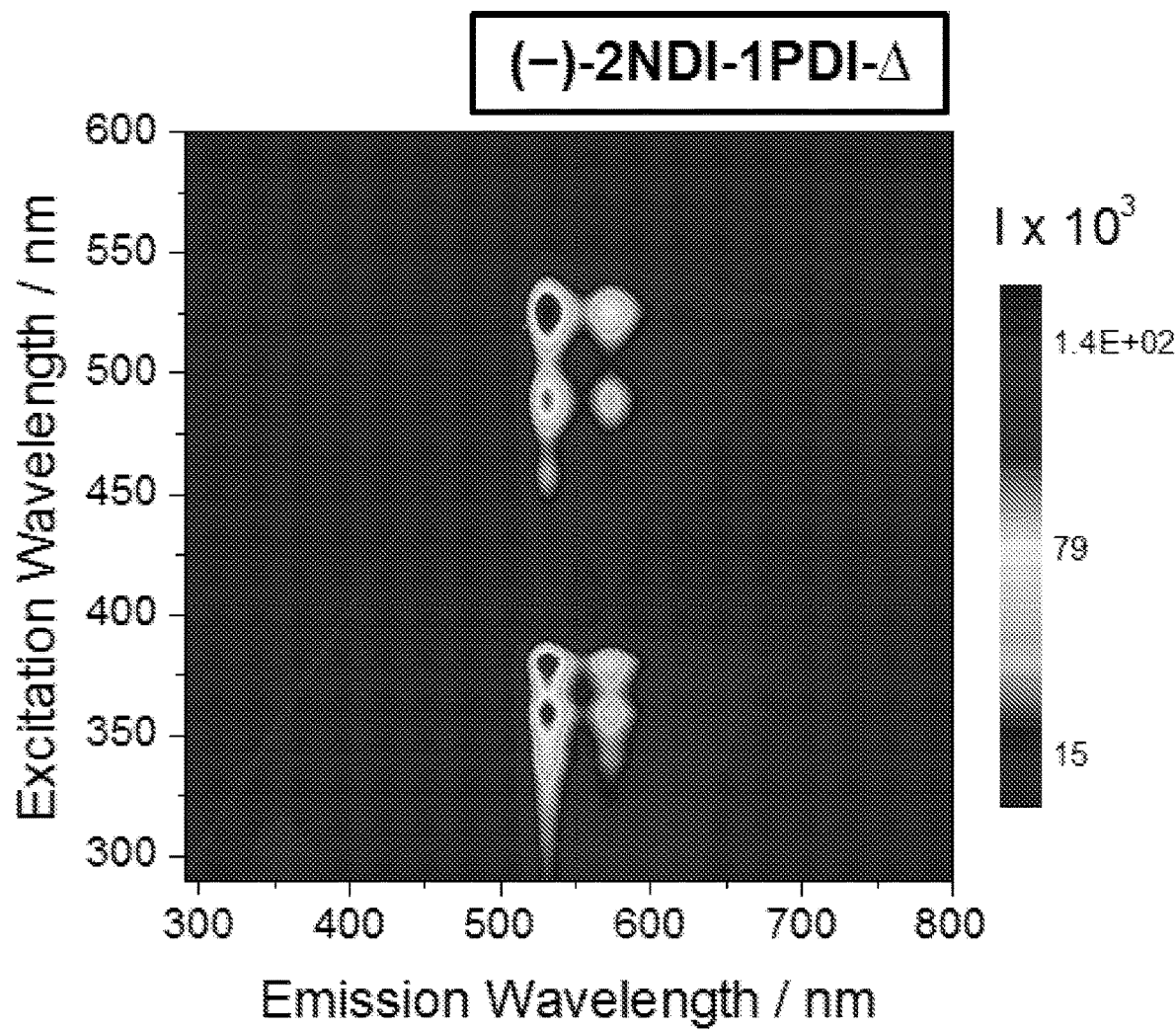
FIG. 3G shows an excitation-emission photoluminescence contour plot for (−)-2NDI-1PDI-Δ recorded in $CH_2Cl_2$ at 298 K, suggesting the efficient energy transfer from the lowest excited singlet state of NDI to that of the PDI subunit within the isosceles triangle (−)-2NDI-1PDI-Δ upon photoexcitation of the NDI subunits.

In addition, the excitation spectra (FIGS. 3A-3C) of all three compounds match well with their absorption spectra, suggesting that the emission arises from only one excited species. The excitation spectrum (FIG. 3C) of (−)-2NDI-1PDI-Δ exhibited, however, additional peaks in the region 350-390 nm which match perfectly with the vibronic progressions corresponding to the electronic transition localized on the NDI subunits in its absorption spectrum. This observation suggests that there is an efficient energy transfer from the lowest excited singlet state of NDI to that of the PDI subunit within the isosceles triangle (−)-2NDI-1PDI-Δ upon photoexcitation of the NDI subunits (FIG. 3G). Furthermore, the time-resolved fluorescence spectra (FIG. 3D) of all three compounds in CH$_2$Cl$_2$ displayed mono-exponential decay curves with similar lifetimes $<\tau_{em}>$ of 4.0, 4.5 and 5.0 ns for Ref-PDI, (−)-2PMDI-1PDI-Δ and (−)-2NDI-1PDI-Δ, respectively.

TABLE 1

Photophysical properties of reference compound and isosceles triangles in CH$_2$Cl$_2$ and in the solid state at room temperature.

| Compound | Absorption $\lambda_{abs}$ (nm) | $\varepsilon$/M$^{-1}$ cm$^{-1}$ | Fluorescence $\lambda_{em}$ (nm) | Quantum yield $\Phi_f$ (%)$^a$ CH$_2$Cl$_2$$^a$ | MeCN$^b$ | PhMe$^b$ | Lifetime $<\tau_{em}>$ (ns) |
|---|---|---|---|---|---|---|---|
| Ref-PDI | 524 | 78 370 | 530 | 100 | 89 | 94 | 4.0 |
| (−)-2PMDI-1PDI-Δ | 527 | 61 490 | 534 | 100 | 96 | 100 | 4.5 |
| (−)-2NDI-1PDI-Δ | 527 | 63 250 | 534 | 88 | 100 | 63$^c$ | 5.0 |

TABLE 1-continued

Photophysical properties of reference compound and isosceles triangles
in $CH_2Cl_2$ and in the solid state at room temperature.

| Compound | Photoluminescence $\lambda_{em}$ (nm) | Quantum yield (%)[d] Powder ($\Phi_{powder}$) | Film ($\Phi_{film}$) | Lifetime $<\tau_{em}>$ (ns) |
| --- | --- | --- | --- | --- |
| Ref-PDI | 652 | 0.1 | 0.2 | 1.5 |
| (−)-2PMDI-1PDI-Δ | 670 | 3 | 2 | 13.4 |
| (−)-2NDI-1PDI-Δ | 602 | 4 | 2 | 3.0 |

[a]Relative fluorescence quantum yields in $CH_2Cl_2$ were determined with N,N'-dicyclohexylperylene-3,4:9,10-tetracarboxylic acid diimide as a reference under high dilution conditions (within ±3% error).
[b]Absolute fluorescence quantum yields were measured in MeCN and PhMe using an integrating sphere under high dilution conditions (within ±3% error).
[c]Reduced $\Phi_f$ value of (−)-2NDI-1PDI-Δ in PhMe can be attributed to aggregation-caused quenching.
[d]Absolute photoluminescence quantum yields in the solid state (powder form and film state) were determined with an integrating sphere (within ±5% error).

Photophysical Studies in the Solid State

Figure 2A:
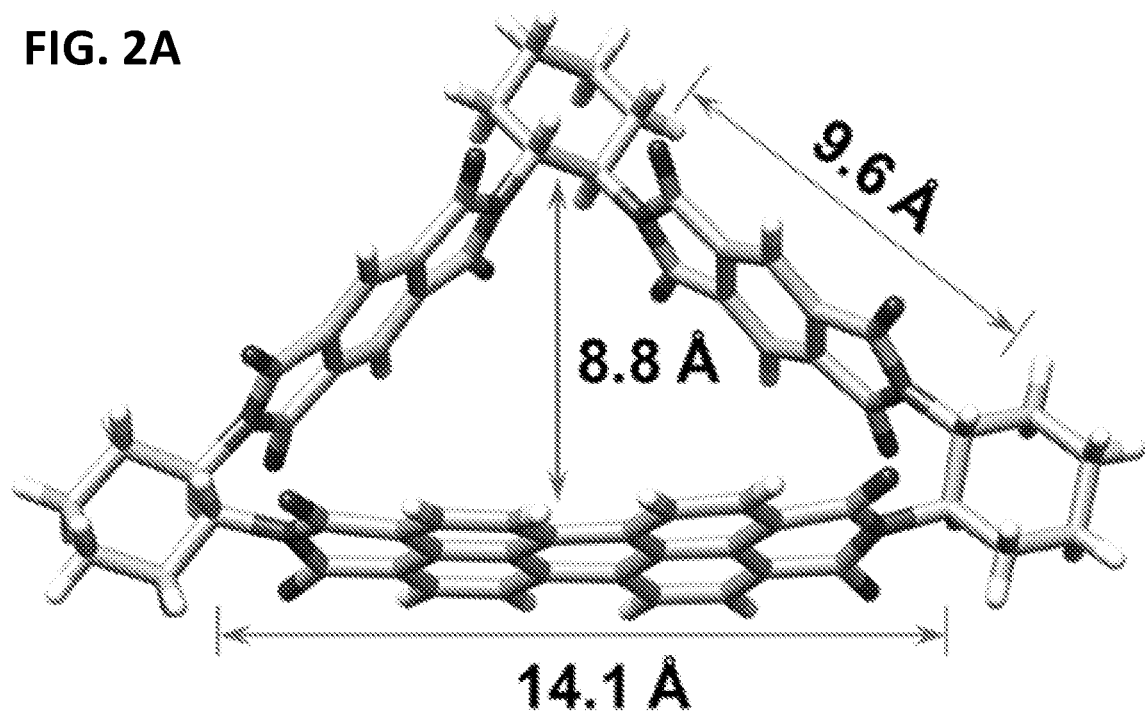
FIGS. 2A and 2B show single-crystal X-ray structures tubular representations of (−)-2PMDI-1PDI-Δ (FIG. 2A) and (−)-2NDI-1PDI-Δ (FIG. 2B).
Figure 2B:
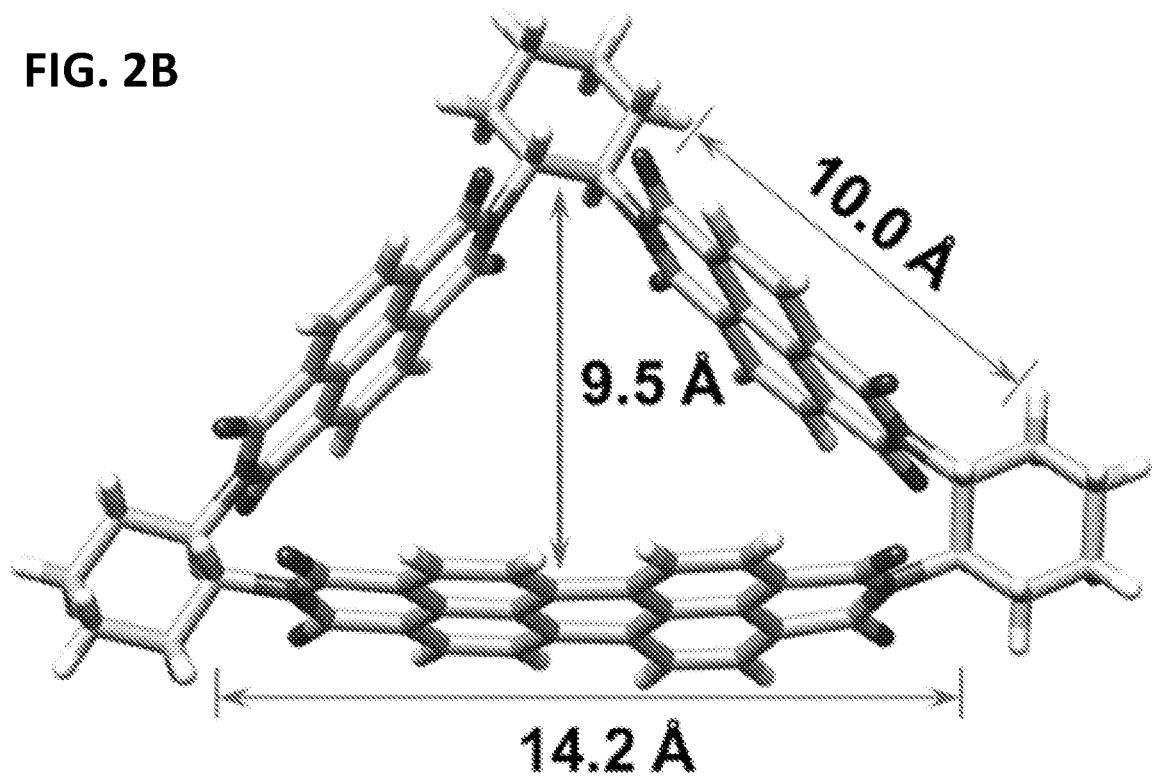
Figure 2C:
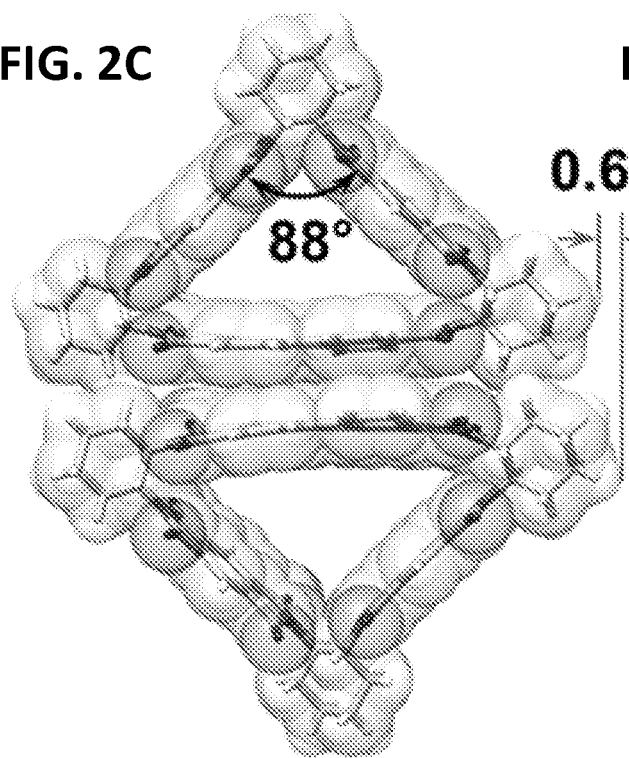
FIGS. 2C-2F shows single-crystal X-ray structures from a top and side-on view of π-π stacking dimers of (−)-2PMDI-1PDI-Δ (FIGS. 2C and 2D) and (−)-2NDI-1PDI-Δ (FIGS. 2E and 3F).
Figure 2D:
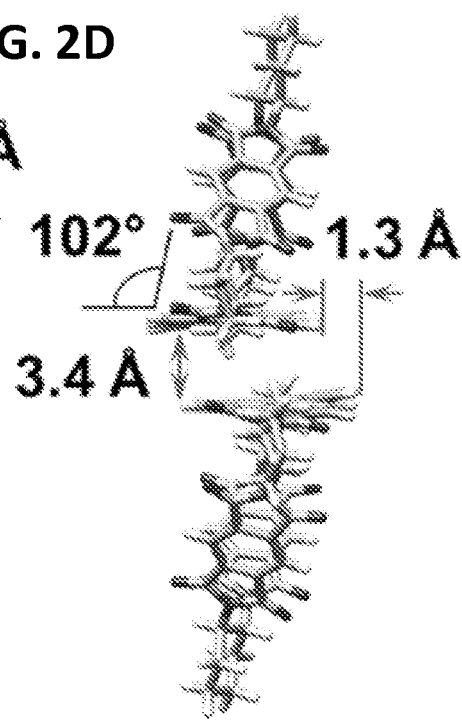
Figure 2E:
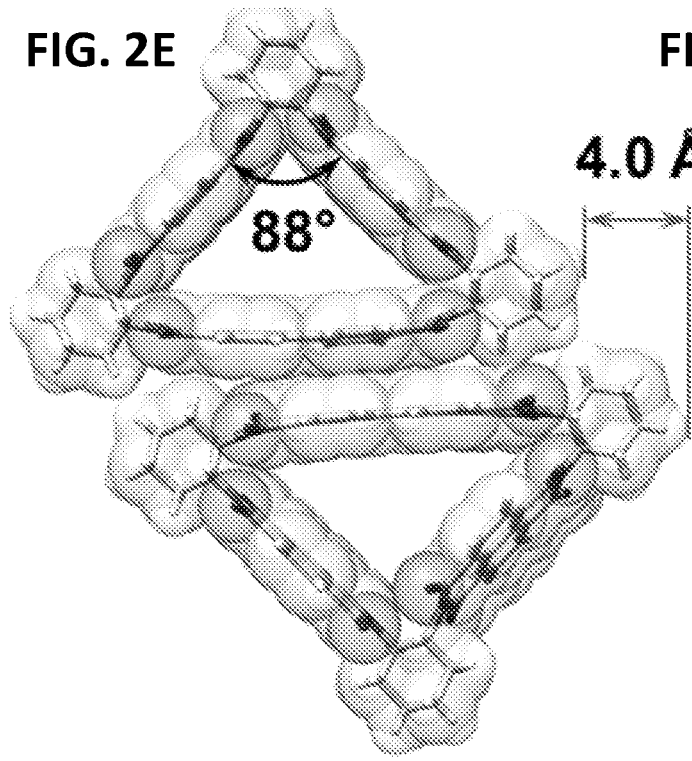
Figure 2F:
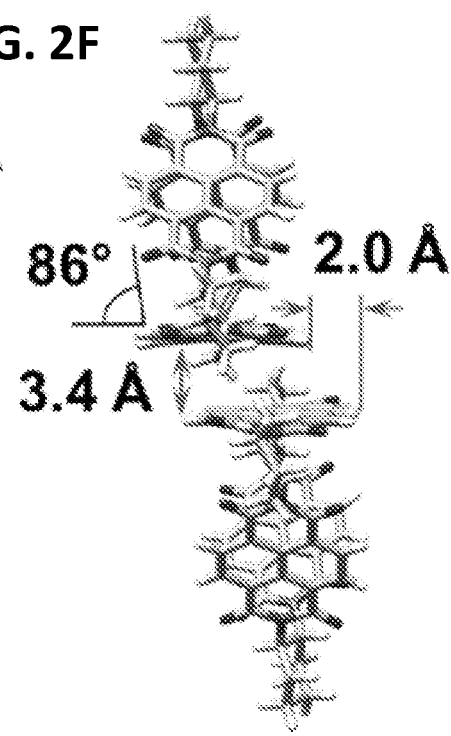
Figure 2G:
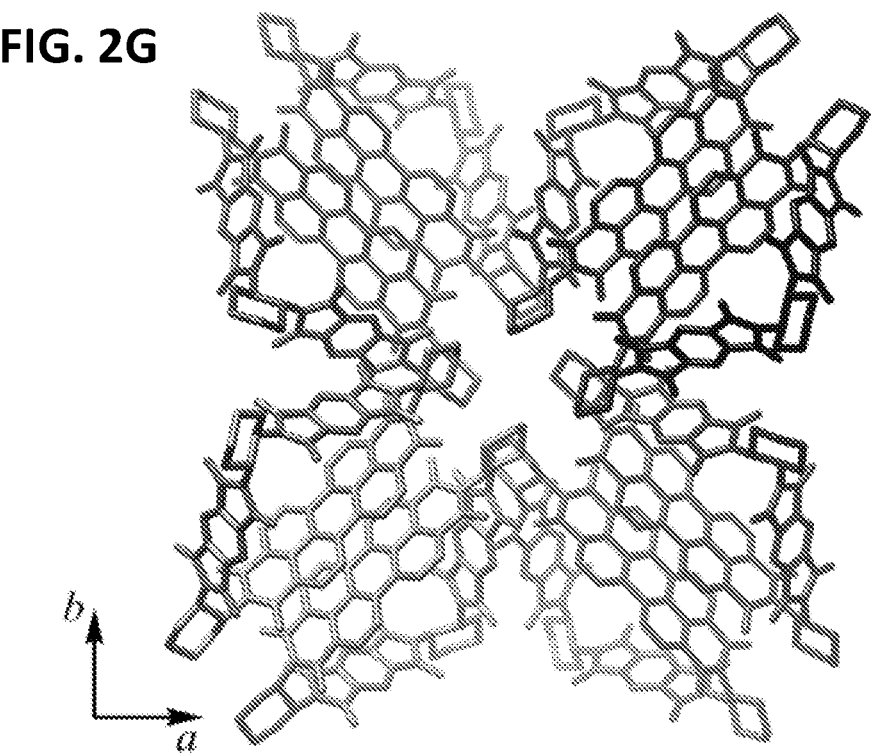
FIGS. 2G and 2H show single-crystal X-ray structures from a view along c-axis of the unit cell of (−)-2PMDI-1PDI-Δ (FIG. 2G) and a view along b-axis of the unit cell of (−)-2NDI-1PDI-Δ (FIG. 2H).
Figure 2H:
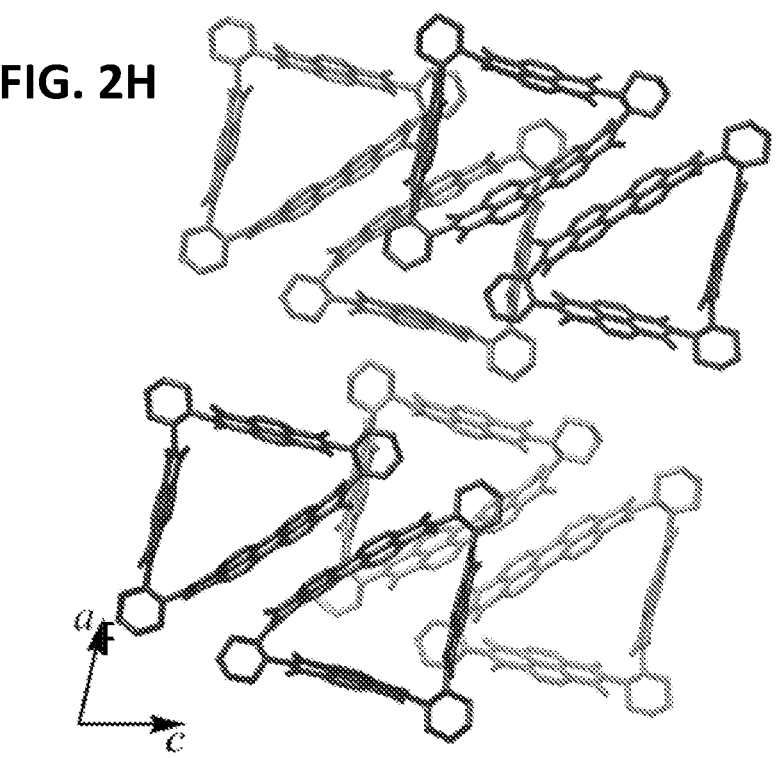
Figure 2I:
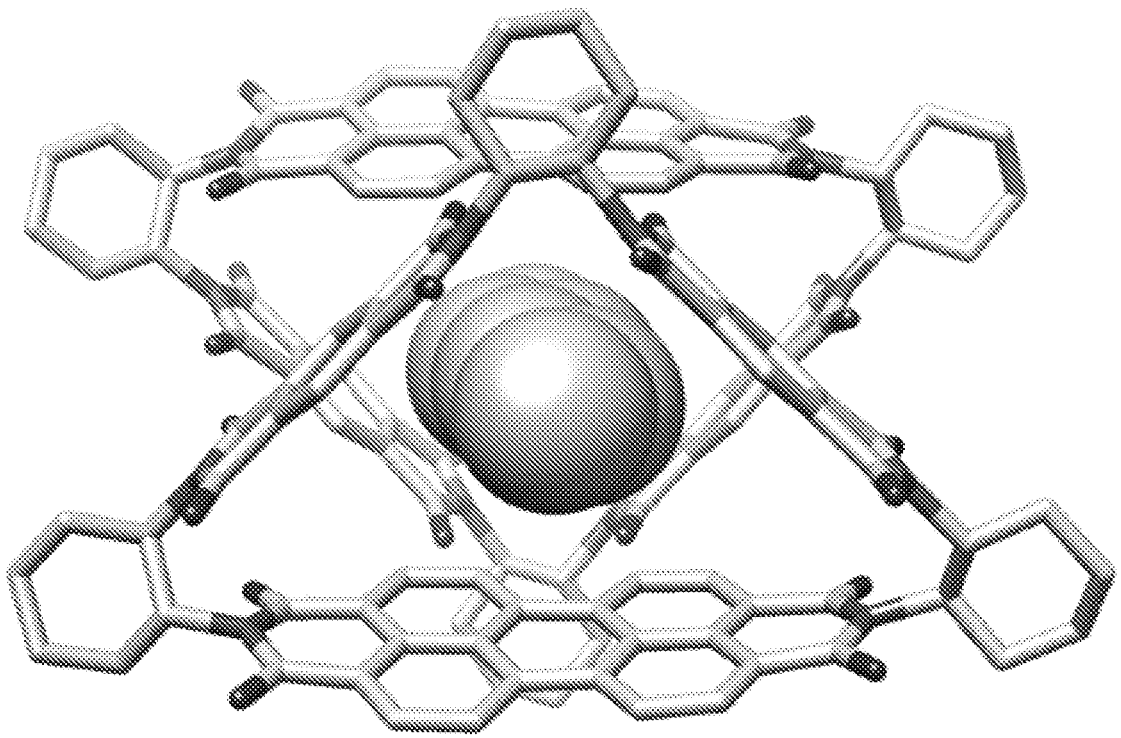
FIGS. 2I and 2J show single-crystal X-ray structures from a top (FIG. 2I) and side-on (FIG. 2J) views of (−)-2PMDI-1PDI-Δ forming a 2:1 inclusion complex with n-hexane molecule, depicted in space-filling representation, by means of multiple [C—H . . . π] interactions.
Figure 4A:
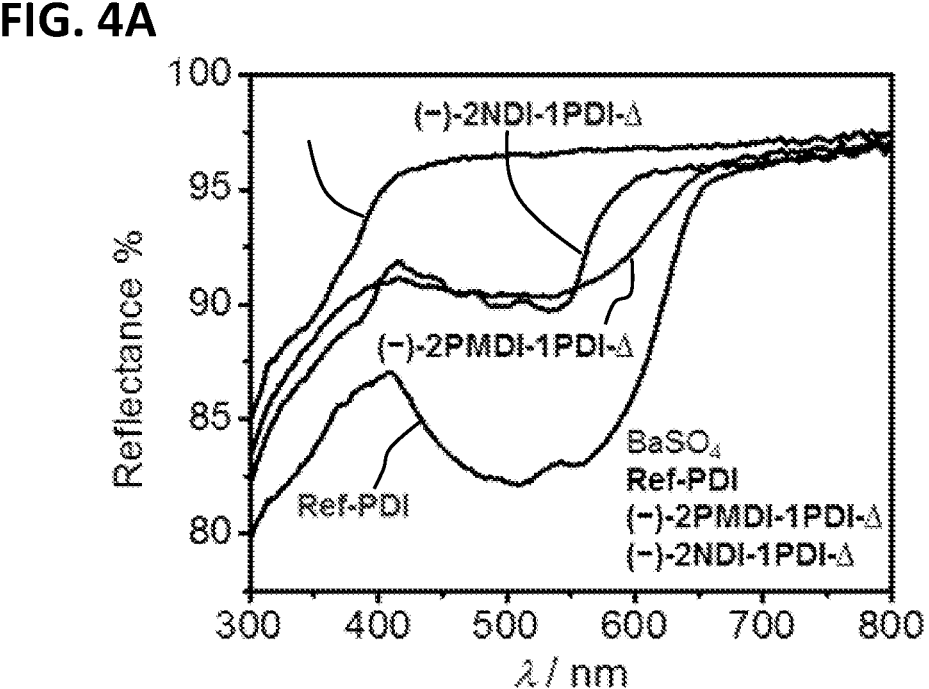
FIGS. 4A-4G shows photophysical studies of reference compound and isosceles triangles in the solid state.

Unlike the optical properties observed in solution, the optical properties of all three compounds in the solid state differ from one another (Table 1). The diffuse reflectance spectra of all three compounds in the solid state are shown in FIG. 4A. The linewidths of the spectral peaks in all three compounds are relatively broad with the loss of the well-resolved vibronic patterns found in solution. The observed differences in their solid state reflectance spectra are presumably a consequence of a complex combination of electronic transition dipole-dipole coupling as well as π-π overlap. It is noteworthy that the intermolecular π-π stacking between the neighboring molecules in the case of Ref-PDI is consecutive and uninterrupted in the solid state,[64] while the π-π stacking in the case of both the isosceles triangles is suppressed, as result of the formation of nearly cofacial discrete π-π dimers lacking any additional long-range noncovalent bonding interactions, on account of their unique rigid triangular geometries as evidenced by their solid-state (super)structures (FIGS. 2A-2Q).

Figure 4B:
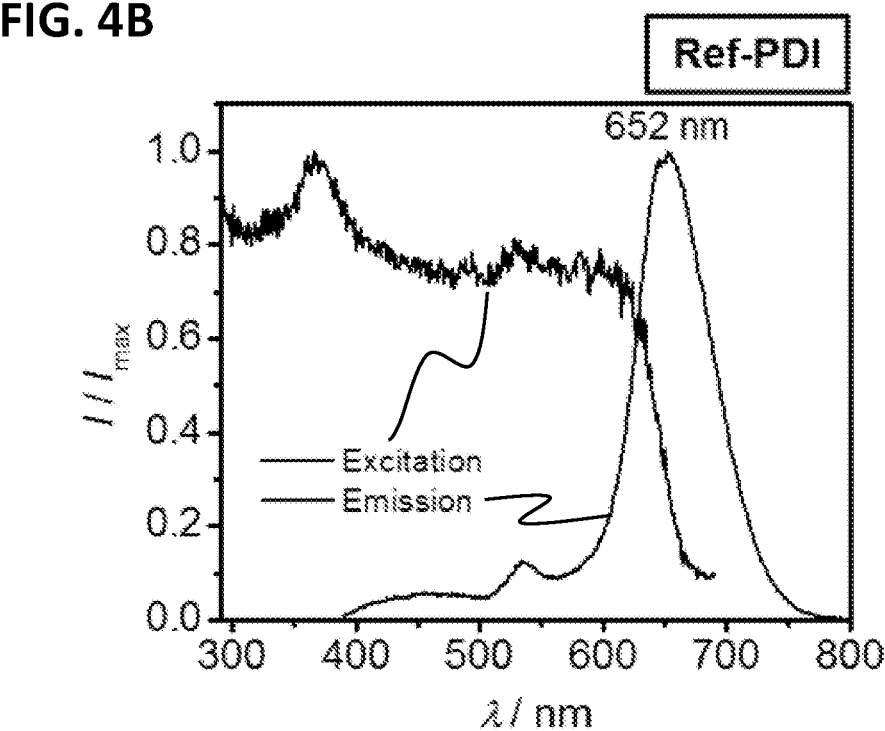
Figure 4C:
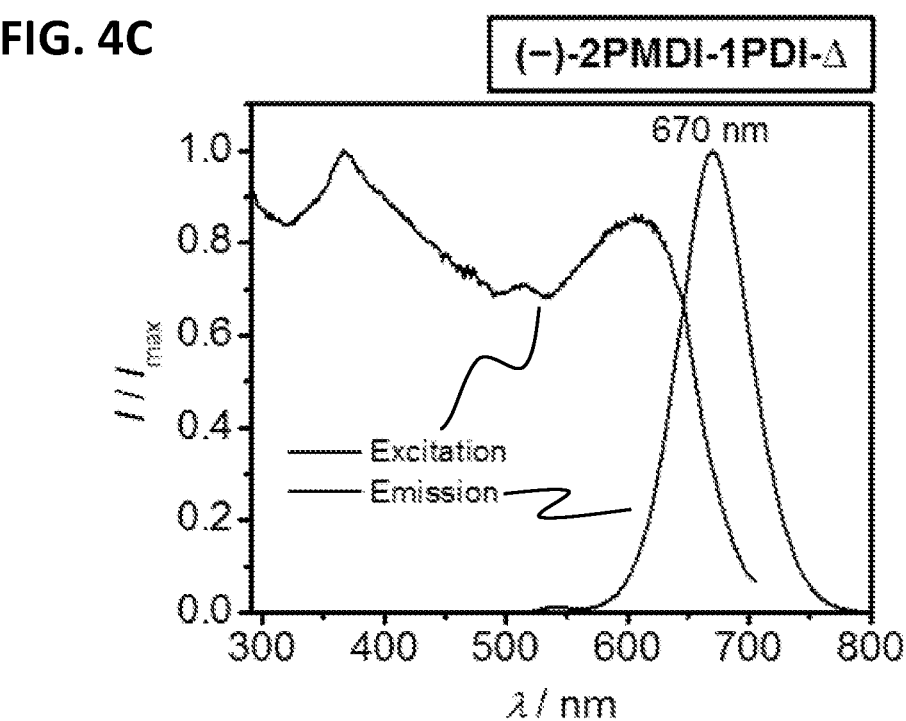
Figure 4D:
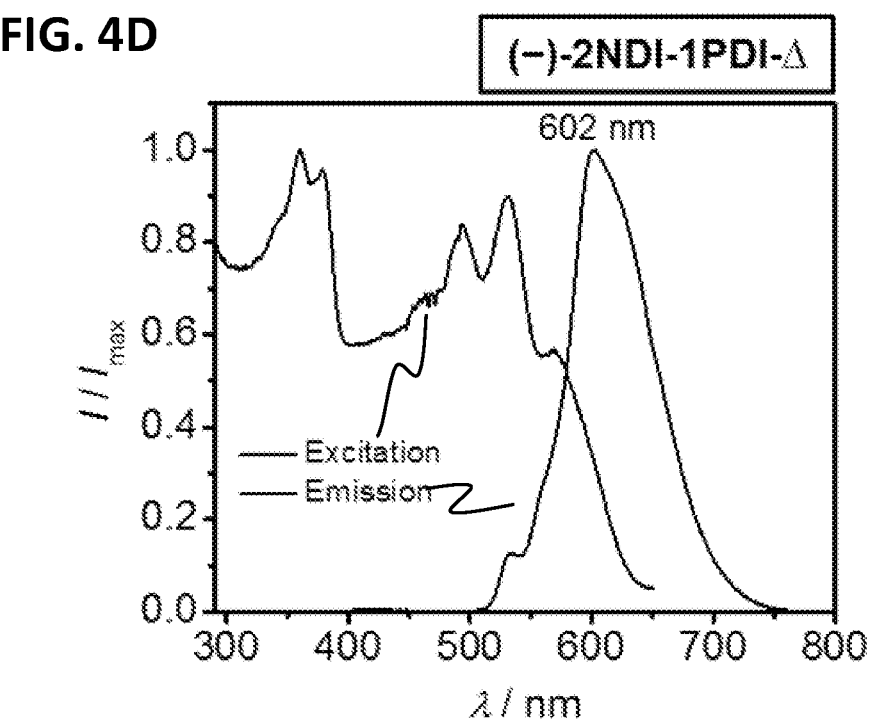
Figure 4G:
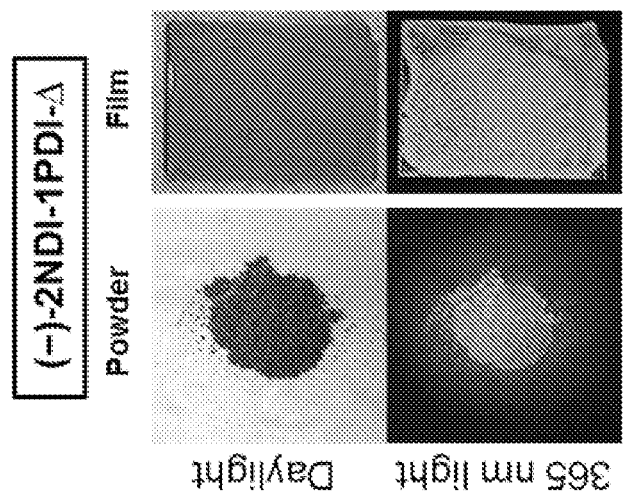
Figure 4F:
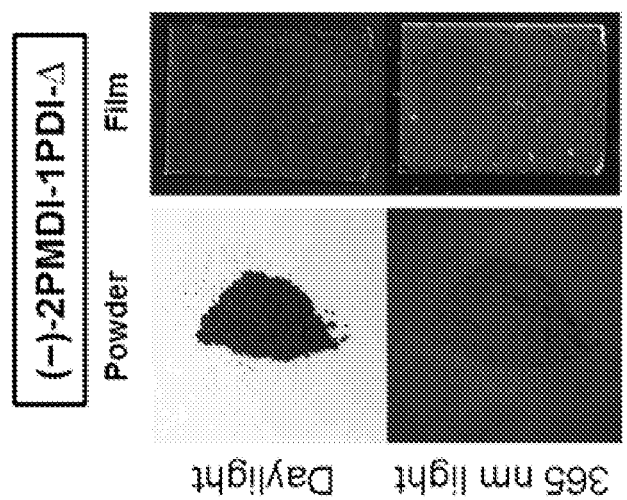
Figure 4E:
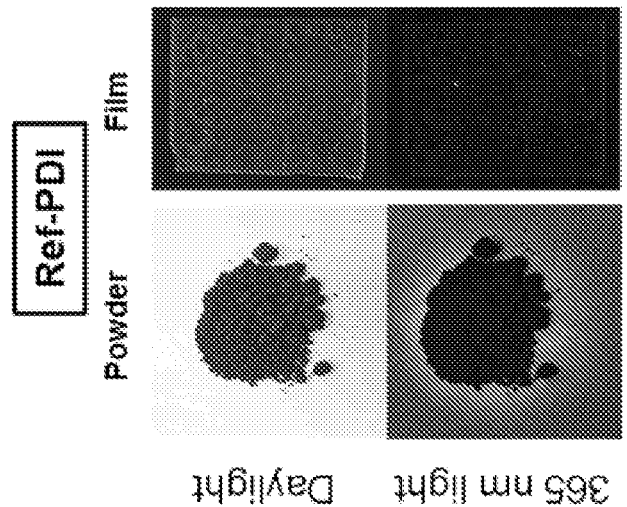
Figure 4H:
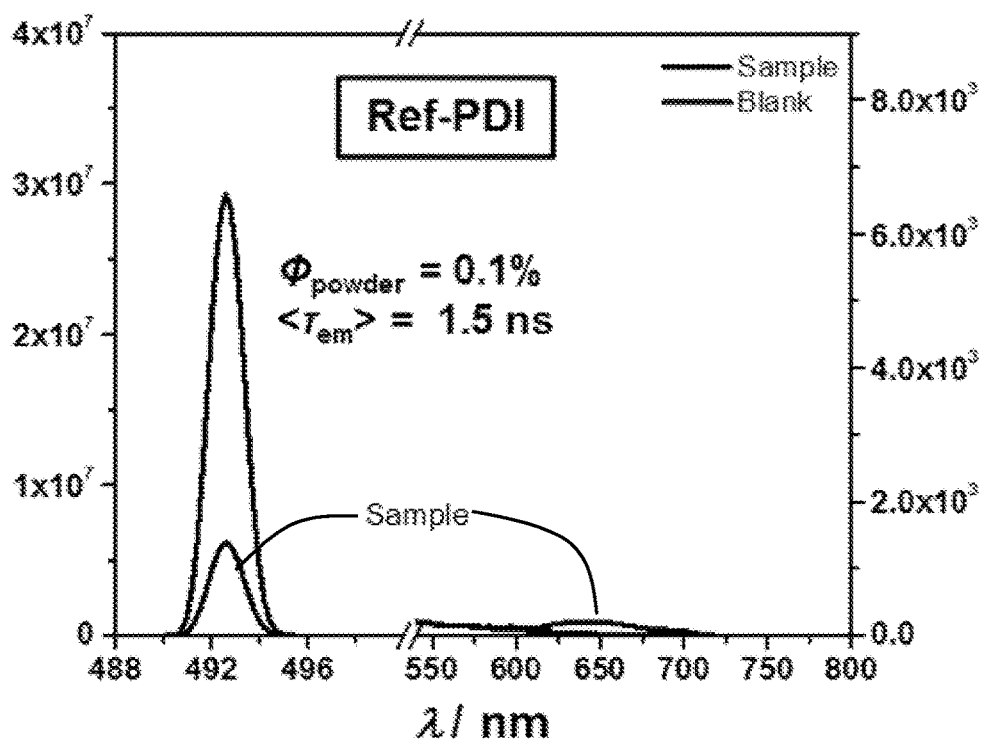
FIGS. 4H-4J show traces from the photoluminescence spectra of (FIG. 4H) Ref-PDI, (FIG. 4I) (−)-2PMDI-1PDI-Δ and (FIG. 4J) (−)-2NDI-1PDI-Δ in the solid-state used for measuring the absolute photoluminescence quantum yields ($\Phi_f$) in the solid state using an integrating sphere.
Figure 4I:
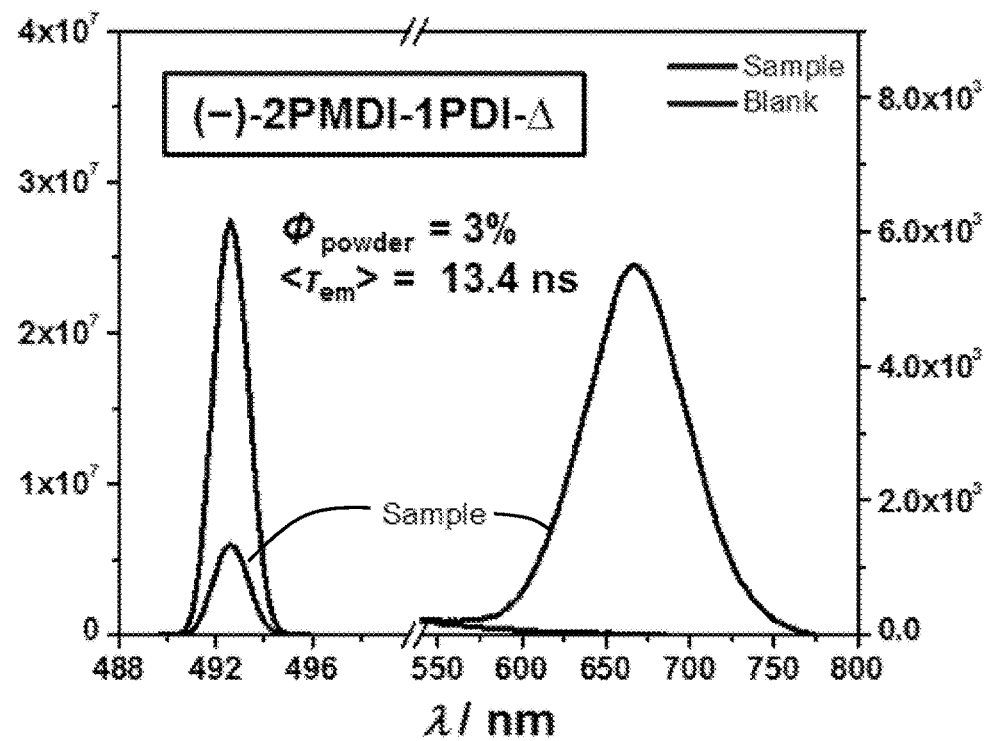
Figure 4J:
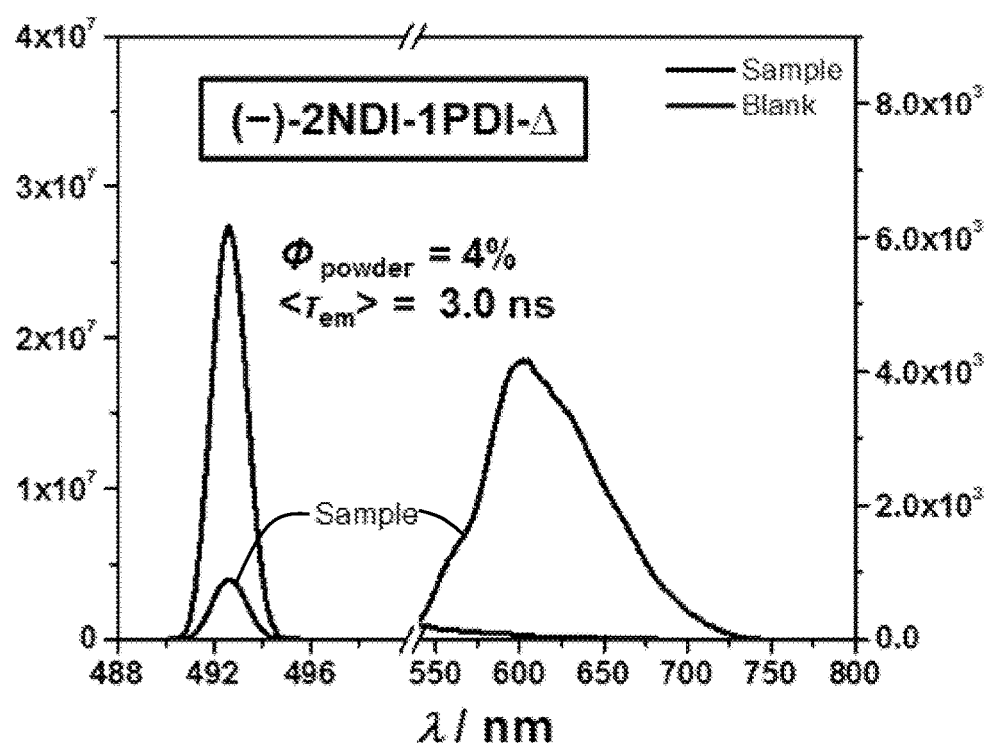

Unlike the excellent fluorescence properties observed in solution, the photoluminescence (PL) of all three compounds led (Table 1) to aggregation-caused quenching in the solid state. The PL spectra (FIGS. 4B-4D) of all three compounds displayed weak, red-shifted excimer emission bands at 652, 670 and 602 nm for Ref-PDI, (−)-2PMDI-PDI-Δ and (−)-2NDI-PDI-Δ, respectively. The photographs (FIGS. 4E-4G) of all three compounds in powder form as well as film coated on a glass substrate taken under 365 nm light irradiation reveal that (−)-2PMDI-1PDI-Δ and (−)-2NDI-1PDI-Δ show red and orange emission colors, respectively, while the emission of Ref-PDI is quenched almost completely. This variation in the emission maxima of all three compounds reflects the difference in electronic coupling between the two PDIs in the solid state structure that leads to excimer state stabilization. The greater π-π overlap of the PDI molecules observed in the crystal structure of (−)-2PMDI-1PDI-Δ relative to that of (−)-2NDI-1PDI-Δ is consistent with the larger redshift of the excimer emission from (−)-2PMDI-1PDI-Δ. As a consequence of long, continuous π-π stacking between neighboring Ref-PDI molecules, negligible photoluminescence quantum yields are observed for Ref-PDI, in both powder form ($\Phi_{powder}$=0.1%) and thin film ($\Phi_{film}$=0.2%). In contrast, the photoluminescence behavior is improved (Table 1 and FIGS. 4H-4J) for the isosceles triangles but the quantum yields are still low in the solid state for (−)-2PMDI-PDI-Δ ($\Phi_{power}$=3% and $\Phi_{film}$=2%) and (−)-2NDI-1PDI-Δ ($\Phi_{powder}$=4% and $\Phi_{film}$=2%).

Figure 1J:
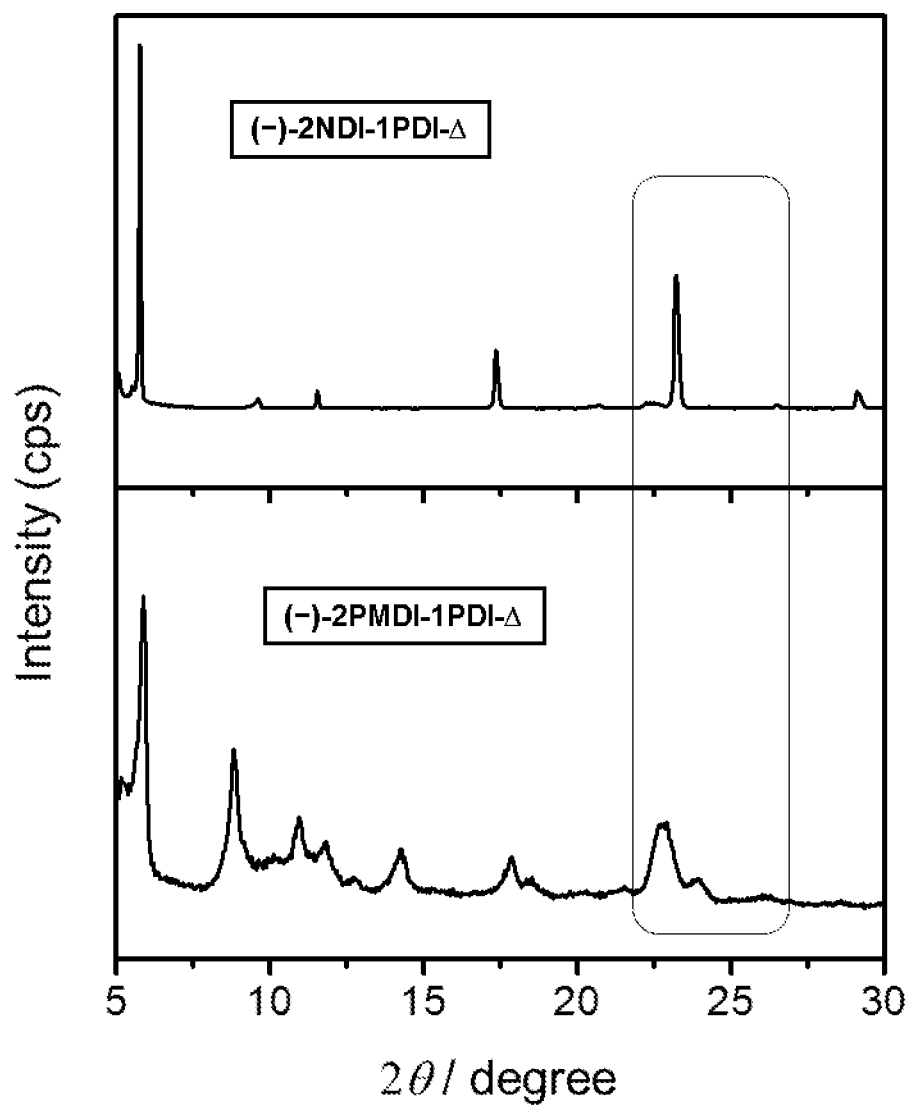
FIG. 1J shows the XRD patterns of the thin film samples prepared by drop casting $CH_2Cl_2$ solution of (−)-2NDI-1PDI-Δ (top) and (−)-2PMDI-1PDI-Δ (bottom) onto piranha-cleaned Si wafer. The highlighted region may suggest the possible intermolecular π-π stacking within the range of 3.2 to 3.7 Å between the curved, yet nearly co-facial, PDI units of the isosceles triangles.

Although the X-ray diffraction patterns obtained using the powder (FIGS. 1H and 1I) and thin film (FIG. 1J) samples of both the isosceles triangles at room temperature may suggest the peaks corresponding to intermolecular π-π stacking within the range of 3.2 to 3.7 Å between the aromatic units, this level of information was not sufficient to determine and compare specific molecular packing arrangements in the bulk samples with those observed (FIG. 2A-2S) by single-crystal XRD. It should be noted that the single-crystal XRD analyses reveal the random orientation of the discrete PDI-PDI π-dimers throughout the (super)structures in the case of both isosceles triangles and thus, we suppose it may be challenging to experimentally observe the XRD peaks characteristic of packing arrangements associated with π-π stacking in the powder or thin film samples. Based on the presence and the robustness of the nearly cofacial PDI π-π dimer packing motifs of the isosceles triangles in the presence of different solvents (FIGS. 2A-2Q) and even under solvent-free conditions (FIGS. 2R and 2S), we believe that the improvement in the photoluminescence quantum yields of (−)-2PMDI-1PDI-Δ and (−)-2NDI-1PDI-Δ—by about 10 to 40 times that of Ref-PDI—in the solid state is, however, a consequence of suppressing the global π-π stacking interactions defined by their unique structurally rigid triangular geometries.

Figure 5A:
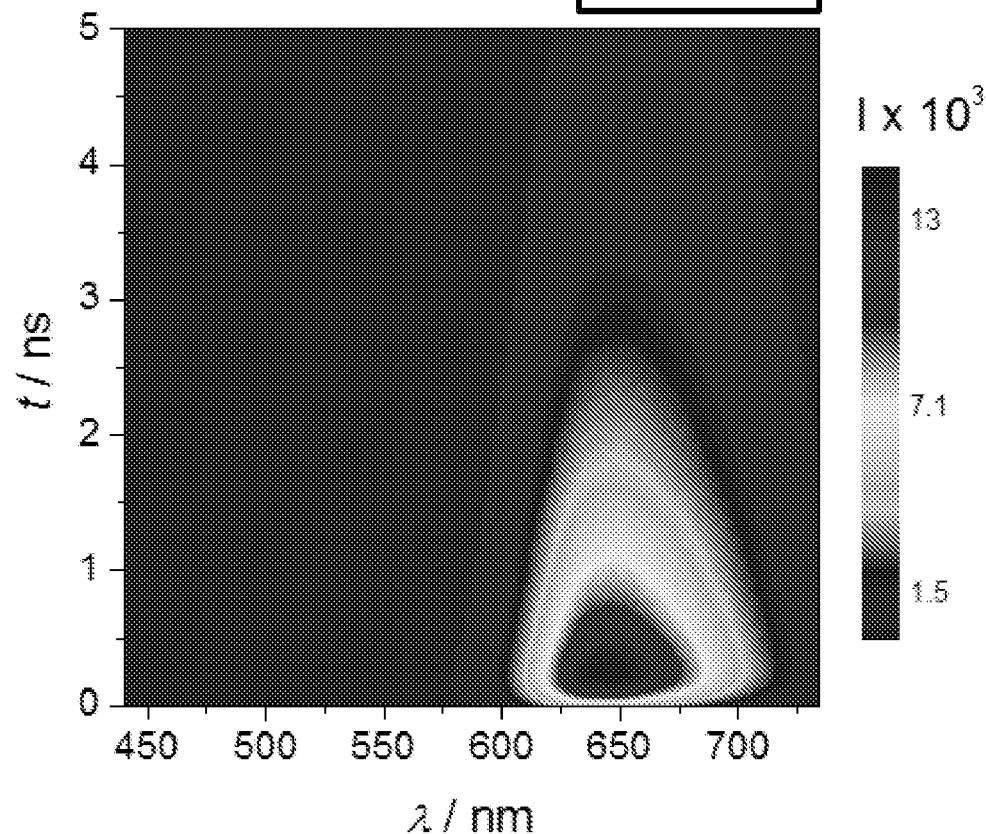
FIGS. 5A-5C shows solid-state time-resolved photoluminescence spectra of reference compound and isosceles triangles of Ref-PDI (FIG. 5A upper panel), (−)-2PMDI-1PDI-Δ (FIG. 5B upper panel) and (−)-2NDI-1PDI-Δ (FIG. 5C upper panel) recorded in the solid state at 298 K and the corresponding solid-state photoluminescence decay curves (corresponding middle panel) and the residuals (corresponding lower panel). The photoluminescence spectra of all three compounds were obtained with the excitation at 360 nm.
Figure 5A:
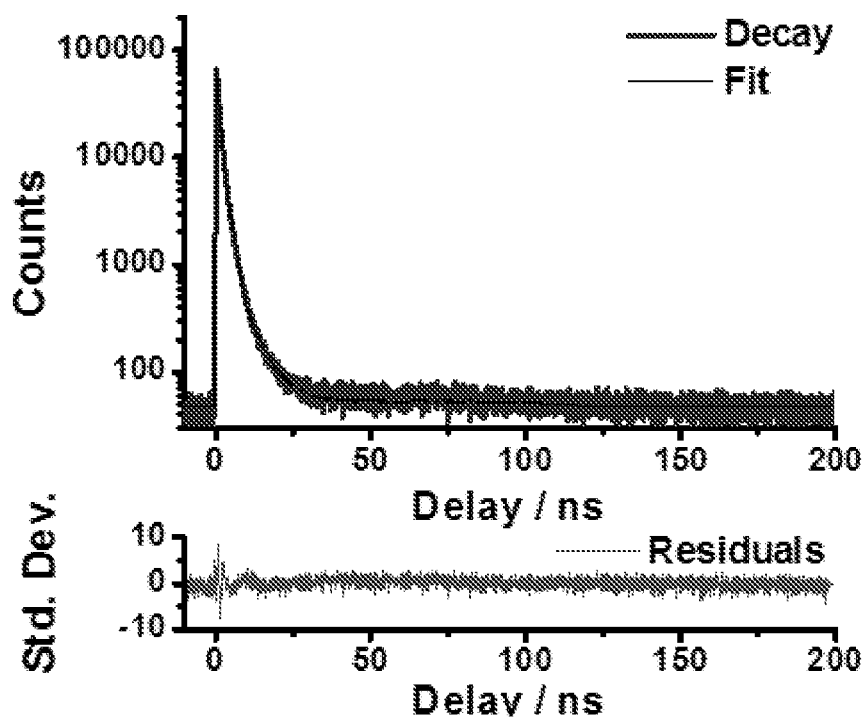
Figure 5B:
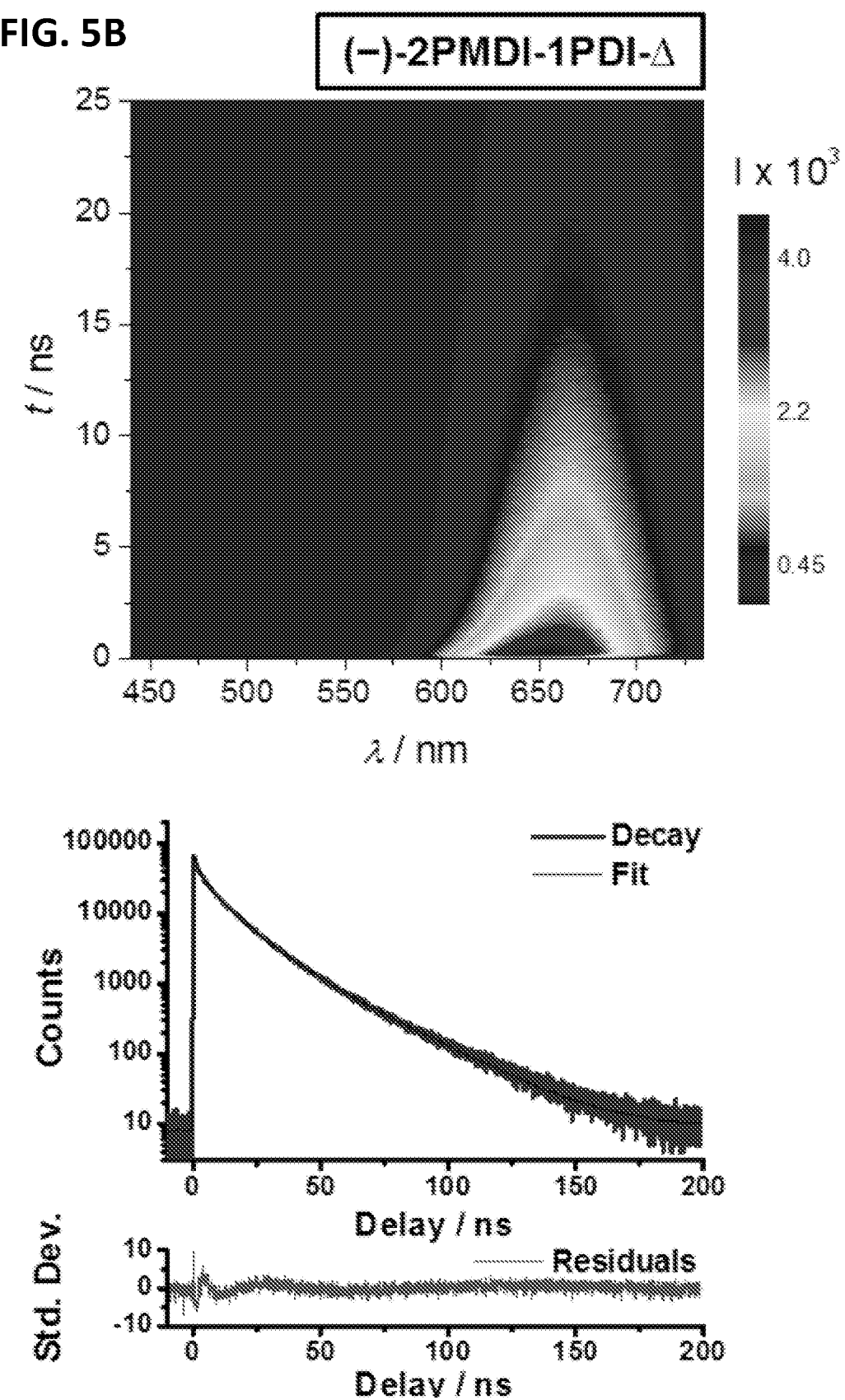
Figure 5C:
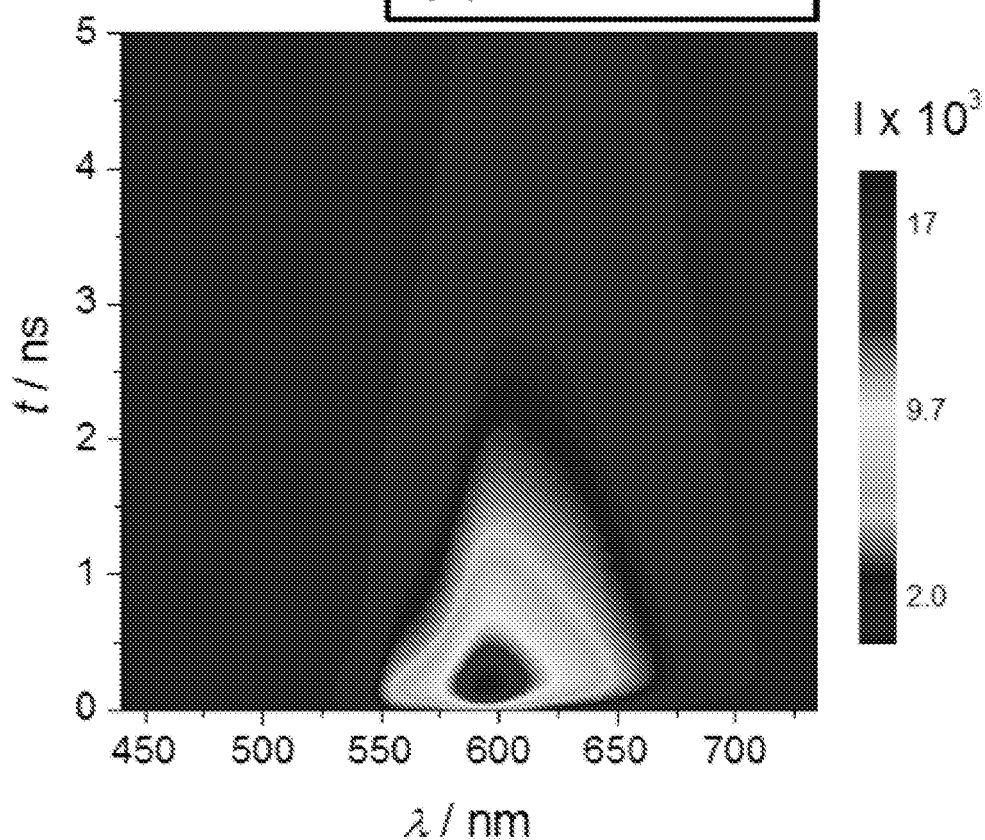
Figure 5C:
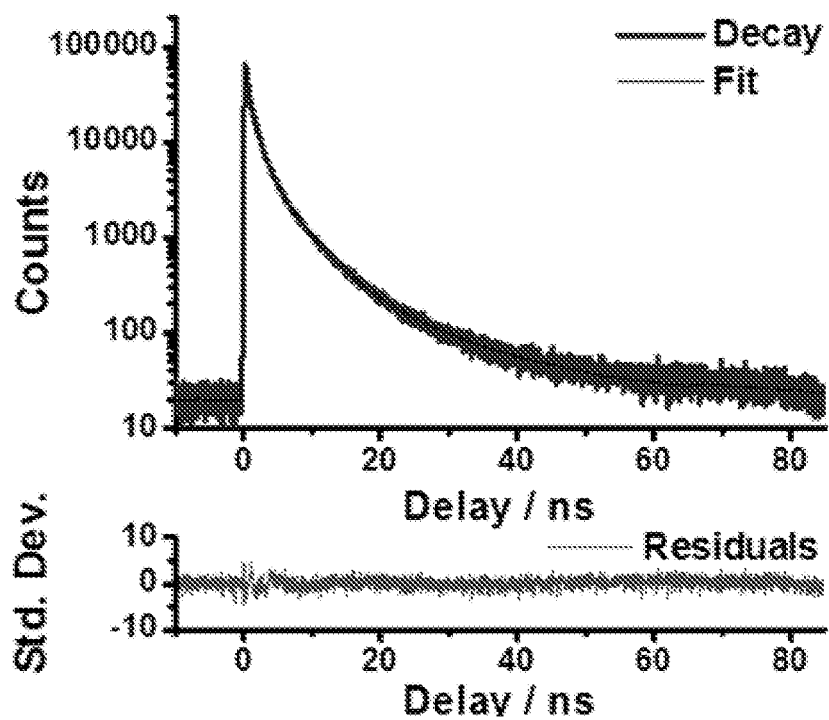

The solid-state excitation spectra of all compounds resemble their absorption spectra relatively well (FIGS. 4B-4C), suggesting that the emission comes from only one excited species. The presence of NDI vibronic patterns in the excitation spectra measured for (−)-2NDI-1PDI-Δ indicates that efficient energy transfer occurs between the excited singlet state of NDI and that of PDI subunit upon photoexcitation of the NDI subunits, even in the solid state. The excimer fluorescence of Ref-PDI and (−)-2NDI-1PDI-Δ in the solid state display (FIGS. 5A and 5C) multi-exponential decays with average lifetimes of $<\tau_{em}>$=1.5 and 3.0 ns, respectively, while the corresponding excimer fluorescence decay of (−)-2PMDI-1PDI-Δ exhibits (FIG. 5B) a longer multi-exponential decay with an average lifetime of $<\tau_{em}>$=13.4 ns, which again is consistent with the more highly constrained cofacial geometry of the PDI-PDI dimers in (−)-2PMDI-1PDI-Δ.

Frontier Molecular Orbitals of Isosceles Triangles

Figure 2J:
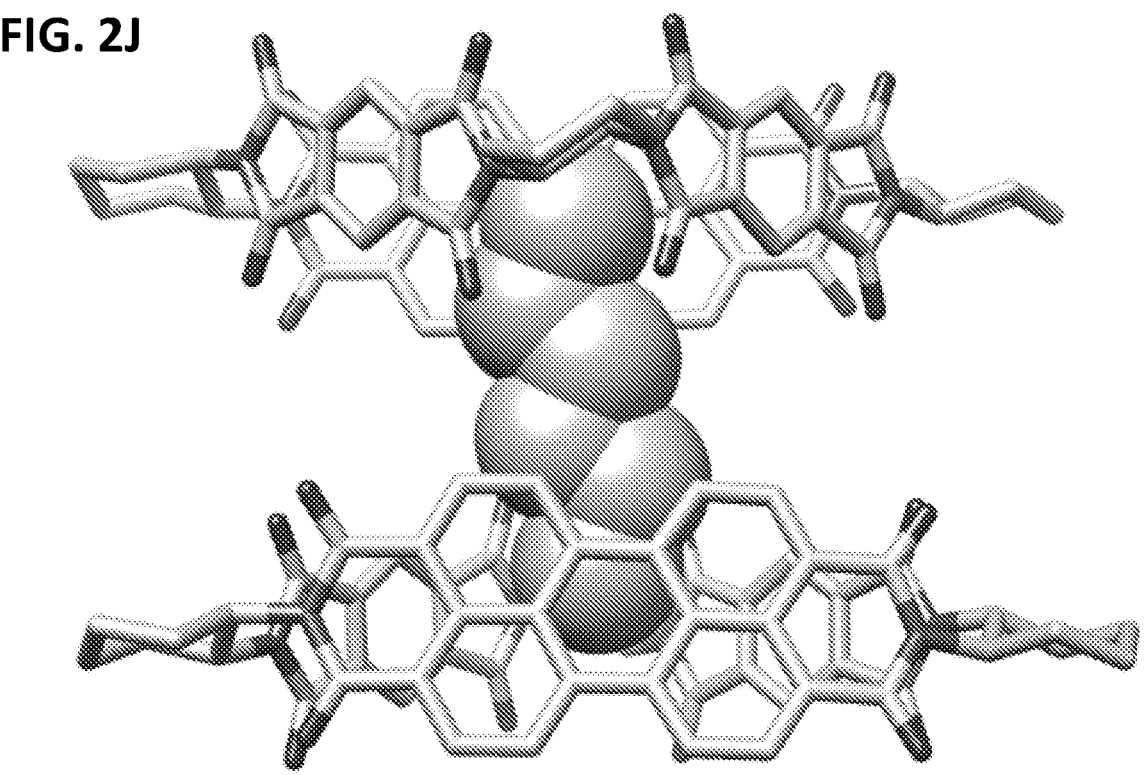
Figure 2K:
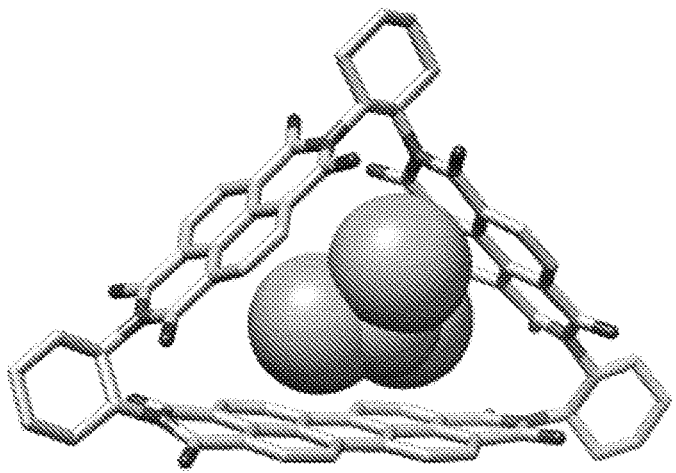
FIGS. 2K and 2L show single-crystal X-ray structures from a top (FIG. 2K) and side-on (FIG. 2L) views of π-π stacking dimers of (−)-2NDI-1PDI-Δ where $CHCl_3$ molecules, depicted in space-filling representation, are bound to their cavities stabilized by multiple [Cl . . . π] interactions (~3.4 Å) with π-surfaces.
Figure 2K:
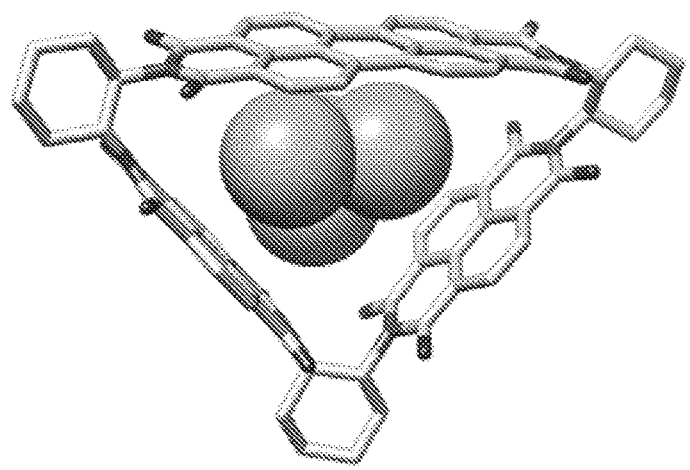
Figure 2L:
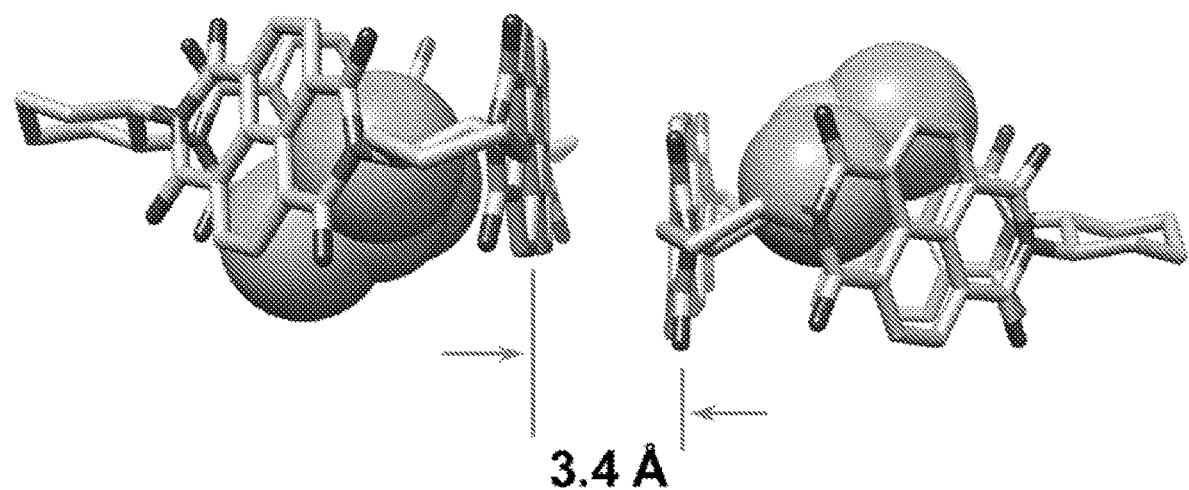
Figure 2M:
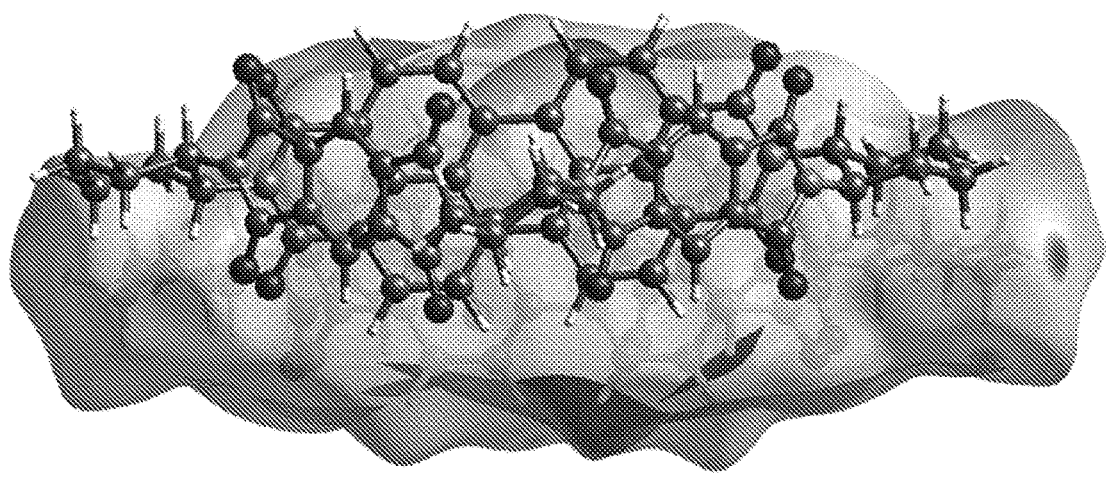
FIGS. 2M and 2N show the Hirshfeld surfaces of the π-π dimers of (−)-2PMDI-1PDI-Δ (FIG. 2M) and (−)-2NDI-PDI-Δ (FIG. 2N) mapped with $d_{norm}$. The [π . . . π] interactions contribute 12.2% to the Hirshfeld surface of (−)-2PMDI-1PDI-Δ and 12.1% to the Hirshfeld surface of (−)-2NDI-1PDI-Δ, respectively.
Figure 2N:
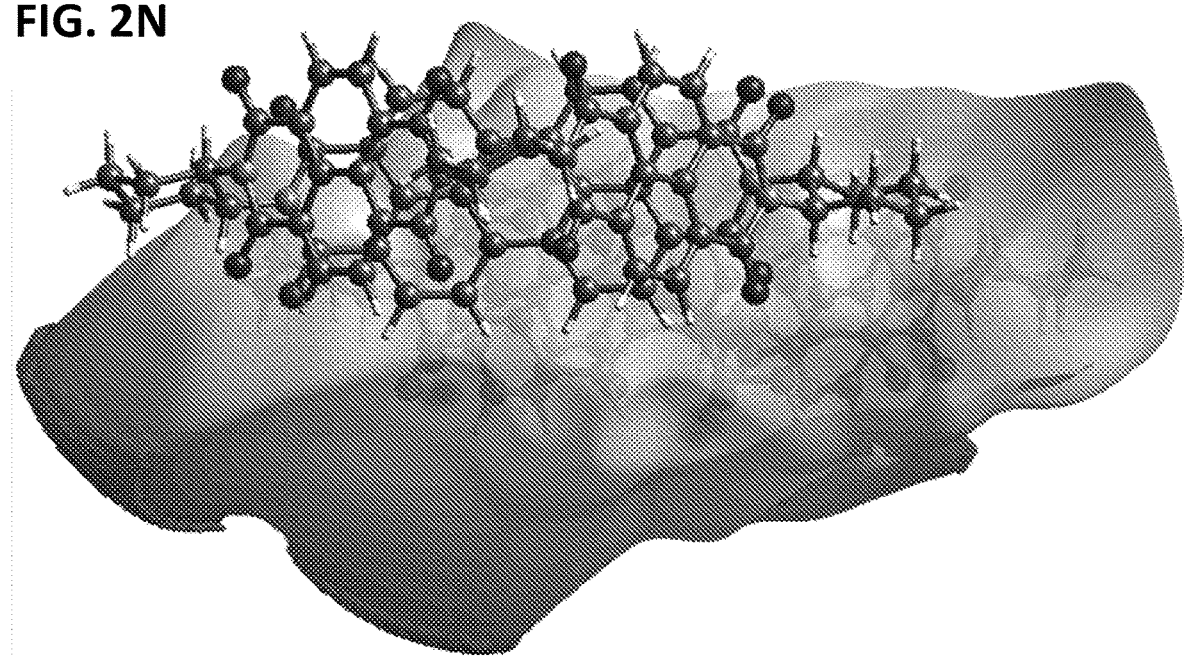
Figure 2R:
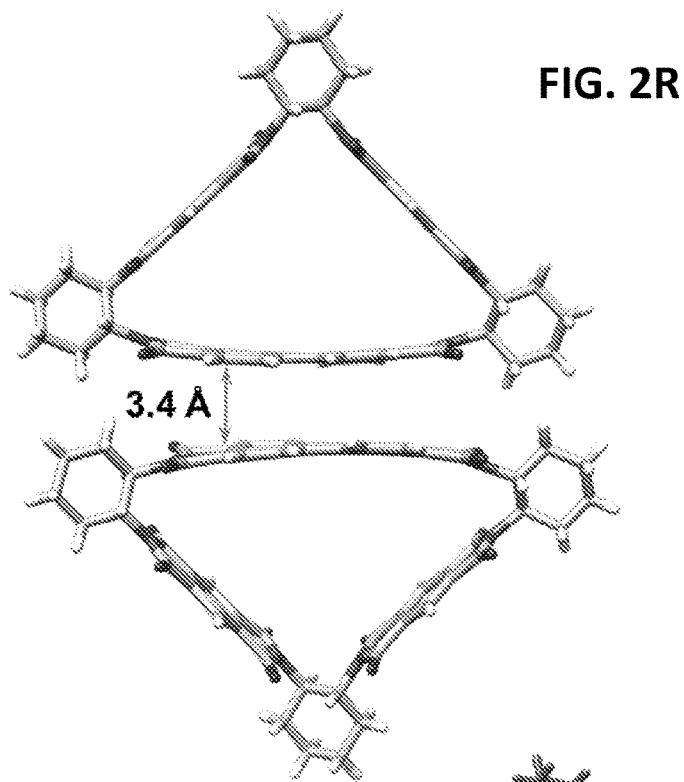
FIGS. 2R and 2S show solvent-free single-crystal X-ray structures from a top view of π-π stacking (~3.4 Å) dimer of (−)-2PMDI-1PDI-Δ (FIG. 2R) and a view along c-axis of the unit cell of (−)-2PMDI-1PDI-Δ (FIG. 2S). It should be noted that the solvent-free single crystals of (−)-2PMDI-1PDI-Δ were obtained by air drying the single crystals grown by slow vapor diffusion of n-hexane in $CHCl_3$ solution, in order to investigate the role of solvents on the formation of discrete PDI-PDI π-dimers in the solid state. Even under solvent-free conditions, it was observed that the PDI-PDI π-dimers remained intact which exhibit similar packing arrangements and the unit cell parameters before and after the evaporation of $CHCl_3$ from the single crystals.
Figure 2S:
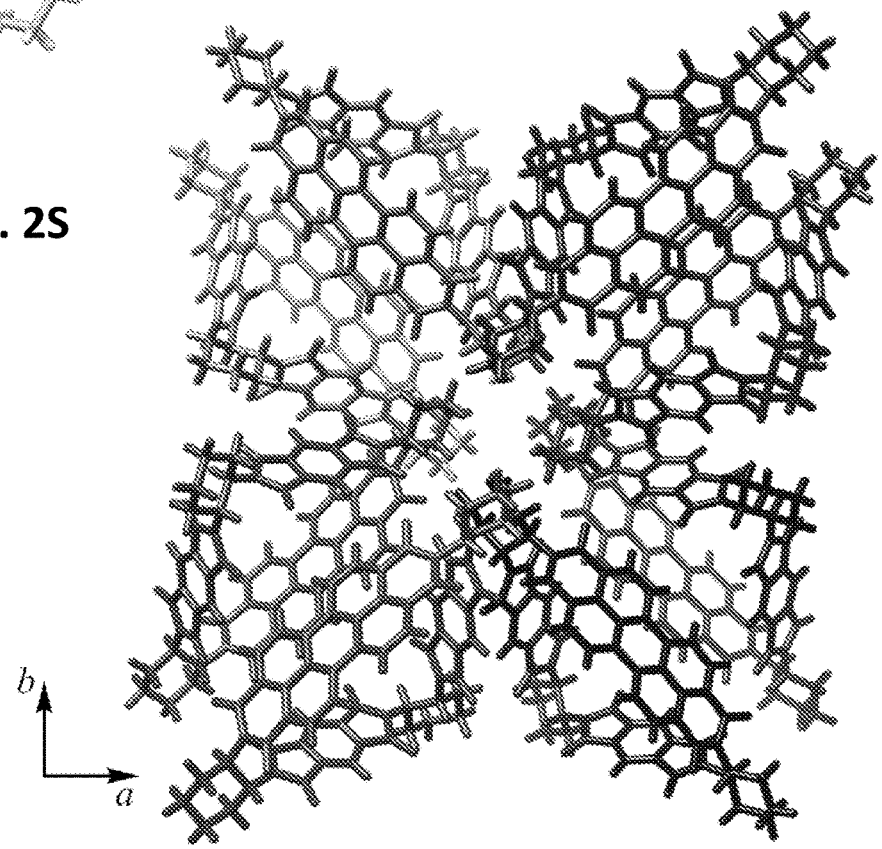
Figure 6A:
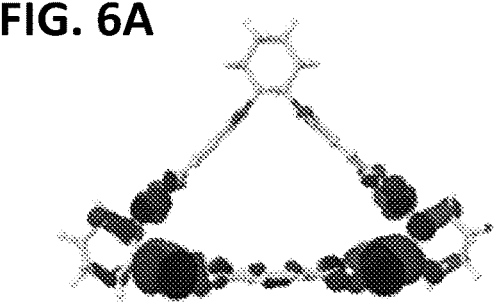
FIGS. 6A-6L show quantum mechanical calculations on the molecular orbitals of isosceles triangles.
Figure 6B:
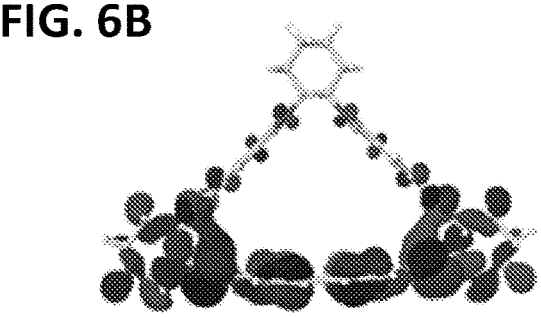
Figure 6C:
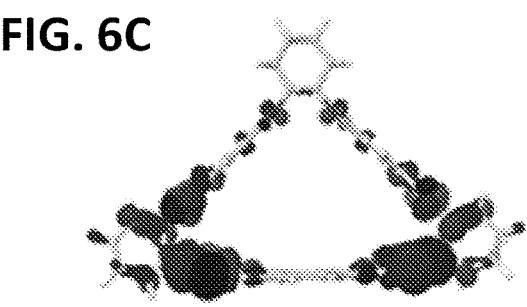
Figure 6D:
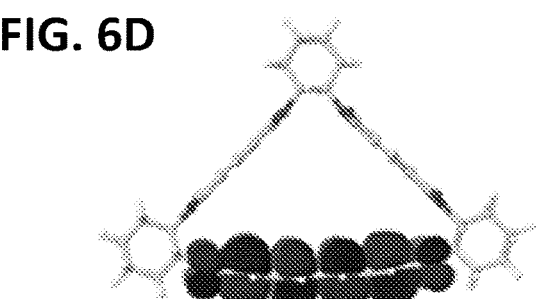
Figure 6E:
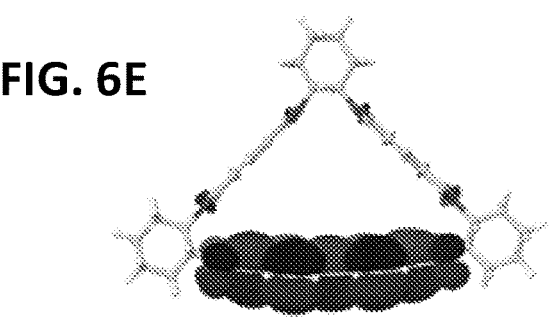
Figure 6F:
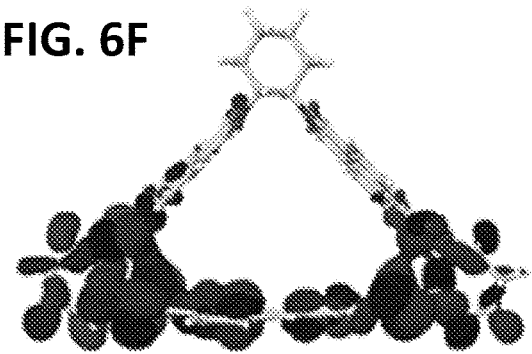
Figure 6G:
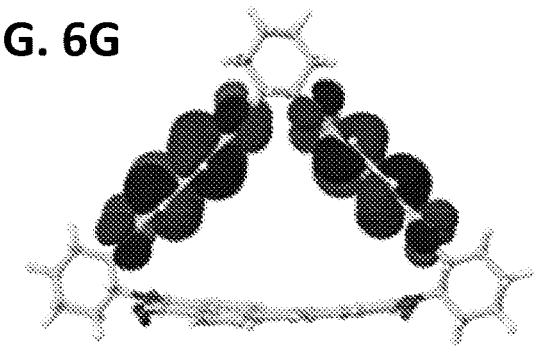
Figure 6H:
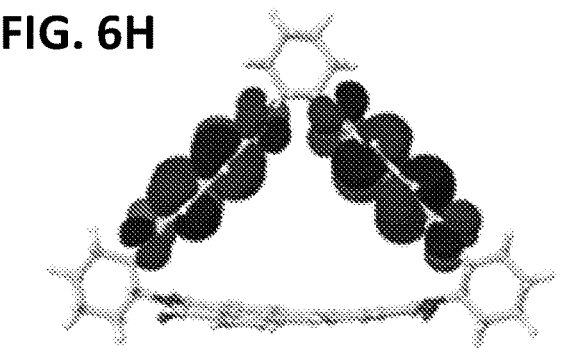
Figure 6I:
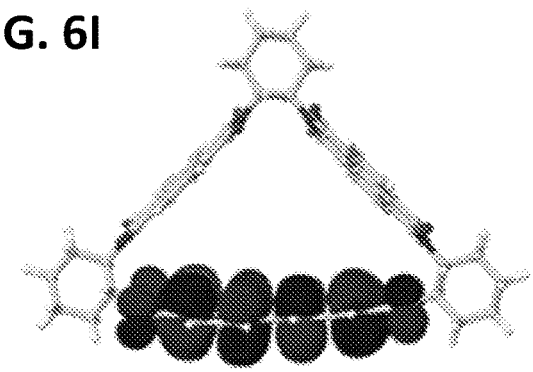
Figure 6J:
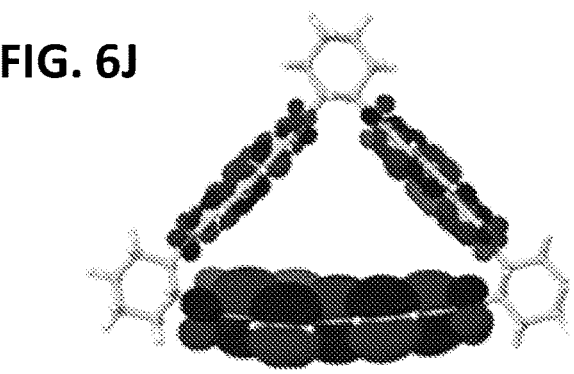
Figure 6:
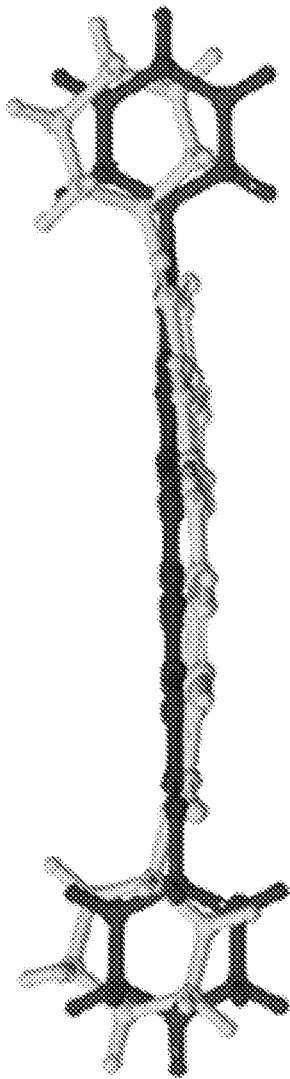
FIGS. 6M and 6N show simulated UV/Vis spectra of (FIG. 6M) (−)-2NDI-1PDI-Δ and the corresponding HOMO-LUMO electronic transitions at 400 and 560 nm, (FIG. 6M) (−)-2PMDI-1PDI-Δ and the corresponding HOMO-LUMO electronic transitions at 560 nm. Please note the calculated wavelengths for the HOMO-LUMO electronic transitions are longer than the experimental values, which is expected since TD-DFTB usually sub-estimates the eigenvalues
Figure 6:
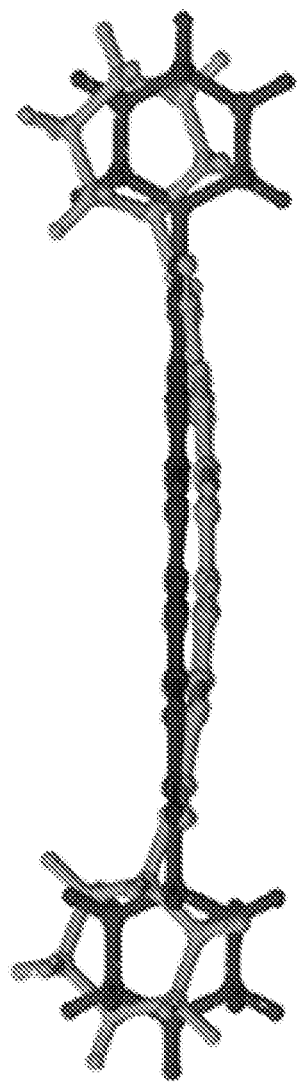
Figure 6M:
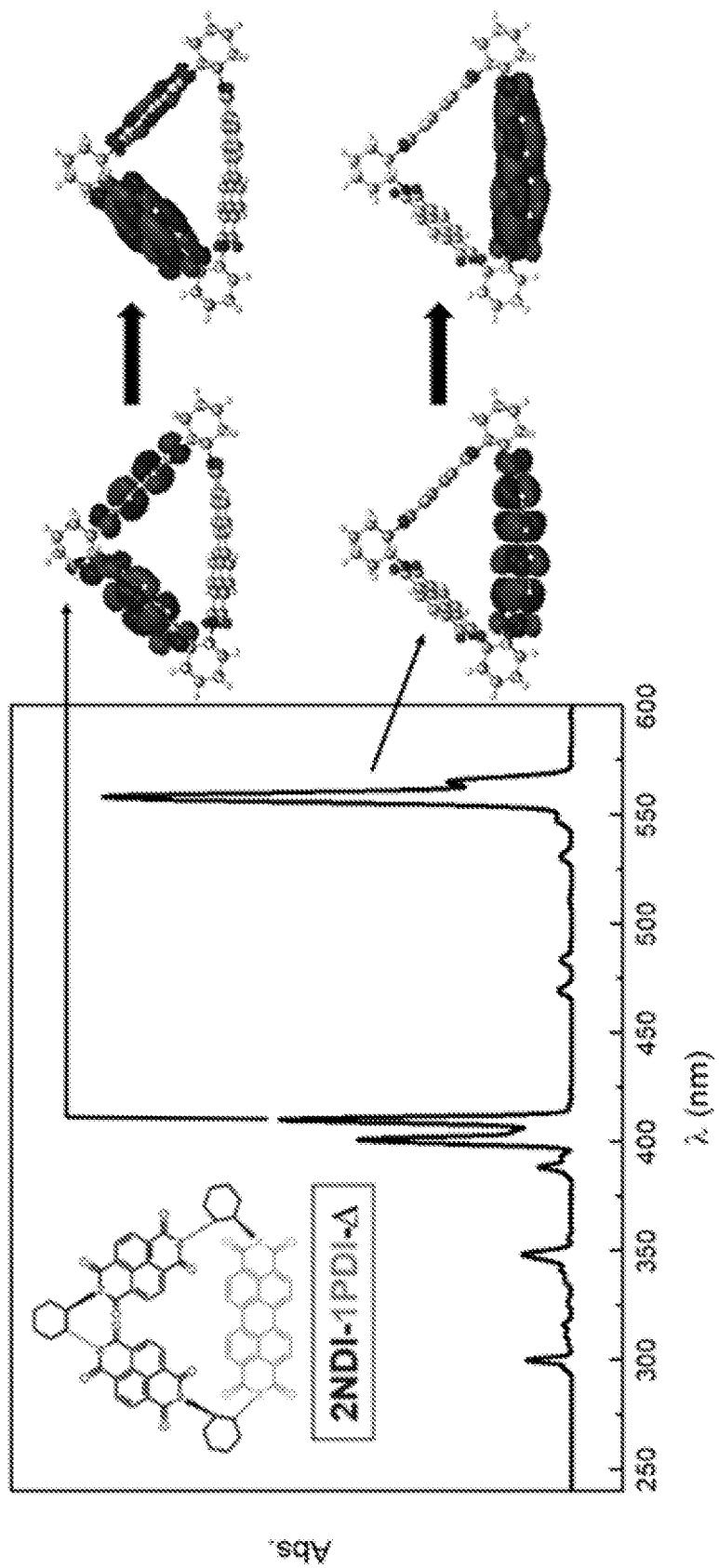
Figure 6N:
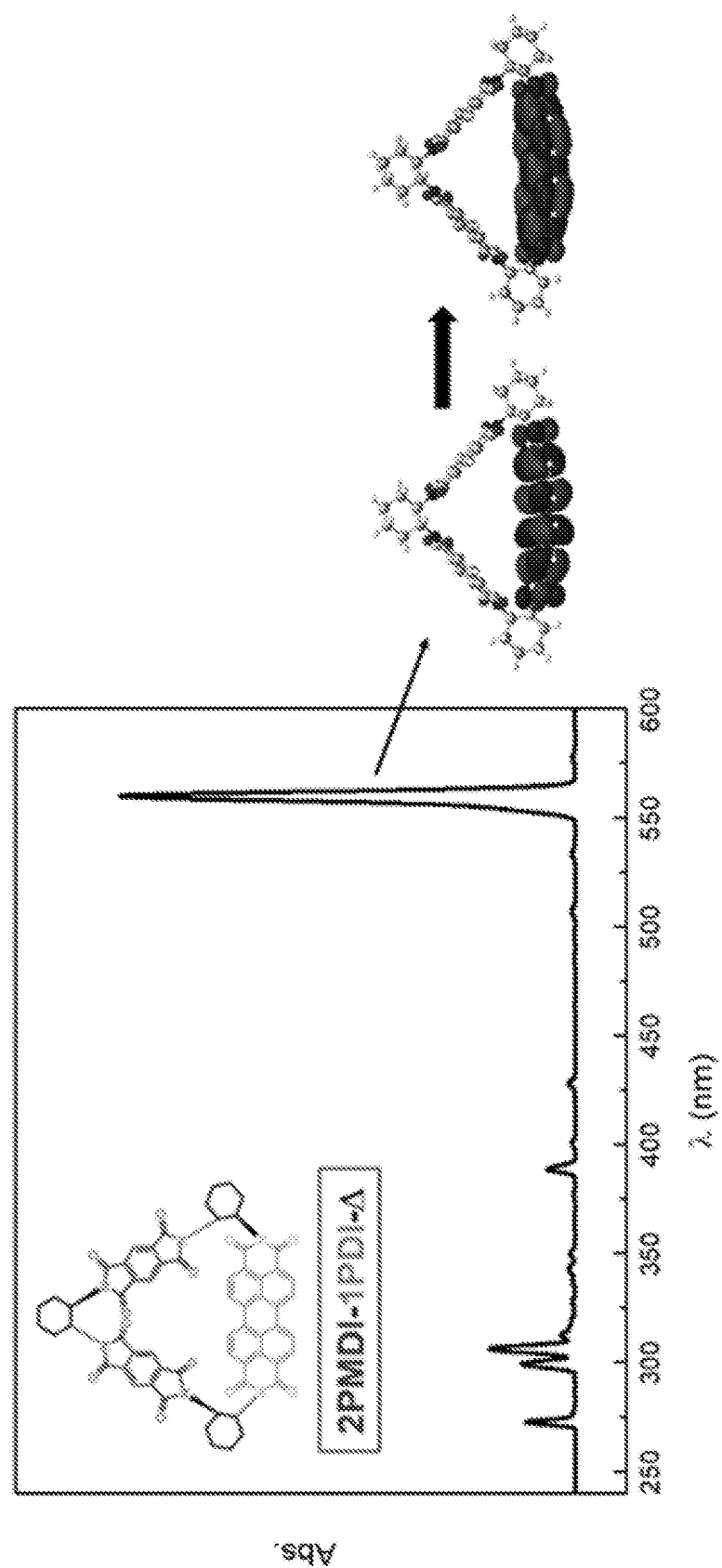

In order to obtain deeper insight into the electronic properties of these highly fluorescent isosceles triangles, we performed density functional theory (DFT) quantum mechanics (QM) calculations at the M06-2X level of theory using the 6-311G(d,p) basis set and including Poisson Boltzmann Continuum Solvations with $CH_2Cl_2$ as the solvent. All the calculations (FIGS. 6A-6L) include post-stage D3 van der Waals corrections.[65,66] Our calculations find that in (−)-2PMDI-1PDI-Δ the frontier molecular orbitals (FMOs) of the HOMO and LUMO levels are located only on the PDI subunit (FIGS. 6D and 6E), while in (−)-2NDI-1PDI-Δ the LUMO not only located on the PDI subunit but partially delocalized onto the two NDI subunits as well (FIGS. 6I and 2J). The electronic transitions for both the isosceles triangles were calculated using a tight-binding approximation of time-dependent density functional theory (TD-DFTB). Additionally, the simulated UV/Vis spectra (FIGS. 6M and 6N) show that the $S_1 \leftarrow S_0$ electronic transitions around 560 nm correspond to transitions from the HOMO to LUMO located on the PDI subunits. Additionally, the graphical representations obtained from our calculations (FIGS. 6K and 6L) show that the PDI planes of both isosceles triangles are significantly curved when compared to the fully relaxed PDI component of Ref-PDI, presumably as a consequence of rigidity and strain (ΔE~11.8 kcal mol$^{-1}$) associated with their cyclic triangular geometries, an observation which is consistent with the single-crystal XRD data.

Cyclic Voltammetry (CV)

In order to evaluate the potential applicability of the isosceles triangles in electronic devices, we investigated the electrochemical characteristics of (−)-2PMDI-1PDI-Δ and (−)-2NDI-1PDI-Δ by CV (FIG. 7A) and differential pulse voltammetry (DPV, FIG. 7B), and compared these results with those of the monomeric reference compounds, Ref-PMDI, Ref-NDI and Ref-PDI. The CVs of the monomeric reference compounds in $CH_2Cl_2$ exhibited two distinct reversible one-electron redox waves with half-wave potentials at (i) −927 and −1527 mV vs Ag/AgCl for Ref-PMDI, (ii) −709 and −1131 mV for Ref-NDI, and (ii) −605 and −794 mV for Ref-PDI, corresponding to the formation of radical anions and the dianions, respectively. Strikingly, the CV of (−)-2PMDI-1PDI-Δ displayed (FIG. 7A) four distinct redox processes involving a total of six-electrons namely, (i) two sequential and distinct reversible one-electron waves at −566 and −832 mV, corresponding to the formation of PDI$^-$ and PDI$^{2-}$, respectively, (ii) a reversible two-electron wave at −1008 mV, corresponding to the formation of two PMDI$^-$ radical anions and (iii) finally, a quasi-reversible two-electron process at −1764 mV, corresponding to the formation of two PMD$^{2-}$ dianions. In addition, the CV of (−)-2NDI-1PDI-Δ exhibited (FIG. 7A) five distinct redox processes containing six electrons in total—namely, (i) a reversible one-electron wave at −572 mV, corresponding to the formation of a singly reduced PDI$^-$ radical anion, (ii) a reversible two-electron wave at −749 mV, corresponding to the formation of two singly reduced NDI$^-$ species, (iii) a reversible one-electron wave at −960 mV, corresponding to the formation of PDI$^{2-}$, and (iv) finally, two reversible one-electron waves at −1331 and −1479 mV, corresponding to the formation of two NDI$^{2-}$ dianions. It is worth noting that the unambiguous assignment of the peaks corresponding to the mono radical anionic states of all PDI and NDI subunits present in (−)-2NDI-1PDI-Δ was confirmed by spectroelectrochemistry (FIG. 7C). Thus, the availability of multiple easily accessible reversible redox states for both isosceles triangles demonstrates their potential applicability as electron accumulation materials.

EPR and ENDOR Spectroscopies

Since the CV data (FIG. 7A) indicated that the monoradical states of PDIs could be accessed much more easily than those of the NDIs or PMDIs, we confirmed this by EPR and ENDOR spectroscopies and also further investigated whether the unpaired electron of the PDI subunit is shared among the adjacent PMDI or NDI subunits within the isosceles triangles. While the EPR spectrum (FIG. 7D) of [(−)-2PMDI-1PDI-Δ]$^{·-}$ is nearly identical to that of [Ref-PDI]$^{·-}$ with similar spectral widths and number of lines, the EPR spectrum (FIG. 7D) of [(−)-2NDI-1PDI-Δ]$^{·-}$ is narrowed compared to that of [Ref-PDI]$^{·-}$, corresponding to a decrease in the magnitude of the nuclear hyperfine interactions. These results indicate that the unpaired electron is localized only on the PDI subunits in the case of [(−)-2PMDI-1PDI-Δ]$^{·-}$ but partially shared with the adjacent NDI subunits in the case of [(−)-2NDI-1PDI-Δ]$^{·-}$. Similarly, the ENDOR spectrum (FIG. 7E) of [(−)-2PMDI-1PDI-Δ]$^{·-}$ has equal isotropic hyperfine coupling constants ($a_H$) compared to that of [Ref-PDI]$^{·-}$, once again indicating that the unpaired electron is isolated within the PDI subunits. On the other hand, the ENDOR spectrum (FIG. 7E) of [(−)-2NDI-1PDI-Δ]$^{·-}$ exhibits a decrease in its hyperfine coupling constant by about 15% compared to those of [Ref-PDI]$^{·-}$ and [(−)-2PMDI-1PDI-Δ]$^{·-}$, suggesting a small degree of electron sharing with the adjacent NDI subunits on the time scale (>10$^7$ s$^{-1}$) of the electron-nuclear hyperfine interaction. All these observations strongly indicate that (i) the sequential reductions of the PDI subunit of (−)-2PMDI-1PDI-Δ into its monoradical and the dianionic states can be easily accessed without being interrupted by its cyclic N-substituents, and (ii) the unpaired electron in [(−)-2PMDI-1PDI-Δ]$^{·-}$ is completely localized on the PDI subunit in a fashion similar to that of monomeric Ref-PDI.

SUMMARY

We have demonstrated the synthesis of two isosceles triangles-namely, (−)-2PMDI-1PDI-Δ and (−)-2NDI-1PDI- Δ-based on a one of the first of its kind designs, wherein one large and two small planar π-conjugated aromatic diimides are introduced into rigid chiral cyclic structures, incorporating three (RR)-trans-1,2-cyclohexanediamines. The two PDI-based isosceles triangles have rigid geometries with lower symmetries ($C_2$ point groups), relative to those ($D_3$ point groups) of the equilateral triangles [(−)-3NDI-Δ and (−)-3PMDI-Δ], as evidenced by the expected differences in their $^1H$ and $^{13}C$ NMR spectra. Their solid-state (super) structures show that geometrically protected PDI fluorophores of the isosceles triangles can only undergo intermolecular PDI-PDI π-stacking to form dimers because of the absence of any additional long-range noncovalent bonding interactions. Quantum mechanical calculations reveal that both the isosceles triangles consist of (i) conformationally rigid structures as indicated by their high intramolecular rotational barriers and (ii) significantly curved PDI shapes relative to the fully relaxed PDI plane of Ref-PDI. This unusual formation and packing arrangement, associated with the molecular rigidity, of the isolated PDI-PDI π-dimers of the isosceles triangles have a significant influence on their photoluminescence properties in the solid state. The solid-state photoluminescence quantum yields observed for the excimer states of (−)-2PMDI-1PDI-Δ and (−)-2NDI-1PDI-Δ are about 10 to 40-fold larger compared with that of Ref-PDI. The fluorescence emission spectra also suggest that efficient intramolecular energy transfer occurs between the adjacent NDI and PDI subunits of (−)-2NDI-1PDI-Δ. Such variations in the photophysical properties observed between the monomeric reference compound and the two isosceles triangles form a basis for the rational design of highly efficient fluorescent organic materials for applications in optoelectronic and photonic devices. Also, both (−)-2PMDI-1PDI-Δ and (−)-2NDI-1PDI-Δ are chiral molecules with strong fluorescence emissions, and hence they would be expected to exhibit circularly polarized luminescence (CPL). Moreover, the electrochemical properties investigated by CV indicate that Ref-PDI can only produce two redox states, while (−)-2PMDI-1PDI-Δ and (−)-2NDI-1PDI-Δ produce multiple easily accessible redox states, suggesting their potential use as electron accumulation or transport materials. The EPR and ENDOR spectra show that the unpaired electron in (−)-2PMDI-1PDI-Δ is localized on the PDI subunit, while it is partially shared between the NDI and PDI subunits in (−)-2NDI-1PDI-Δ. Such designed architectures exhibit multi-functional structural, optical, electronic and magnetic properties associated with their degree of chirality, rigidity, accessible cavities, through-space electron sharing, and several readily accessible redox states, allowing for the design and synthesis of new active materials.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Examples

Materials

The mono-N-Boc protected-trans-1,2-cyclohexanediamine derivative 2,[67] symmetric equilateral triangles [(−)-3NDI-Δ[49] and (−)-3PMDI-Δ[60]], the compounds (−)-2PMIA,[54] (−)-2NDI-2NH$_2$,[56] all of the reference molecules—namely, bis(cyclohexyl)perylenetetracarboxylic diimide[9] (Ref-PDI), bis(cyclohexyl)naphthalene tetracarboxylic diimide[62] (Ref-NDI) and bis(cyclohexyl)pyromellitic diimide[61] (Ref-PMDI)—were prepared according to previous literature procedures.

Synthetic Protocols
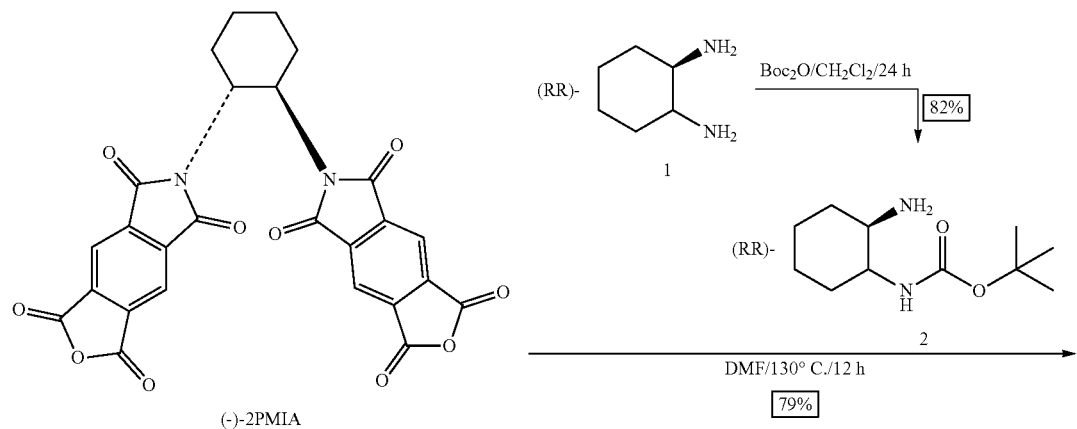
SCHEME 2. Synthesis of (-)-2PMDI-2NHBoc
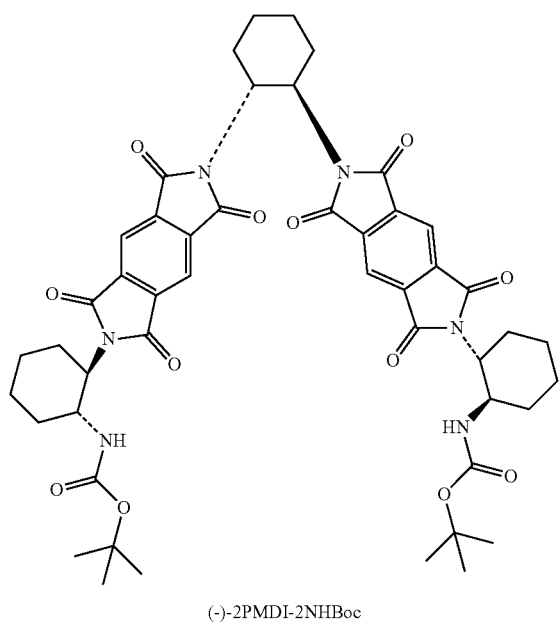

(−)-2PMDI-2NHBoc.

A solution of compound 2[1] (535 mg, 2.5 mmol) in anhydrous DMF (10 mL) was added quickly to a vigorously stirred homogenous solution of (−)-2PMIA[2] (518 mg, 1.0 mmol) in anhydrous DMF (15 mL) at 70° C. under $N_2$. The resulting reaction mixture was stirred overnight at 130° C. under $N_2$, after which the DMF was removed under reduced pressure (~3 mbar) at 60'° C. The crude residue was purified by column chromatography ($SiO_2$: $CH_2Cl_2/Me_2CO$, gradient from 0-10% $Me_2CO$) to afford pure (−)-2PMDI-2NHBoc (750 mg, 0.83 mmol) in 79% yield as an off-white powder. $^1$H NMR (500 MHz, $CDCl_3$, 25° C.) δ=8.28-7.86 (m, 4H), 4.98-4.89 (m, 2H), 4.38-4.27 (m, 2H), 4.19-4.00 (m, 2H), 3.95-3.78 (m, 2H), 2.65-2.42 (m, 4H), 2.13-0.95 (m, 38H). $^{13}$C NMR (125 MHz, $CDCl_3$, 25° C.) δ=166.5, 166.1, 155.4, 137.1, 118.3, 79.3, 56.9, 51.8, 50.3, 33.2, 33.0, 28.9, 28.4, 28.1, 28.0, 25.4, 25.4, 25.0, 24.8. ESI-HRMS (m/z): calcd for $[M+H]^+$=907.3872; found: 907.3845.

SCHEME 3. Synthesis of (−)-2PMDI-2NH$_2$

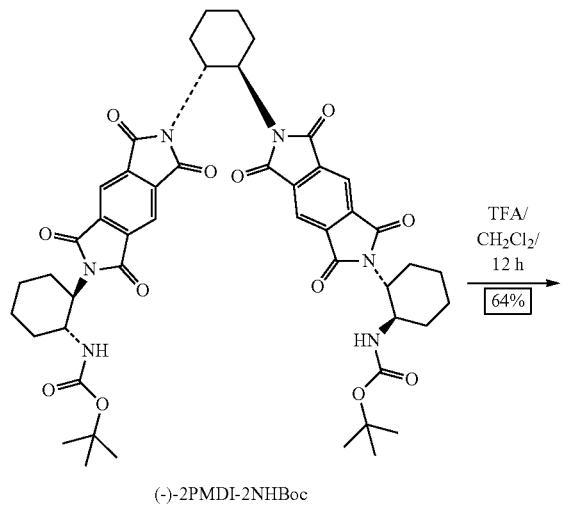

(−)-2PMDI-2NHBoc

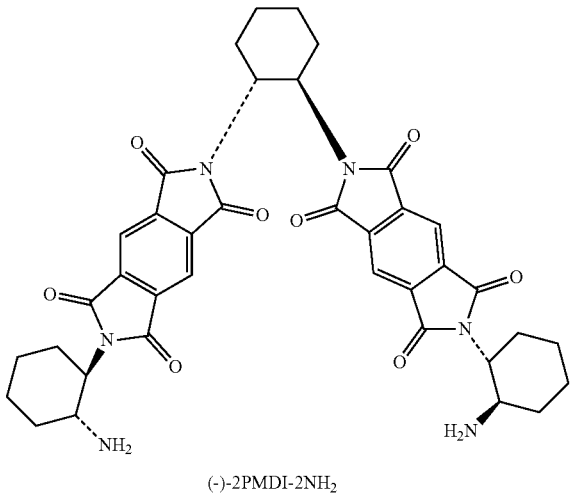

(−)-2PMDI-2NH$_2$

(−)-2PMDI-2NH$_2$.

(−)-2PMDI-2NHBoc (750 mg, 0.83 mmol) was dissolved in 1:1 ratio of $CH_2Cl_2$-trifluoroacetic acid (60 mL) and the solution was stirred at RT for 12 h. The solvent was then evaporated and the crude residue was dispersed in brine (20 mL) and aqueous $NH_{40}H$ was added until pH reached 12. The resulting solution was then extracted with $CH_2Cl_2$ (3×30 mL). The organic layers were combined, dried ($MgSO_4$) and concentrated under reduced pressure to afford pure (−)-2PMDI-2NH$_2$ (374 mg, 0.53 mmol) in 64% isolated yield as a light yellow solid. $^1$H NMR (500 MHz, $CDCl_3$, 25° C.) δ=8.26-7.99 (m, 4H), 5.03-4.95 (m, 2H), 3.88-3.75 (m, 2H), 3.42-3.29 (m, 2H), 2.58-2.43 (m, 2H), 2.27-1.02 (m, 26H). $^{13}$C NMR (125 MHz, $CDCl_3$, 25° C.) δ=166.7, 166.1, 137.3, 118.5, 118.3, 59.2, 59.0, 51.8, 51.0, 51.0, 37.6, 37.5, 29.5, 29.4, 29.1, 25.7, 25.7, 25.2, 25.2, 25.0. ESI-HRMS (m/z): calcd for $[M+H]^+$=707.2824; found: 707.2827.

SCHEME 4. Synthesis of (−)-2PMDI-1PDI-Δ

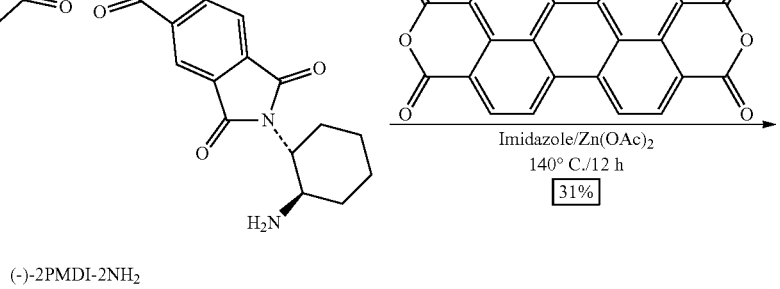

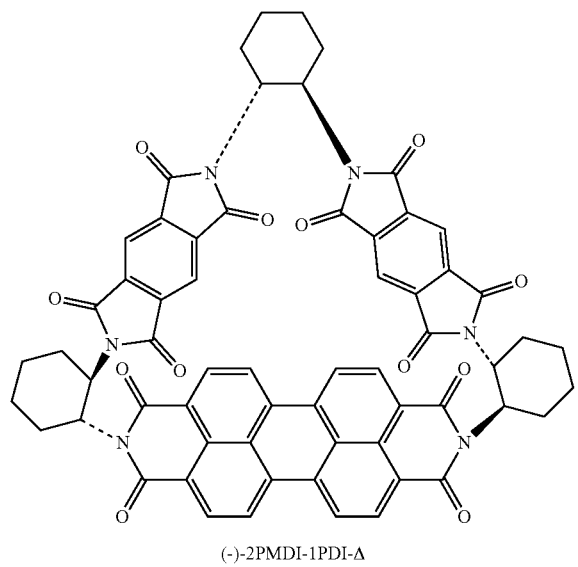

(−)-2PMDI-1PDI-Δ

(−)-2PMDI-1PDI-Δ.

The compounds (−)-2PMDI-2NH$_2$ (226 mg, 0.32 mmol), perylene-3,4:9,10-tetracarboxylic acid bisanhydride (125 mg, 0.32 mmol) and zinc acetate (75 mg, 0.34 mmol) were mixed with imidazole (25 g). The reaction mixture was stirred overnight at 140° C. under N$_2$. After cooling to room temperature, 1N HCl (200 ml) was added and the resulting solution was extracted with CH$_2$Cl$_2$ (3×200 ml). The organic layers were combined, dried (MgSO$_4$) and concentrated under reduced pressure. The crude red residue was purified by column chromatography (SiO$_2$: CH$_2$Cl$_2$/Me$_2$CO, gradient from 0-10% Me$_2$CO) to afford pure (−)-2PMDI-1PDI-Δ (105 mg, 0.099 mmol) in 31% yield as a deep red solid. $^1$H NMR (500 MHz, CDCl$_3$, 25° C.) δ=8.57 (d, J=8.0 Hz, 2H), 8.50 (d, J=8.0 Hz, 2H), 8.45 (overlapped doublets, J=8.0, 7.7 Hz, 4H), 7.83 (s, 4H), 5.80 (td, J=11.7, 3.6 Hz, 2H), 5.42 (td, J=11.8, 3.4 Hz, 2H), 5.24-5.16 (m, 2H), 2.64-2.52 (m, 2H), 2.24-2.13 (m, 4H), 2.02-1.91 (m, 6H), 1.85-1.75 (m, 6H), 1.75-1.60 (m, 4H), 1.5-1.39 (m, 2H). $^{13}$C NMR (125 MHz, CDCl$_3$, 25° C.) δ=166.5, 165.8, 165.8, 165.0, 163.3, 163.2, 137.1, 136.6, 136.5, 136.1, 134.8, 134.4, 132.0, 131.2, 129.1, 126.3, 123.4, 123.3, 123.2, 122.7, 118.4, 118.3, 54.4, 51.7, 51.4, 31.5, 31.1, 30.0, 25.7, 25.6, 24.8. ESI-HRMS (m/z): calcd for [M+H]$^+$=1063.2933; found: 1063.2917.

SCHEME 5. Synthesis of (−)-2NDI-1PDI-Δ

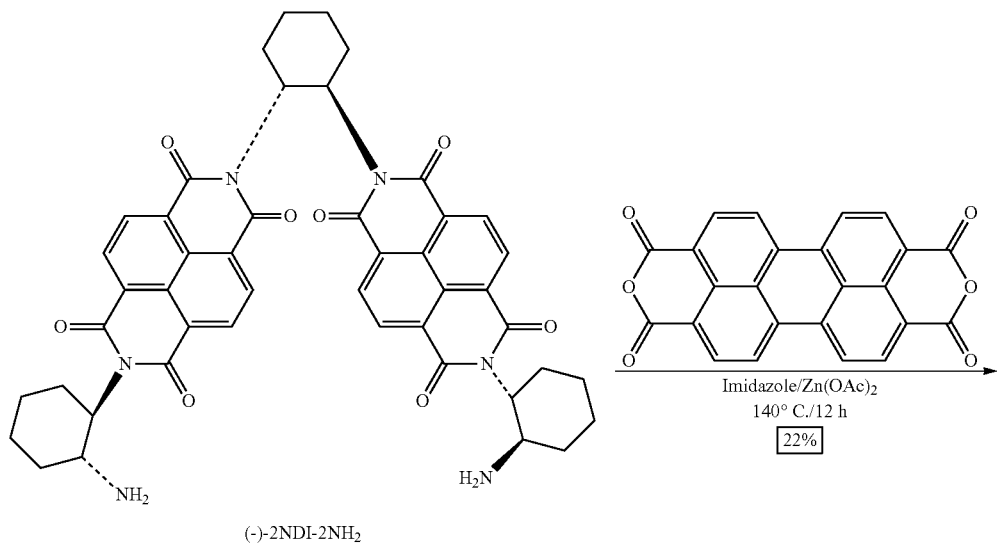

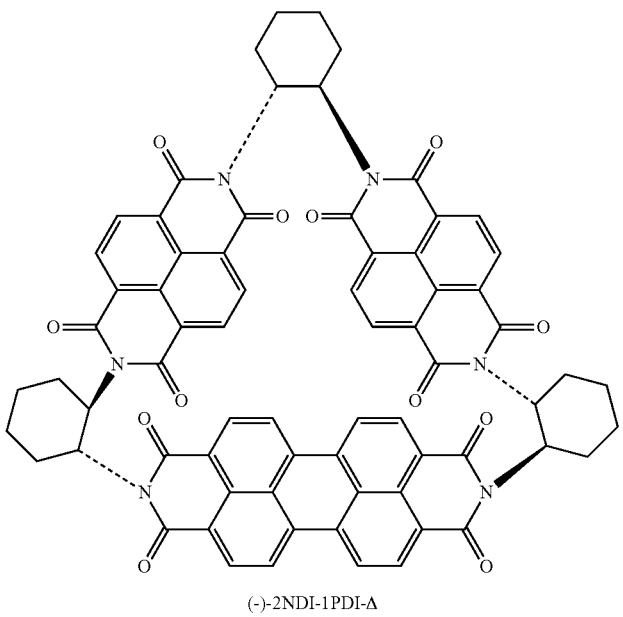

(−)-2NDI-1PDI-Δ

(−)-2NDI-1PDI-Δ.

The compounds (−)-2NDI-2NH$_2$[3] (439 mg, 0.54 mmol), perylene-3,4:9,10-tetracarboxylic acid bisanhydride (214 mg, 0.54 mmol) and zinc acetate (127 mg, 0.58 mmol) were mixed with imidazole (43 g). The reaction mixture was stirred overnight at 140° C. under N$_2$. After cooling to room temperature, 1N HCl (200 ml) was added and the resulting solution was extracted with CH$_2$Cl$_2$ (3×200 ml). The organic layers were combined, dried (MgSO$_4$) and concentrated under reduced pressure. The crude red residue was purified by column chromatography (SiO$_2$: CH$_2$Cl$_2$/Me$_2$CO, gradient from 0-10% Me$_2$CO) to afford pure (−)-2NDI-1PDI-Δ (139 mg, 0.12 mmol) in 22% yield as a bright red solid. $^1$H NMR (500 MHz, CDCl$_3$, 25° C.) δ=8.52-8.38 (m, 12H), 8.28 (dd, J=12.7, 8.1 Hz, 4H), 6.44-6.35 (m, 2H), 6.23-6.11 (m, 4H), 2.70-2.57 (m, 2H), 2.51-2.37 (m, 2H), 2.37-2.25 (m, 2H), 2.20-2.12 (m, 2H), 2.05-1.93 (m, 6H), 1.88-1.67 (m, 8H), 1.63-1.58 (m, 2H). $^{13}$C NMR (125 MHz, CDCl$_3$, 25° C.) δ=163.4, 163.3, 163.2, 162.8, 162.5, 134.2, 134.2, 131.6, 131.4, 131.3, 131.1, 131.0, 130.4, 129.0, 127.0, 126.5, 126.4, 126.3, 126.3, 126.2, 125.8, 123.2, 123.2, 123.0, 122.8, 54.6, 54.4, 54.3, 30.5, 30.3, 30.2, 26.0, 25.6. ESI-HRMS (m/z): calcd for [M+H]$^+$=1163.3246; found: 1163.3213.

Crystallographic Characterization 1) (−)-2PMDI-1PDI-Δ in 1,2-dichloroethane/n-hexane System (CCDC 1815897):

a) Method:

Single crystals of (−)-2PMDI-1PDI-Δ were grown by slow vapor diffusion of n-hexane into a 3.0 mM solution in 1,2-dichloroethane over the course of 3 days. A suitable single crystal was selected and the crystal was mounted on a MITIGEN holder in Paratone oil on a Kappa Apex 2 diffractometer. The crystal was kept at 99.99 K during data collection. Using Olex2,[4] the structure was solved with the SheXT[5] structure solution program using Direct Methods and refined with the SheXL[6] refinement package using Least Squares minimization.

b) Crystal Data:

Empirical formula=C$_{132}$H$_{102}$Cl$_2$N$_{12}$O$_{24}$, formula weight=2311.15, crystal system=orthorhombic, space group =P2$_1$2$_1$2 (no. 18), a=30.1044(9), b=31.9984(10), c=12.4179(4) Å, α=β=γ=90°, V=11962.1(6) Å$^3$, Z=4, T=99.99 K, μ(CuKα)=1.130 mm$^{-1}$, D$_{calc}$=1.283 g/mm$^3$, 86230 reflections measured (5.524≤2Θ≤136.662), 21607 unique (R$_{int}$=0.0722, R$_{sigma}$=0.0555) which were used in all calculations. The final R$_1$ was 0.0651 (I>2σ(I)) and wR$_2$ was 0.1880 (all data).

c) Refinement Details:

The enhanced rigid-bond restraint (SHELX keyword RIGU) was applied on the n-hexane solvent.[7] Rigid bond restraints (esd 0.01) were imposed on the displacement parameters of the 1,2-dichloroethane solvent molecules. The carbon atoms on the 1,2-dichloroethane molecules were restrained esd (0.01) that their Uij components were approximate to isotropic.

d) Solvent Treatment Details:

Total solvent accessible volume/cell=1593.5 Å$^3$ [13.3%] Total electron count/cell=437.4. The solvent masking procedure as implemented in Olex2 was used to remove the electronic contribution of solvent molecules from the refinement. As the exact solvent content is not known, only the atoms used in the refinement model are reported in the formula here.

2) (−)-2NDI-1PDI-Δ in CHCl$_3$ (CCDC 1815898):

a) Method:

Single crystals of (−)-2NDI-1PDI-Δ were grown by slow evaporation of 6 mM solution in CHCl$_3$ over the course of 7 days. A suitable single crystal was selected and the crystal was mounted on a MITIGEN holder in Paratone oil on a Kappa Apex 2 diffractometer. The crystal was kept at 99.99 K during data collection. Using Olex2[4], the structure was solved with the ShelXT[5] structure solution program using Intrinsic Phasing and refined with the XL[6] refinement package using Least Squares minimization.

b) Crystal Data:

Empirical formula=$C_{145}H_{97}Cl_{15}N_{12}O_{24}$, formula weight=2923.09, monoclinic, space group C2 (no. 5), a=43.1347(12), b=14.6175(4), c=24.2886(6) Å, α=90°, β=102.9369(16)°, γ=90°, V=14925.8(7) Å$^3$, Z=4, T=99.99 K, (CuKα)=3.111 mm$^{-1}$, $D_{calc}$=1.301 g/mm$^3$, 57433 reflections measured (3.732≤2Θ≤127.504), 24109 unique ($R_{int}$=0.0874, $R_{sigma}$=0.1027) which were used in all calculations. The final $R_1$ was 0.0634 (I>2σ(I)) and w$R_2$ was 0.1753 (all data).

c) Refinement Details:

The enhanced rigid-bond restraint (SHELX keyword RIGU) was applied globally.[7]

d) Solvent Treatment Details.

The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=3130.9 Å$^3$ [21.0%] Total electron count/cell=958.5.

3) (−)-2PMDI-1PDI-Δ in CHCl$_3$/n-hexane System (CCDC 1879108):

a) Method:

Single crystals of (−)-2PMDI-1PDI-Δ were grown by slow vapor diffusion of n-hexane into a 3.0 mM solution in CHCl$_3$ over the course of 3 days. A suitable crystal was selected and the crystal was mounted on a MITIGEN holder in Paratone oil on a Kappa Apex 2 diffractometer. The crystal was kept at 99.99 K during data collection. Using Olex2,[15] the structure was solved with the SheXS[19] structure solution program using Direct Methods and refined with the XL[19] refinement package using Least Squares minimization.

b) Crystal Data:

Empirical Formula=$C_{125}H_{85}Cl_3N_{12}O_{24}$, formula weight=2245.40, crystal system=orthorhombic, space group =P2$_1$2$_1$2 (no. 18), a=30.418(3) Å, b=31.784(3) Å, c=12.380(12) Å, α=β=γ=90°, V=11969(2) Å$^3$, Z=4, T=99.99 K, (CuKα)=1.316 mm$^{-1}$, $D_{calc}$=1.246 g/mm$^3$, 199950 reflections measured (4.02≤2Θ≤137.344), 21787 unique ($R_{int}$=0.0826, $R_{sigma}$=0.0492) which were used in all calculations. The final $R_1$ was 0.0578 (I≥2σ(I)) and w$R_2$ was 0.1756 (all data).

c) Refinement Details:

No special refinement necessary.

d) Solvent Treatment Details:

The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=2565.3 Å$^3$ [21.3%] Total electron count/cell=745.2

4) Solvent-Free Crystals of (−)-2PMDI-1PDI-Δ (CCDC 1879109):

a) Method:

Solvent-free single crystals of (−)-2PMDI-1PDI-Δ were obtained by air drying, for several days, the single crystals grown by slow vapor diffusion of n-hexane into a 3.0 mM solution in CHCl$_3$. A suitable crystal was selected and the crystal was mounted on a MITIGEN holder in Paratone oil on a Bruker Kappa APEX CCD area detector diffractometer. The crystal was kept at 99.99 K during data collection. Using Olex2,[15] the structure was solved with the SheXS[19] structure solution program using Direct Methods and refined with the ShelXL[17] refinement package using Least Squares minimization.

b) Crystal Data:

Empirical Formula=$C_{62}H_{42}N_6O_{12}$, formula weight=1063.01, crystal system=orthorhombic, space group=P2$_1$2$_1$2 (no. 18), a=30.307(18) Å, b=32.069(2) Å, c=12.6054(8) Å, α=β=γ=90°, V=12251.5(13) Å$^3$, Z=8, T=99.99 K, μ(CuKα)=0.672 mm$^{-1}$, $D_{calc}$=1.153 g/mm$^3$, 43511 reflections measured (5.512≤2Θ≤127.668), 19023 unique ($R_{int}$=0.0896, $R_{sigma}$=0.1606) which were used in all calculations. The final $R_1$ was 0.1129 (I>2σ(I)) and w$R_2$ was 0.3309 (all data).

c) Refinement Details:

No special refinement necessary.

d) Solvent Treatment Details: Not applicable.

Variable-Temperature Powder XRD (VT-PXRD) Measurements

Powder X-ray diffractions were conducted on a STOE-STADI MP powder diffractometer equipped with an asymmetric curved Germanium monochromator (CuKα1 radiation, λ=1.54056 Å) and one-dimension silicon strip detector (MYTHEN2 1K from DECTRIS). The line focused Cu X-ray tube was operated at 40 kV and 40 mA. Samples for structural analysis were measured at room temperature in transmission geometry. The VT-PXRD experiments of both the as-synthesized isosceles triangles were conducted in a spinning capillary tube with the temperature varying from 298 up to 473 K under air. The samples were then cooled to room temperature.

Thin Film X-Ray Diffraction Measurements

Thin film X-ray diffractions were conducted on a Rigaku Smartlab instrumentation configured with a high-intensity Cu rotating anode generator and a parallel beam multilayer mirror (CuKα1 radiation, λ=1.540593 Å and CuKα2 radiation, λ=1.544414 Å). Samples were scanned continuously at 45 kV×160 mA, a step size of 2θ=0.03 degree (3 s per step) over a 2θ range of 5 to 30 degrees. Thin film samples were prepared by drop casting 0.5 mg/ml solution of the isosceles triangles in CH$_2$Cl$_2$ onto piranha-cleaned Si wafer.

Photophysical Studies and Quantum Yield Measurements

UV/Vis absorption spectra were recorded using a UV-3600 Shimadzu spectrophotometer. Steady-state and time-resolved photoluminescence (TRPL) spectra were acquired using HORIBA Fluorolog-3 equipped with a 450-W xenon lamp and a TCSPC module (diode laser excitation at λ=375 nm) and an integrating sphere (Horiba Quanta-φ) for absolute photoluminescence quantum yield determination. The spectra were corrected for the monochromator wavelength dependence and photomultiplier response functions provided by the manufacturer. Relative fluorescence quantum yields in solution were measured under high dilution conditions (optical density <0.05) using N,N'-dicyclohexylperylene-3,4:9,10-tetracarboxylic acid diimide as a reference compound. Absolute photoluminescence quantum yields in the solid state were measured using (i) as-synthesized powder samples which were placed in a 10 mm diameter holder with a quartz window, as well as (ii) thin film samples which were prepared on quartz slides. All quantum yields were measured in triplicate. Diffuse reflectance measurements were performed using Shimadzu UV-3600 Plus UV-Vis-NIR Spectrophotometer equipped with a 150 mm diam. integrating sphere attachment (ISR-1503F). The powder samples were mixed with a barium sulfate matrix prior to measurements. Circular dichroism (CD) measurements were carried out on a Jasco J-815 spectrometer.

Thermogravimetric Analyses (TGA)

The studies were carried out under a heating rate of 10° C. min up to 800° C. and a nitrogen flow rate of 50 cm$^3$ min$^{-1}$ using a SDT851 Mettler Toledo Instruments.

Computational Modeling

Quantum mechanics (QM) calculations were carried out on the level of M06-2X density functional[68,69] with 6-311G (d,p) basis sets as implemented in with Jaguar 8.2 (Jaguar, version 8.2, Schrödinger, LLC, New York, N.Y., 2013).). All the calculations include post-stage D3 van der Waals corrections,[65,66] which we expect to provide accurate descriptions of the non-covalent bonding interactions necessary for (−)-2PMDI-1PDI-Δ and (−)-2NDI-1PDI-Δ. Solvation effects were considered by using the Poisson-Boltzmann solvation model with parameters of dichloromethane (CH$_2$Cl$_2$). The optimized molecular geometries agree well with those in the solid state, but the solvated experimental structures are unavailable. Time-dependent density functional tight binding (TD-DFTB) was employed to predict the UV/Vis absorption spectra.[70] The strain due to the confinement of the triangle scaffold distorted the planar structure of PDI and the calculated structure of the strained PDI was obtained by cutting the C—C bond from the triangle and using hydrogen to saturate the broken bonds We estimated the strain energies by calculating the energy differences between the strained PDIs of both isosceles triangles and fully relaxed monomeric reference PDI compound.

EPR and ENDOR Measurements

The spectra were acquired at X-band (9.5 GHz) with a Bruker Elexsys E580 spectrometer, fitted with the DICE ENDOR accessory, an EN801 resonator, and an ENI A-500 RF power amplifier. Applied RF powers ranged from 200 to 400 W across the 7 MHz scanned range, and the microwave power ranged from 2 to 20 mW. EPR Spectra were recorded with 0.010 mT modulation amplitude. The sample temperatures were controlled by a liquid N$_2$ flow system. The EPR measurements were carried out on the monoreduced radical anions of the triangles and the reference compound generated by adding 1 mol equivalent of cobaltocene (CoCp$_2$) as the chemical reductant. Samples were loaded into 1.4 mm I.D. quartz tubes, which were sealed with epoxy resin in an argon-filled glove box. A spline fit baseline correction was applied to the ENDOR spectra following integration. The EPR and the ENDOR spectra were fitted in MATLAB using EasySpin v4.5.5.

Cyclic Voltammetry (CV) Experiments

CV measurements were carried out at room temperature in argon-purged solutions of CH$_2$Cl$_2$ with a Gamry Multipurpose instrument (Reference 600) interfaced to a PC. All CV experiments were performed using a glassy carbon working electrode (0.071 cm$^2$). The electrode surface was polished routinely with 0.05 µm alumina-water slurry on a felt surface immediately before use. The counter electrode was a Pt coil and the reference electrode was an Ag/AgCl electrode. The concentration of the sample and supporting electrolyte, tetrabutylammonium hexafluorophosphate (TBAPF$_6$), were 1.0 mM and 0.1 M, respectively. The CV cell was dried in an oven immediately before use, and argon was continually flushed through the cell as it was cooled down to room temperature to avoid condensation of water.

Spectroelectrochemistry Experiments.

Spectroelectrochemical measurements were performed using the electrochemical cell arrangement with a platinum mesh as the working electrode, a platinum wire as the counter electrode, and an Ag/AgCl reference electrode. Experiments were carried out in a BASi spectroelectrochemical cell (EF-1362), which was kept continuously under N$_2$ during the measurements. Absorption spectra were recorded on a UV-3600 Shimadzu spectrophotometer within the UV/Vis/NIR spectral range under several sequentially applied potentials.

REFERENCES

1 Qian, G. et al. Simple and efficient near-infrared organic chromophores for light-emitting diodes with single electroluminescent emission above 1000 nm. *Adv. Mater.* 21, 111-116 (2009).

2 Ning, Z. et al. Aggregation-induced emission (aie)-active starburst triarylamine fluorophores as potential non-doped red emitters for organic light-emitting diodes and cl2 gas chemodosimeter. *Adv. Funct. Mater.* 17, 3799-3807 (2007).

3 Méhes, G., Nomura, H., Zhang, Q., Nakagawa, T. & Adachi, C. Enhanced electroluminescence efficiency in a spiro-acridine derivative through thermally activated delayed fluorescence. *Angew. Chem., Int. Ed.* 51, 11311-11315 (2012).

4 Liu, J. et al. High mobility emissive organic semiconductor. *Nat. Commun.* 6, 10032 (2015).

5 Oniwa, K. et al. Single crystal biphenyl end-capped furan-incorporated oligomers: Influence of unusual packing structure on carrier mobility and luminescence. *J. Mater. Chem. C* 1, 4163-4170 (2013).

6 Oyamada, T. et al. Optical properties of oligo(9,9-diarylfluorene) derivatives in thin films and their application for organic light-emitting field-effect transistors. *J. Phys. Chem. C* 111, 108-115 (2007).

7 Wang, H. et al. Cyano-substituted oligo(p-phenylene vinylene) single crystals: A promising laser material. *Adv. Funct. Mater.* 21, 3770-3777 (2011).

8 Yang, Y. et al. Energy transfer mechanisms among various laser dyes co-doped into gel glasses. *Dyes Pigm.* 96, 242-248 (2013).

9 Chen, Z. J. et al. Colorimetric and ratiometric fluorescent chemosensor for fluoride ion based on perylene diimide derivatives. *Dyes Pigm.* 94, 410-415 (2012).

10 Han, T. et al. A fluorescence-switchable luminogen in the solid state: A sensitive and selective sensor for the fast "turn-on" detection of primary amine gas. *Chem. Commun.* 49, 4848-4850 (2013).

11 Roy, I. et al. E-bodipy fluorescent chemosensor for Zn$^{2+}$ ion. *J. Photochem. Photobiol. A* 331, 233-239 (2016).

12 Hou, X. et al. Tunable solid-state fluorescent materials for supramolecular encryption. *Nat. Commun.* 6 (2015).

13 Kishimura, A., Yamashita, T., Yamaguchi, K. & Aida, T. Rewritable phosphorescent paper by the control of competing kinetic and thermodynamic self-assembling events. *Nat. Mater.* 4, 546 (2005).

14 Birks, J. B. Photophysics of aromatic molecules (Wiley, 1970).

15 Qin, T. et al. Polytriphenylene dendrimers: A unique design for blue-light-emitting materials. *Angew. Chem., Int. Ed.* 47, 8292-8296 (2008).

16 Lee, Y.-T., Chiang, C.-L. & Chen, C.-T. Solid-state highly fluorescent diphenylaminospirobifluorenylfumaronitrile red emitters for non-doped organic light-emitting diodes. *Chem. Commun.*, 217-219 (2008).

17 Ramanan, C., Smeigh, A. L., Anthony, J. E., Marks, T. J. & Wasielewski, M. R. Competition between singlet fission and charge separation in solution-processed blend films of 6,13-bis(triisopropylsilylethynyl)pentacene with sterically-encumbered perylene-3,4:9,10-bis(dicarboximide)s. *J. Am. Chem. Soc.* 134, 386-397 (2012).

18 Iida, A. & Yamaguchi, S. Intense solid-state blue emission with a small stokes' shift: [small pi]-stacking protection of the diphenylanthracene skeleton. *Chem. Commun.*, 3002-3004 (2009).

19 An, B.-K., Kwon, S.-K., Jung, S.-D. & Park, S. Y. Enhanced emission and its switching in fluorescent organic nanoparticles. *J. Am. Chem. Soc.* 124, 14410-14415 (2002).

20 Kaiser, T. E., Wang, H., Stepanenko, V. & Würthner, F. Supramolecular construction of fluorescent j-aggregates based on hydrogen-bonded perylene dyes. *Angew. Chem., Int. Ed.* 46, 5541-5544 (2007).

21 Zhao, C.-H., Wakamiya, A., Inukai, Y. & Yamaguchi, S. Highly emissive organic solids containing 2,5-diboryl-1, 4-phenylene unit. *J. Am. Chem. Soc.* 128, 15934-15935 (2006).

22 Wakamiya, A., Mori, K. & Yamaguchi, S. 3-boryl-2,2'-bithiophene as a versatile core skeleton for full-color highly emissive organic solids. *Angew. Chem., Int. Ed.* 46, 4273-4276 (2007).

23 Luo, J. et al. Aggregation-induced emission of 1-methyl-1,2,3,4,5-pentaphenylsilole. *Chem. Commun.*, 1740-1741 (2001).

24 Yuan, W. Z. et al. Changing the behavior of chromophores from aggregation-caused quenching to aggregation-induced emission: Development of highly efficient light emitters in the solid state. *Adv. Mater.* 22, 2159-2163 (2010).

25 Mei, J., Leung, N. L. C., Kwok, R. T. K., Lam, J. W. Y. & Tang, B. Z. Aggregation-induced emission: Together we shine, united we soar! *Chem. Rev.* 115, 11718-11940 (2015).

26 Wurthner, F. Perylene bisimide dyes as versatile building blocks for functional supramolecular architectures. *Chem. Commun.*, 1564-1579 (2004).

27 Würthner, F. et al. Perylene bisimide dye assemblies as archetype functional supramolecular materials. *Chem. Rev.* 116, 962-1052 (2016).

28 Görl, D., Zhang, X. & Würthner, F. Molecular assemblies of perylene bisimide dyes in water. *Angew. Chem., Int. Ed.* 51, 6328-6348 (2012).

29 Anthony, J. E., Facchetti, A., Heeney, M., Marder, S. R. & Zhan, X. N-type organic semiconductors in organic electronics. *Adv. Mater.* 22, 3876-3892 (2010).

30 Zhan, X. et al. Rylene and related diimides for organic electronics. *Adv. Mater.* 23, 268-284 (2011).

31 Li, G. et al. Synthesis, characterization, physical properties, and oled application of single bn-fused perylene diimide. *J. Org. Chem.* 80, 196-203 (2015).

32 Jones, B. A. et al. High-mobility air-stable n-type semiconductors with processing versatility: Dicyanoperylene-3,4:9,10-bis(dicarboximides). *Angew. Chem., Int. Ed.* 43, 6363-6366 (2004).

33 Zhan, X. et al. A high-mobility electron-transport polymer with broad absorption and its use in field-effect transistors and all-polymer solar cells. *J. Am. Chem. Soc.* 129, 7246-7247 (2007).

34 Zhang, X. et al. A potential perylene diimide dimer-based acceptor material for highly efficient solution-processed non-fullerene organic solar cells with 4.03% efficiency. *Adv. Mater.* 25, 5791-5797 (2013).

35 Zhou, E. et al. All-polymer solar cells from perylene diimide based copolymers: Material design and phase separation control. *Angew. Chem., Int. Ed.* 50, 2799-2803 (2011).

36 Li, C. & Wonneberger, H. Perylene imides for organic photovoltaics: Yesterday, today, and tomorrow. *Adv. Mater.* 24, 613-636 (2012).

37 Schmidt, R. et al. High-performance air-stable n-channel organic thin film transistors based on halogenated perylene bisimide semiconductors. *J. Am. Chem. Soc.* 131, 6215-6228 (2009).

38 Krieg, E., Weissman, H., Shirman, E., Shimoni, E. & Rybtchinski, B. A recyclable supramolecular membrane for size-selective separation of nanoparticles. *Nat Nano* 6, 141-146 (2011).

39 Würthner, F. Bay-substituted perylene bisimides: Twisted fluorophores for supramolecular chemistry. *Pure Appl. Chem.* 78, 2341-2349 (2006).

40 Safont-Sempere, M. M., Osswald, P., Radacki, K. & Würthner, F. Chiral self-recognition and self-discrimination of strapped perylene bisimides by π-stacking dimerization. *Chem. Eur. J.* 16, 7380-7384 (2010).

41 Safont-Sempere, M. M. et al. Impact of molecular flexibility on binding strength and self-sorting of chiral π-surfaces. *J. Am. Chem. Soc.* 133, 9580-9591 (2011).

42 Jimenez, A. J. et al. Structure-property relationships for 1,7-diphenoxy-perylene bisimides in solution and in the solid state. *Chem. Sci.* 5, 608-619 (2014).

43 Lin, M.-J., Jimenez, A. J., Burschka, C. & Wurthner, F. Bay-substituted perylene bisimide dye with an undistorted planar scaffold and outstanding solid state fluorescence properties. *Chem. Commun.* 48, 12050-12052 (2012).

44 Schlosser, F., Stepanenko, V. & Wurthner, F. Perylene bisimide macrocycles and their self-assembly on hopg surfaces. *Chem. Commun.* 46, 8350-8352 (2010).

45 Schlosser, F., Sung, J., Kim, P., Kim, D. & Wurthner, F. Excitation energy migration in covalently linked perylene bisimide macrocycles. *Chem. Sci.* 3, 2778-2785 (2012).

46 Shao, Y. et al. Engineering [small pi]-[small pi] interactions for enhanced photoluminescent properties: Unique discrete dimeric packing of perylene diimides. *RSC Advances* 7, 6530-6537 (2017).

47 Wu, Y. et al. Electron delocalization in a rigid cofacial naphthalene-1,8:4,5-bis(dicarboximide) dimer. *Angew. Chem., Int. Ed.* 53, 9476-9481 (2014).

48 Samanta, A. et al. Supramolecular double-helix formation by diastereoisomeric conformations of configurationally enantiomeric macrocycles. *J. Am. Chem. Soc.* 138, 14469-14480 (2016).

49 Schneebeli, S. T. et al. Electron sharing and anion-π recognition in molecular triangular prisms. *Angew. Chem., Int. Ed.* 52, 13100-13104 (2013).

50 Liu, Z. et al. Assembly of supramolecular nanotubes from molecular triangles and 1,2-dihalohydrocarbons. *J. Am. Chem. Soc.* 136, 16651-16660 (2014).

51 Wu, Y. et al. Ultrafast photoinduced symmetry-breaking charge separation and electron sharing in perylenediimide molecular triangles. *J. Am. Chem. Soc.* 137, 13236-13239 (2015).

52 Chen, D. et al. A rigid naphthalenediimide triangle for organic rechargeable lithium-ion batteries. *Adv. Mater.* 27, 2907-2912 (2015).

53 Liu, Z. et al. Supramolecular gelation of rigid triangular macrocycles through rings of multiple c-h . . . o interactions acting cooperatively. *J. Org. Chem.* 81, 2581-2588 (2016).

54 Nalluri, S. K. M. et al. Chiral redox-active isosceles triangles. *J. Am. Chem. Soc.* 138, 5968-5977 (2016).

55 Wu, Y., Krzyaniak, M. D., Stoddart, J. F. & Wasielewski, M. R. Spin frustration in the triradical trianion of a naphthalenediimide molecular triangle. *J. Am. Chem. Soc.* 139, 2948-2951 (2017).
56 Wu, Y. et al. Charge and spin transport in an organic molecular square. *Angew. Chem.*, Int. Ed. 54, 11971-11977 (2015).
57 Liu, Z., Nalluri, S. K. M. & Stoddart, J. F. Surveying macrocyclic chemistry: From flexible crown ethers to rigid cyclophanes. *Chem. Soc. Rev.* 46, 2459-2478 (2017).
58 Mizuno, A. et al. Discovery of the k4 structure formed by a triangular π radical anion. *J. Am. Chem. Soc.* 137, 7612-7615 (2015).
59 Mizuno, A. et al. 3d spin-liquid state in an organic hyperkagome lattice of mott dimers. *Phys. Rev. Lett.* 119, 057201 (2017).
60 Gawronski, J. et al. Novel chiral pyromellitdiimide (1,2,4,5-benzenetetracarboxydiimide) dimers and trimers: Exploring their structure, electronic transitions, and exciton coupling. *Chem. Eur. J.* 8, 2484-2494 (2002).
61 Gawronski, J., Brzostowska, M., Kacprzak, K., Kolbon, H. & Skowronek, P. Chirality of aromatic bis-imides from their circular dichroism spectra. *Chirality* 12, 263-268 (2000).
62 Shukla, D. et al. Thin-film morphology control in naphthalene-diimide-based semiconductors: High mobility n-type semiconductor for organic thin-film transistors. *Chem. Mater.* 20, 7486-7491 (2008).
63 Che, Y. et al. Interfacial engineering of organic nanofibril heterojunctions into highly photoconductive materials. *J. Am. Chem. Soc.* 133, 1087-1091 (2011).
64 Che, Y., Yang, X., Balakrishnan, K., Zuo, J. & Zang, L. Highly polarized and self-waveguided emission from single-crystalline organic nanobelts. *Chem. Mater.* 21, 2930-2934 (2009).
65 Grimme, S., Antony, J., Ehrlich, S. & Krieg, H. A consistent and accurate ab initio parametrization of density functional dispersion correction (DFT-d) for the 94 elements h-pu. *J. Chem. Phys.* 132, 154104 (2010).
66 Goerigk, L. & Grimme, S. A thorough benchmark of density functional methods for general main group thermochemistry, kinetics, and noncovalent interactions. *Phys. Chem. Chem. Phys.* 13, 6670-6688 (2011).
67 Yu, L. & Li, P. New simple primary amine-thiourea organocatalysts and their application in asymmetric conjugate addition. *Tetrahedron Lett.* 55, 3697-3700 (2014).
68 Zhao, Y. & Truhlar, D. G. Density functionals with broad applicability in chemistry. *Acc. Chem. Res.* 41, 157-167 (2008).
69 Zhao, Y. & Truhlar, D. G. The m06 suite of density functionals for main group thermochemistry, thermochemical kinetics, noncovalent interactions, excited states, and transition elements: Two new functionals and systematic testing of four m06-class functionals and 12 other functionals. *Theor. Chem. Acc.* 120, 215-241 (2008).
70 Rüger, R., Lenthe, E. v., Heine, T. & Visscher, L. Tight-binding approximations to time-dependent density functional theory—a fast approach for the calculation of electronically excited states. *J. Chem. Phys.* 144, 184103 (2016).

We claim:

1. A rigid macrocycle comprising:
   (a) three diimide subunits, the three diimide subunits consisting of (i) a poly(peri-naphthalene) diimide (PPNDI) subunit and (ii) two naphthalene diimide (NDI) subunits or two pyromellitic diimide (PMDI) subunits, and
   (b) three chiral linking subunits linking the three diimide subunits.

2. The rigid macrocycle of claim 1, wherein the PPNDI subunit comprises a PPNDI of formula

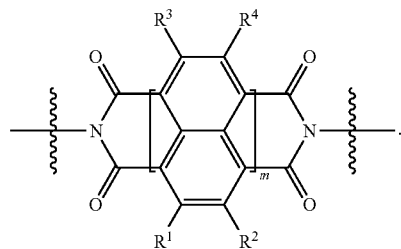

wherein each of $R^1$, $R^2$, $R^3$, and $R^4$ of the PPNDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, and a sulfate moiety and m is greater than or equal to 2 and less than or equal to 10;

wherein the NDI subunit comprises a NDI of formula

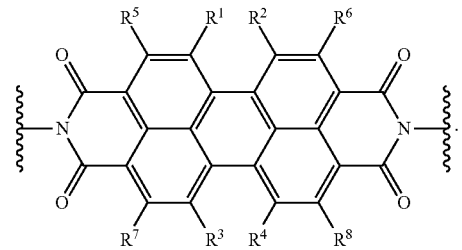

wherein each of $R^1$, $R^2$, $R^3$, $R^4$, $R^5$, $R^6$, $R^7$, and $R^8$ of the PPNDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, and a sulfate moiety;

wherein the macrocycle comprises the PMDI of formula

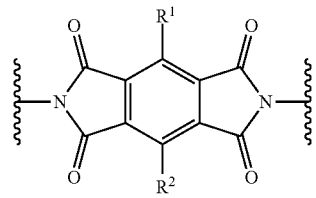

wherein each of $R^1$ and $R^2$ of the PMDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety; and wherein the three chiral linking subunits are (i) a (RR)-trans-1,2-cycloalkyl subunit, or (ii) a (SS)-trans-1,2-cycloalkyl subunit.

3. The rigid macrocycle of claim 2, wherein the macrocycle comprises the PPNDI of formula

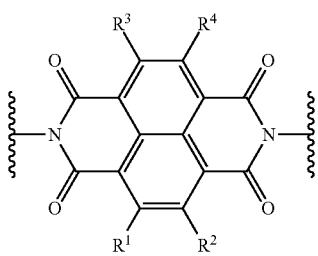

wherein each of $R^1$, $R^2$, $R^3$, and $R^4$ of the NDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety;

wherein the PMDI subunit comprises a NDI of formula

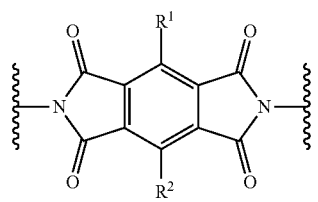

wherein each of $R^1$ and $R^2$ of the PMDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety; or wherein the three chiral linking subunits are (i) a (RR)-trans-1,2-cycloalkyl subunit, or (ii) a (SS)-trans-1,2-cycloalkyl subunit.

4. The rigid macrocycle of claim 3, wherein the macrocycle is a compound of Formula (6)

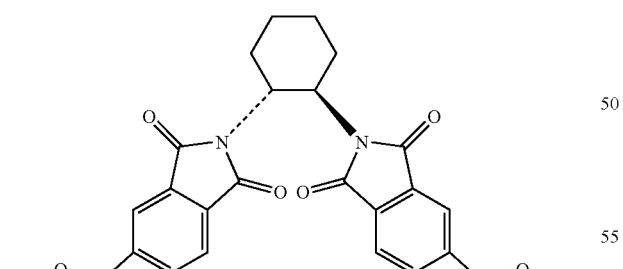

or a compound of Formula (7)

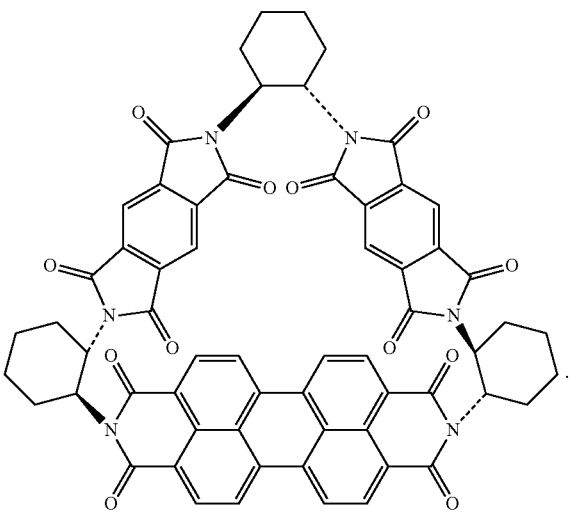

5. The rigid macrocycle of claim 2, wherein the macrocycle comprises the PPNDI of formula

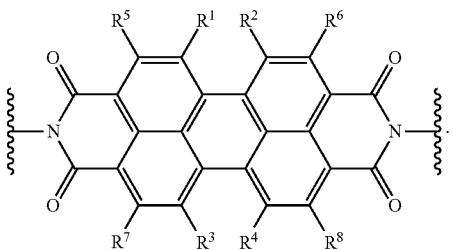

wherein each of $R^1$, $R^2$, $R^3$, $R^4$, $R^5$, $R^6$, $R^7$, and $R^8$ of the PPNDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, and a sulfate moiety;

wherein the macrocycle comprises the NDI of formula

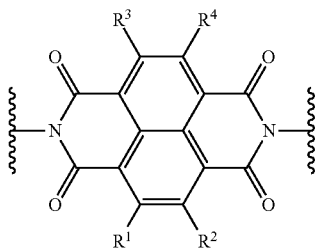

wherein each of $R^1$, $R^2$, $R^3$, and $R^4$ of the NDI subunit is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, a sulfate moiety; and wherein the three chiral linking subunits are (i) a (RR)-trans-1,2-cycloalkyl subunit, or (ii) a (SS)-trans-1,2-cycloalkyl subunit.

6. The rigid macrocycle of claim 5, wherein the macrocycle is a compound of Formula (4)

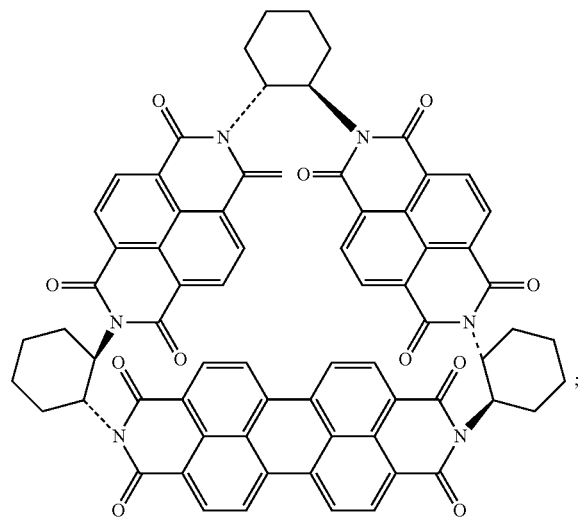

or a compound of Formula (5)

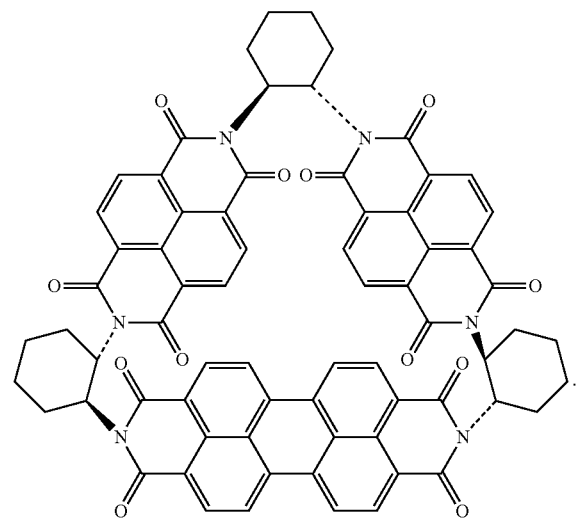

7. The rigid macrocycle of claim 1, wherein the diimide subunits form a triangular macrocycle having $C_2$ symmetry.

8. A crystalline composition comprising a plurality of the rigid macrocycles of claim 1.

9. The crystalline composition of claim 8, wherein the plurality of rigid macrocycles are arranged in a plurality of dimers by π-π stacking PPNDI subunits.

10. A photoluminescent material comprising the rigid macrocycle of claim 1.

11. The photoluminescent material of claim 10, wherein the material comprises a crystalline composition comprising a plurality of the rigid macrocycles, wherein the plurality of rigid macrocycles are arranged in a plurality of dimers by π-π stacking PPNDI subunits.

12. The photoluminescent material of claim 10, wherein the quantum yield is greater than 0.5.

13. The photoluminescent material of claim 10, wherein the material is excited by electromagnetic radiation having a wavelength of 200 nm to 700 nm and/or wherein material emits electromagnetic radiation having a wavelength of 350 nm to 800 nm.

14. The photoluminescent material of claim 10, wherein material emits electromagnetic radiation having a $\lambda_{max}$ wavelength of about 500 nm to about 715 nm.

15. A method of preparing a rigid macrocycle, the method comprising cyclocondensing a first reagent comprising a compound of formula

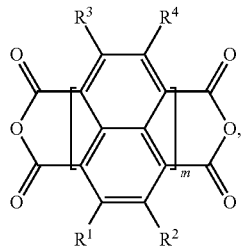

wherein each of $R^1$, $R^2$, $R^3$, and $R^4$ is independently selected from the group consisting of hydrogen, a halogen, an alkyl moiety, an alkenyl moiety, an alkynyl moiety, a hydroxyl moiety, an alkoxy moiety, a phenoxy moiety, a carbonyl moiety, a cyanide moiety, and a sulfate moiety and m is greater than or equal to 2 and less than or equal to 10, and a second reagent comprising (i) two NDI subunits or two PMDI subunits and (ii) three chiral linking subunits.

16. A method for stimulating light emission, the method comprising:
(a) providing the photoluminescent material of claim 10 and
(b) exciting the macrocycle with electromagnetic radiation in the near-ultraviolet or visible range.

17. The method of claim 16, wherein the material is excited by electromagnetic radiation having a wavelength of 200 nm to 700 nm and/or wherein material emits electromagnetic radiation having a wavelength of 350 nm to 800 nm.

18. The method of claim 16, wherein the quantum yield is greater than 0.5.

19. The method of claim 16, wherein the material comprises a crystalline composition comprising a plurality of the rigid macrocycles.

20. The method of claim 19, wherein the plurality of rigid macrocycles are arranged in a plurality of dimers by π-π stacking PPNDI subunits.

* * * * *